United States Patent
Shen et al.

(10) Patent No.: US 11,564,381 B2
(45) Date of Patent: Jan. 31, 2023

(54) GENETICALLY MODIFIED NON-HUMAN ANIMAL WITH HUMAN OR CHIMERIC LAG3

(71) Applicants: Biocytogen JiangSu Co., Ltd., Haimen (CN); Biocytogen Pharmaceuticals (Beijing) Co., Ltd., Beijing (CN)

(72) Inventors: Yuelei Shen, Beijing (CN); Jiawei Yao, Beijing (CN); Chaoshe Guo, Beijing (CN); Yanan Guo, Beijing (CN); Yang Bai, Beijing (CN); Rui Huang, Beijing (CN); Lei Zhao, Beijing (CN); Meiling Zhang, Beijing (CN)

(73) Assignee: Biocytogen Pharmaceuticals (Beijing) Co., Ltd., Beijing (CN)

( * ) Notice: Subject to any disclaimer, the term of this patent is extended or adjusted under 35 U.S.C. 154(b) by 0 days.

(21) Appl. No.: 17/009,410

(22) Filed: Sep. 1, 2020

(65) Prior Publication Data

US 2021/0045366 A1    Feb. 18, 2021

Related U.S. Application Data

(63) Continuation of application No. PCT/CN2019/127084, filed on Dec. 20, 2019.

(30) Foreign Application Priority Data

Dec. 20, 2018 (CN) .......................... 201811560733.5

(51) Int. Cl.
| | | |
|---|---|---|
| *A01K 67/027* | (2006.01) | |
| *C12N 15/85* | (2006.01) | |
| *A61K 49/00* | (2006.01) | |
| *C07K 14/705* | (2006.01) | |

(52) U.S. Cl.
CPC ...... *A01K 67/0278* (2013.01); *A61K 49/0008* (2013.01); *C07K 14/70503* (2013.01); *A01K 2217/072* (2013.01); *A01K 2217/075* (2013.01); *A01K 2217/077* (2013.01); *A01K 2227/105* (2013.01); *A01K 2267/0331* (2013.01)

(58) Field of Classification Search
None
See application file for complete search history.

(56) References Cited

U.S. PATENT DOCUMENTS

| 4,683,195 | A | 7/1987 | Mullis et al. |
|---|---|---|---|
| 10,306,874 | B2 | 6/2019 | Mujica |
| 10,925,264 | B2 | 2/2021 | Shen et al. |
| 2015/0106961 | A1 | 4/2015 | Rojas et al. |
| 2017/0142943 | A1 | 5/2017 | Mujica |
| 2019/0364860 | A1 | 12/2019 | Shen |
| 2021/0015937 | A1* | 1/2021 | Edwards ............. A61P 35/00 |

FOREIGN PATENT DOCUMENTS

| CN | 104561095 | 4/2015 |
|---|---|---|
| CN | 108070613 | 5/2018 |
| WO | WO 2004078928 | 9/2004 |
| WO | WO 2017087780 | 5/2017 |
| WO | WO 2018001241 | 1/2018 |
| WO | WO 2018041119 | 3/2018 |
| WO | WO 2018041120 | 3/2018 |
| WO | WO 2018041121 | 3/2018 |
| WO | WO2018058111 | * 3/2018 |
| WO | WO 2018068756 | 4/2018 |
| WO | WO 2018086583 | 5/2018 |
| WO | WO 2018086594 | 5/2018 |
| WO | WO 2018113774 | 6/2018 |
| WO | WO 2018121787 | 7/2018 |
| WO | WO 2018177440 | 10/2018 |
| WO | WO 2018177441 | 10/2018 |
| WO | WO 2018041118 | 3/2019 |

OTHER PUBLICATIONS

Munoz et al. (2008, Theriogenology, vol. 69, pp. 1159-1164.*
Petitte et al. (2004, Mech. of Develop., vol. 121, pp. 1159-1168.*
Lavial et al. (2010, Develop. Growth Diff., vol. 52, pp. 101-114.*
Wayne's Word Gee-Whiz Trivia For Feb. 1998; pp. 1-19.*
Miao et al., 2012; review Edited by Dr Patricia Hernandez-Rodriguez, pp. 255-282.*
Brevini et al., 2010, Theriogenology, vol. 74, pp. 544-550.*
Paris et al. (2010, Theriogenology, vol. 74, pp. 516-524.*
Vertebrate—Wikipedia; last visited Aug. 27, 2019; pp. 1-10.*
SCORE—View Sequence Detail(s) for U.S. Appl. No. 16/409,683; Apr. 2, 2021. pp. 1-3 Seq ID No. 31.*
Ngo, in The Protein Folding Problem and Tertiary Structure Prediction, Merz et al. (eds.), Birkhauser Boston: Boston, MA, pp. 433 and 492-495, 1994.*
Rudinger (in Peptide Hormones, Parsons (ed.), University Park Press: Baltimore, MD, pp. 1-7, 1976.*
Auerbach et al., "Establishment and Chimera Analysis of 129/SvEv- and C57BL/6-Derived Mouse Embiyonic Stem Cell Lines," BioTechniques, 2000, 29:1024-1032.
Burova et al., "Combined treatment with anti-LAG-3 and anti-PD-1 fully human monoclonal antibodies inhibits tumor growth and immunocompetent double humanized LAG-3/PD-1 mice," Cancer Research, 2016, 76(14):1484, abstract.
Burugu et al., "Emerging targets in cancer immunotherapy." Seminars in Cancer Biology, Academic Press, 2017, 52(2):39-52.
Festing et al., "Revised nomenclature for strain 129 mice," Mammalian Genome, 1999, 10(8):836.
GenBank Accession No. X51985.3, "Human LAG-3 mRNA for CD4-related protein involved in lymphocyte activation," GenBank, Feb. 26, 1990, 2 pages.

(Continued)

*Primary Examiner* — Maria G Leavitt
(74) *Attorney, Agent, or Firm* — Fish & Richardson P.C.

(57) ABSTRACT

The present disclosure relates to genetically modified non-human animals that express a human or chimeric (e.g., humanized) LAG3, and methods of use thereof.

15 Claims, 32 Drawing Sheets

Specification includes a Sequence Listing.

(56) References Cited

OTHER PUBLICATIONS

GenBank accession No. NM_008479.2, "Mus musculus lymphocyte-activation gene 3 (Lag3), mRNA," May 2, 2019, 5 pages.

GenBank accession: NP_032506, "Laminin subunit alpha-1 precursor [Mus musculus]," Mar. 19, 2019, 9 pages.

Hemon et al. "MHC class II engagement by its ligand LAG-3 (CD223) contributes to melanoma resistance to apoptosis." The Journal of Immunology, 2011, 186(9):5173-5183.

Huard et al., "Characterization of the major histocompatibility complex class II binding site on LAG-3 protein," Proc. Natl. Acad. Sci. USA, 1997, 94:5744-5749.

International Search Report and Written Opinion in Appln. No. PCT/CN2017/110435, dated Feb. 9, 2018, 14 pages.

International Search Report and Written Opinion in Appln. No. PCT/CN2019/127084, dated Mar. 20, 2020, 10 pages.

Ito et al., "NOD/SCID/ γcnull mouse: an excellent recipient mouse model for engraftment of human cells," Blood, 2002, 100(9):3175-3182.

Joller et al., "Tim-3, Lag-3, and TIGIT," Curr. Top Microbiol. Immunol., 2017, 410:127-156.

Puhr et al. "New emerging targets in cancer immunotherapy: the role of LAG3." ESMO Open, 2019, 4(2):e000482.

Scherer et al., "NCBI reference sequence: NC_000012.12," GenBank, Mar. 26, 2018, 3 pages.

Solinas et al. "LAG3: The biological processes that motivate targeting this immune checkpoint molecule in human cancer." Cancers, 2019, 11(8):1213.

Wang et al., "NCBI reference sequence: NP_002277.4," GenPept, Nov. 23, 2018, 4 pages.

Workman et al., "The CD4—related molecule, LAG-3 (CD223), regulates the expansion of activated T cells," Europeans journal of immunology, 2003, 33(4):970-979.

Andrews et al., "LAG 3 (CD 223) as a cancer immunotherapy target," Immunological reviews, Mar. 2017, 276(1):80-96.

Zhang Xiaolian, "New progress in immunology and experimental technology," China Medical Electronic Audiovisual Press, p. 252 (with English translation).

Maruhashi et al., "LAG-3: from molecular functions to clinical applications," Journal for Immunotherapy of Cancer, 2020, 8(2):1-9.

Zhu et al., "Humanising the mouse genome piece by piece," Nature communications, Apr. 23, 2019, 10(1):1-13.

International Preliminary Report on Patentability in International Application No. PCT/CN2017/110435, dated May 23, 2019, 9 pages.

International Preliminary Report on Patentability in International Application No. PCT/CN2019/127084, dated Jul. 1, 2021, 6 pages.

\* cited by examiner

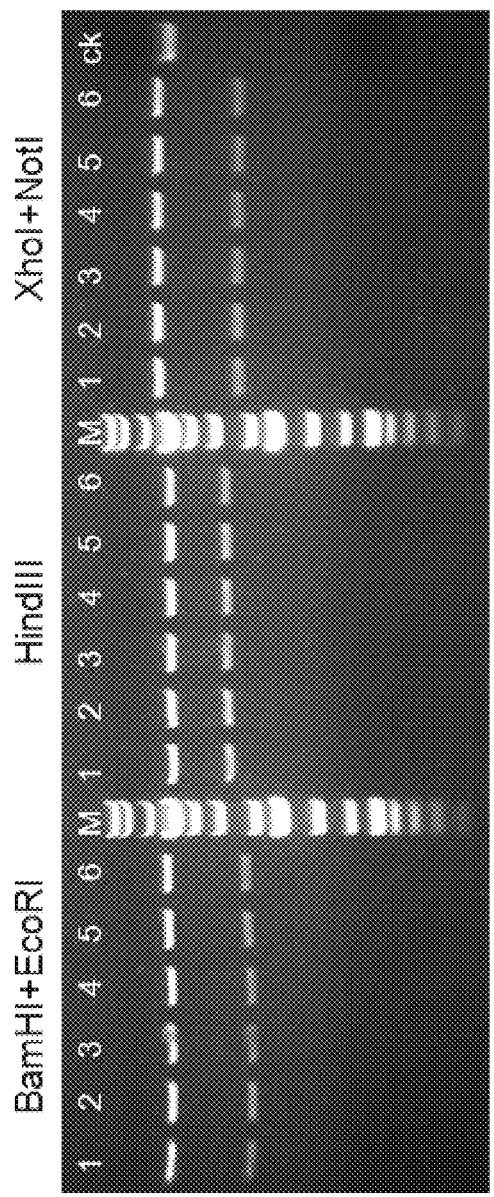
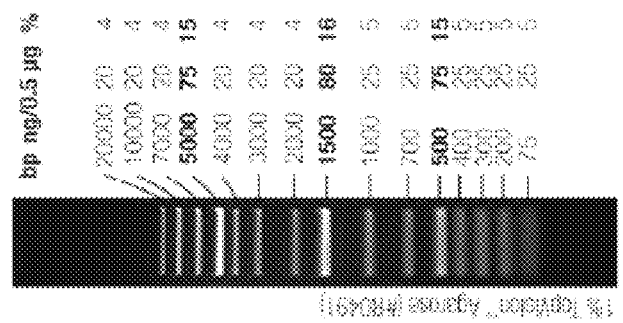
FIGS. 9A
FIGS. 9B

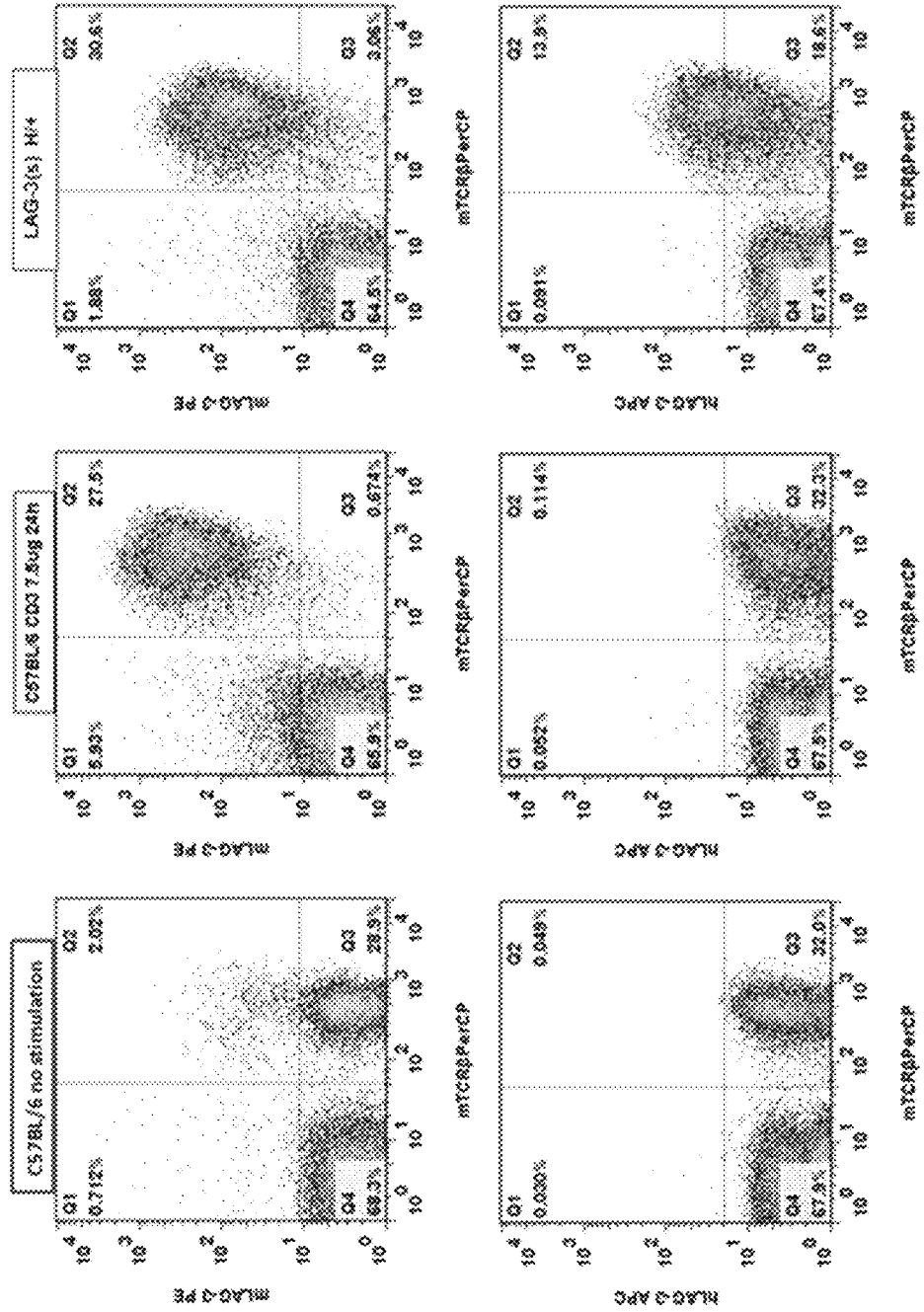

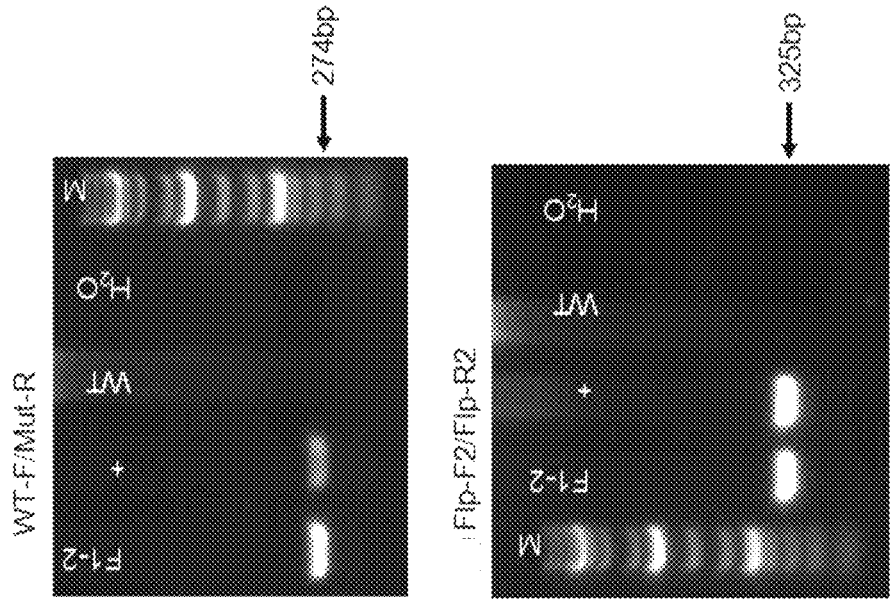
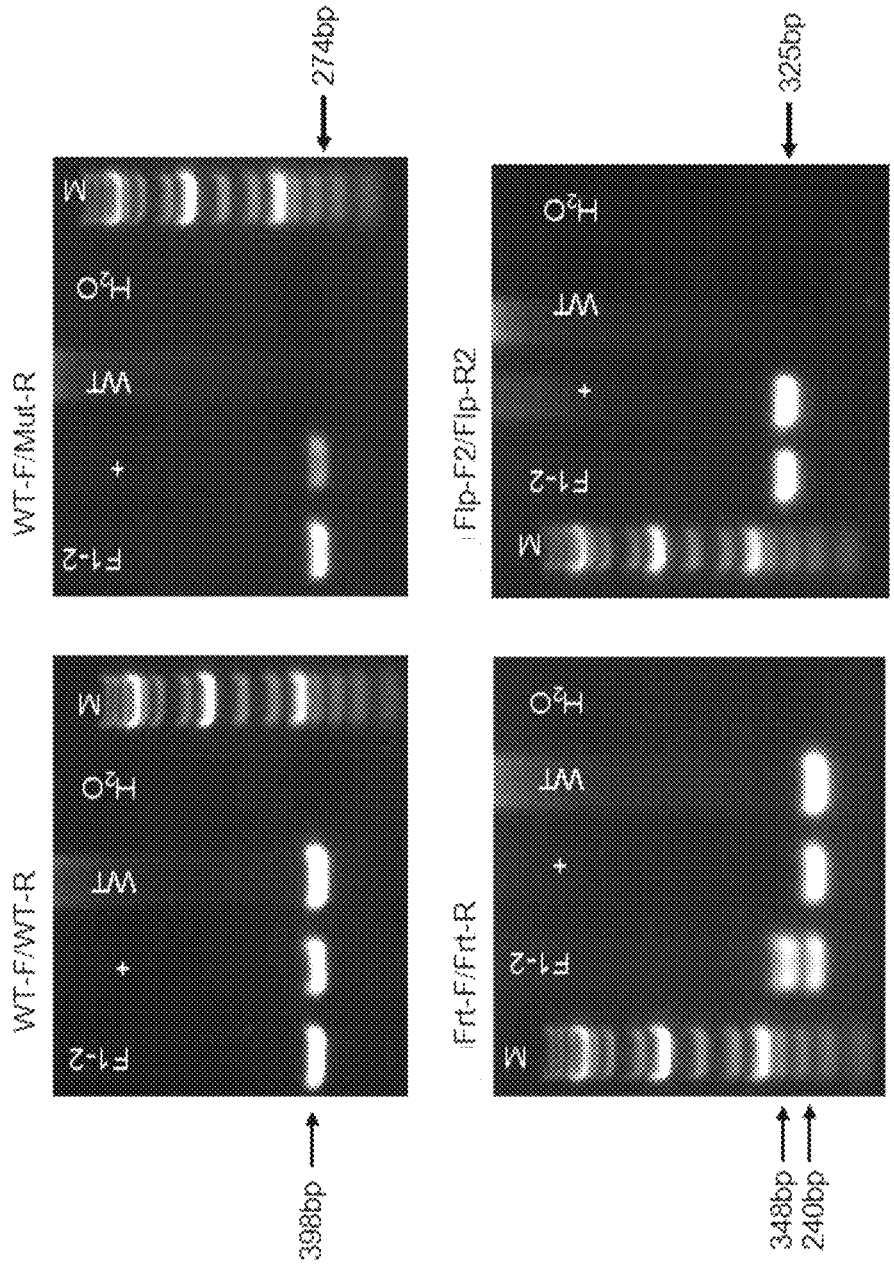
FIG. 20A  FIG. 20B  FIG. 20C  FIG. 20D

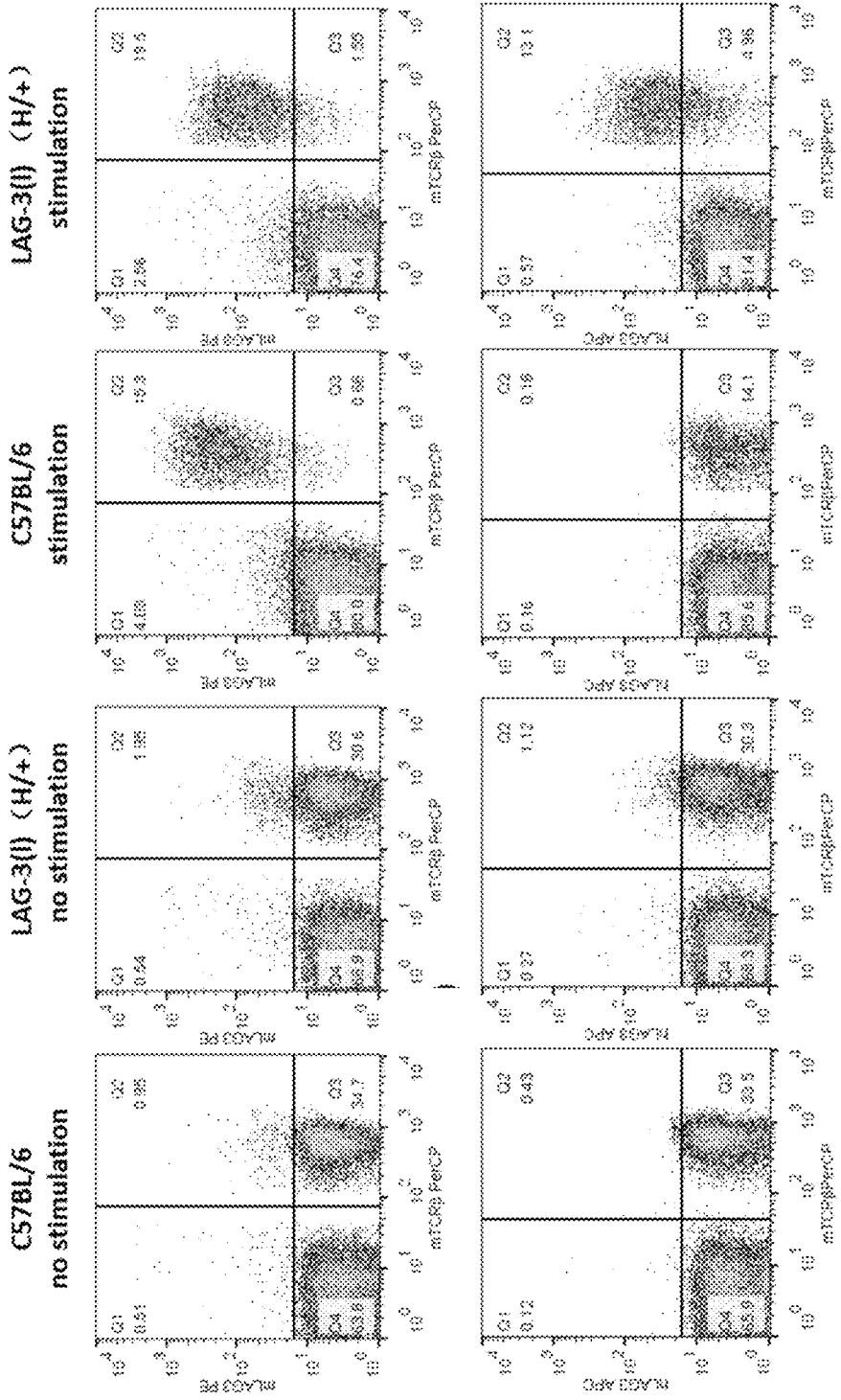

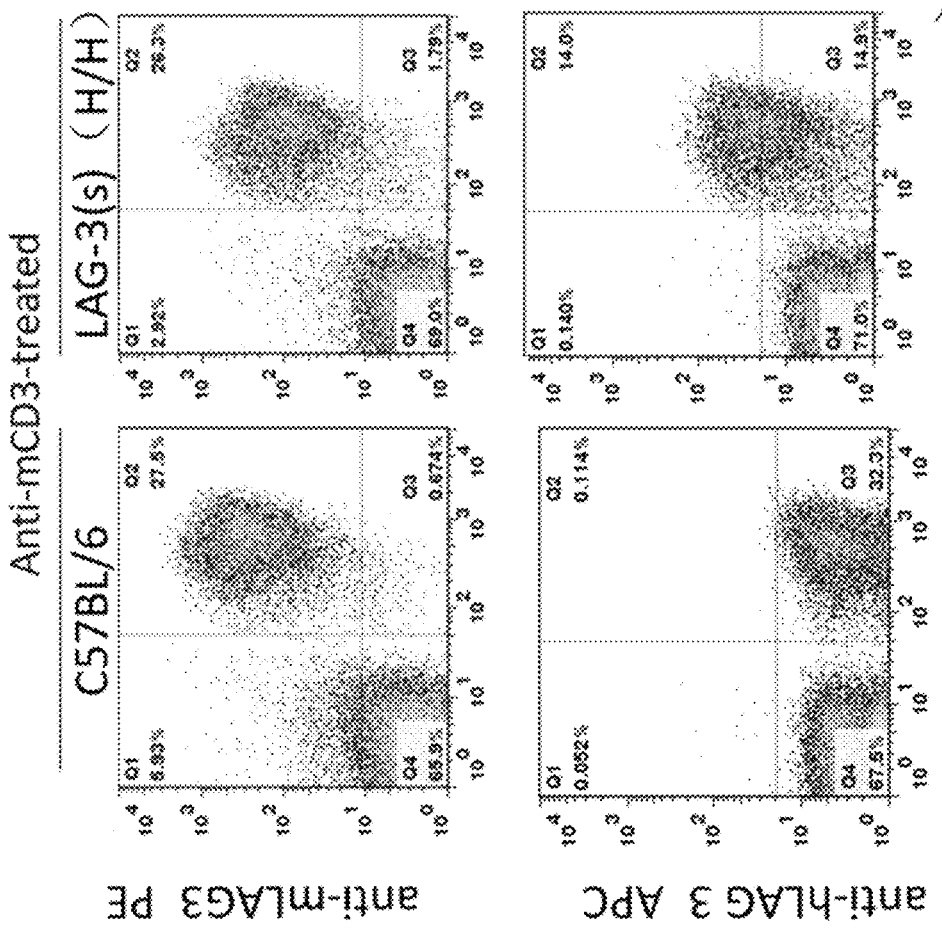

FIG. 32

| Score | Expect | Method | Identities | Positives | Gaps |
|---|---|---|---|---|---|
| 613 bits(1580) | 0.0 | Compositional matrix adjust. | 344/499(69%) | 369/499(73%) | 8/499(1%) |

```
MOUSE   1    MREDLLLGFLLLGLLWEAPVVSSGPGKELPVVWAQEGAPVHLPCSLKSPNLDPNFLRRGG    60
             M E    LG L L  LW APV    PG E+PVVWAQEGAP  LPCS  P  D + LRR G
HUMAN   1    MWEAQFLGLLFLQPLWVAPVKPLQPGAEVPVVWAQEGAPAQLPCSPTIPLQDLSLLRRAG    60

MOUSE   61   VIWQHQPDSGQPTIPIALDL------HQGMPSPRQPAPGRYTVLSVAPGGLRSGRQPLHPHV   116
             V WQHQPDSG  P  L   H    PS     P P RYTVLSV PGGLRSGR PL P V
HUMAN   61   VTWQHQPDSGPPAAAPGHPLAPGPHPAAPSSWGPRPRRYTVLSVPGGLRSGRLPLQPRV    120

MOUSE   117  QLEERGLQRGDFSLWMLRPALRTDAGEYHATVRLPNRALSCSLRLRVGQASMIASPSGVLK    176
             QL+ERG QRGDFSLWMLRPA R DAGEY A V L +RALSC LRLR+GQASM ASP G L+
HUMAN   121  QLDERGRQRGDFSLWMLRPARRADAGEYRAAVHLRDRALSCRLRLRLGQASMTASPPGSLR    180

MOUSE   177  LSDWVLLNCSFSRPDRPVSVHWFQ--GQNRVPVYNSPRHFLAETFLLLPQVSPLDSGTWG    234
             SDWV+LNCSFSRPDRP SVHWF+    GQ RVPV  SP H  LAE+FL  LPQVSP+DSG WG
HUMAN   181  ASDWVILNCSFSRPDRPASVHWFRNRGQGRVPVRESPHHHLAESFLFLPQVSPMDSGPWG    240

MOUSE   235  CVLTYRDGFNVSITYNLKVLGLEPVAPLTVYAAEGSRVELPCHLPPGVGTPSLLIAKWTP    294
             C+LTYRDGFNVSI YNL VLGLEP PLTVYA   GSRV LPC LP GVGT S L AKWTP
HUMAN   241  CILTYRDGFNVSIMYNLTVLGLEPPTPLTVYAGAGSRVGLPCRLPAGVGTRSFLTAKWTP    300
```

FIG. 32 (Continued)

```
MOUSE 295  PGGGPELPVAGKSGNFTLHLEAVGLAQAGTYTCSIHLQGQQLNATVTLAVITVTPKSFGL  354
           PGGGP+L V G +G+FTL LE V  AQAGTYTC IHLQ QQLNATVTLA+ITVTPKSFG
HUMAN 301  PGGGPDLLVTGDNGDFTLRLEDVSQAQAGTYTCHIHLQEQQLNATVTLAIITVTPKSFGS  360

MOUSE 355  PGSRGKLLCEVTPASGKERFVWRPLNNLS-RSCPGPVLEIQEARLLAERWQCQLYEGQRL  413
           PGS GKLLCEVTP  SG+ERFVW  L+  S RS  GP LE  QEA+LL++ WQCQLY+G+RL
HUMAN 361  PGSLGKLLCEVTPVSGQERFVWSSLDTPSQRSFSGPWLEAQEAQLLSQPWQCQLYQGERL  420

MOUSE 414  LGATVYAAE-SSSGAHSARRISGDLKGGHLVLVLIIGALSLFLLVAGAFGFHWWRKQLLL  472
           LGA VY  E SS GA  + R  G L  GHL+L LILG LSL LLV GAFGFH WR+Q
HUMAN 421  LGAAVYFTELSSPGAQRSGRAPGALPAGHLLLFLILGVLSLLLLVTGAFGFHLWRRQWRP  480

MOUSE 473  RRFSALEHGIQPFPAQRKI  491
           RRFSALE GI P  AQ KI
HUMAN 481  RRFSALEQGIHPPQAQSKI  499
```

GENETICALLY MODIFIED NON-HUMAN ANIMAL WITH HUMAN OR CHIMERIC LAG3

CLAIM OF PRIORITY

Pursuant to 35 U.S.C. § 119(e), this application is a continuation of International Application PCT/CN2019/127084, with an international filing date of Dec. 20, 2019, which claims the benefit of Chinese Patent Application App. No. 201811560733.5, filed on Dec. 20, 2018. The entire contents of the foregoing are incorporated herein by reference.

TECHNICAL FIELD

This disclosure relates to genetically modified animal expressing human or chimeric (e.g., humanized) LAG3, and methods of use thereof.

BACKGROUND

The immune system has developed multiple mechanisms to prevent deleterious activation of immune cells. One such mechanism is the intricate balance between positive and negative costimulatory signals delivered to immune cells. Targeting the stimulatory or inhibitory pathways for the immune system is considered to be a potential approach for the treatment of various diseases, e.g., cancers and autoimmune diseases.

The traditional drug research and development for these stimulatory or inhibitory receptors typically use in vitro screening approaches. However, these screening approaches cannot provide the body environment (such as tumor microenvironment, stromal cells, extracellular matrix components and immune cell interaction, etc.), resulting in a higher rate of failure in drug development. In addition, in view of the differences between humans and animals, the test results obtained from the use of conventional experimental animals for in vivo pharmacological test may not reflect the real disease state and the interaction at the targeting sites, resulting in that the results in many clinical trials are significantly different from the animal experimental results. Therefore, the development of humanized animal models that are suitable for human antibody screening and evaluation will significantly improve the efficiency of new drug development and reduce the cost for drug research and development.

SUMMARY

This disclosure is related to an animal model with human LAG3 or chimeric LAG3. The animal model can express human LAG3 or chimeric LAG3 (e.g., humanized LAG3) protein in its body. It can be used in the studies on the function of LAG3 gene, and can be used in the screening and evaluation of anti-human LAG3 antibodies. In addition, the animal models prepared by the methods described herein can be used in drug screening, pharmacodynamics studies, treatments for immune-related diseases (e.g., autoimmune disease), and cancer therapy for human LAG3 target sites; they can also be used to facilitate the development and design of new drugs, and save time and cost. In summary, this disclosure provides a powerful tool for studying the function of LAG3 protein and a platform for screening cancer drugs.

In one aspect, the disclosure relates to a genetically-modified, non-human animal whose genome comprises at least one chromosome comprising a sequence encoding a human or chimeric LAG3.

In some embodiments, the sequence encoding the human or chimeric LAG3 is operably linked to an endogenous regulatory element at the endogenous LAG3 gene locus in the at least one chromosome.

In some embodiments, the sequence encoding a human or chimeric LAG3 comprises a sequence encoding an amino acid sequence that is at least 70%, 75%, 80%, 85%, 90%, 95%, 99%, or 100% identical to human LAG3 (NP_002277.4 (SEQ ID NO: 4)).

In some embodiments, the sequence encoding a human or chimeric LAG3 comprises a sequence encoding an amino acid sequence that is at least 70%, 75%, 80%, 85%, 90%, 95%, 99%, or 100% identical to SEQ ID NO: 9 or 44.

In some embodiments, the sequence encoding a human or chimeric LAG3 comprises a sequence that is at least 70%, 75%, 80%, 85%, 90%, 95%, 99%, or 100% identical to amino acids 25-258 of SEQ ID NO: 4. In some embodiments, the sequence encoding a human or chimeric LAG3 comprises a sequence that is at least 70%, 75%, 80%, 85%, 90%, 95%, 99%, or 100% identical to amino acids 25-465 of SEQ ID NO: 4.

In some embodiments, the animal is a mammal, e.g., a monkey, a rodent, a rat, or a mouse. In some embodiments, the animal is a mouse. In some embodiments, the animal does not express endogenous LAG3, or expresses a decreased level of endogenous LAG3.

In some embodiments, the animal has one or more cells expressing human or chimeric LAG3. In some embodiments, the animal has one or more cells expressing human or chimeric LAG3, and human MHC class II molecules or Fibrinogen-like protein1 (FGL1) can bind to the expressed human or chimeric LAG3. In some embodiments, the animal has one or more cells expressing human or chimeric LAG3, and endogenous MHC class II molecules or FGL1 can bind to the expressed human or chimeric LAG3.

In one aspect, the disclosure relates to a genetically-modified, non-human animal, wherein the genome of the animal comprises a replacement of a sequence encoding a region of endogenous LAG3 with a sequence encoding a corresponding region of human LAG3 at an endogenous LAG3 gene locus.

In some embodiments, the sequence encoding the corresponding region of human LAG3 is operably linked to an endogenous regulatory element at the endogenous LAG3 locus, and one or more cells of the animal expresses a chimeric LAG3.

In some embodiments, the animal does not express endogenous LAG3 or expresses a decreased level of endogenous LAG3.

In some embodiments, the replaced locus is the extracellular region of LAG3 and/or the transmembrane region of LAG3.

In some embodiments, the animal has one or more cells expressing a chimeric LAG3 having an extracellular region, a transmembrane region, and a cytoplasmic region, In some embodiments, the extracellular region comprises a sequence that is at least 50%, 60%, 70%, 80%, 90%, 95%, or 99% identical to the extracellular or transmembrane region of human LAG3.

In some embodiments, the extracellular region of the chimeric LAG3 has a sequence that has at least 10, 20, 30, 40, 50, 60, 70, 80, 90, 100, 150, 200, 250, 300, 350, or 400 contiguous amino acids that are identical to a contiguous sequence present in the extracellular or transmembrane region of human LAG3.

In some embodiments, the animal is a mouse, and the replaced region of endogenous LAG3 is exon 2, exon 3, exon 4, exon 5, exon 6, and/or exon 7 or part thereof of the endogenous mouse LAG3 gene.

In some embodiments, the animal is a mouse, and the replaced region of endogenous LAG3 is exon 2, exon 3, and/or exon 4 or part thereof of the endogenous mouse LAG3 gene.

In some embodiments, the animal is heterozygous with respect to the replacement at the endogenous LAG3 gene locus. In some embodiments, the animal is homozygous with respect to the replacement at the endogenous LAG3 gene locus.

In one aspect, the disclosure relates to a method for making a genetically-modified, non-human animal, comprising: replacing in at least one cell of the animal, at an endogenous LAG3 gene locus, a sequence encoding a region of an endogenous LAG3 with a sequence encoding a corresponding region of human LAG3.

In some embodiments, the sequence encoding the corresponding region of human LAG3 comprises exon 1, exon 2, exon 3, exon 4, exon 5, exon 6, exon 7, and/or exon 8, or a part thereof of a human LAG3 gene.

In some embodiments, the sequence encoding the corresponding region of LAG3 comprises exon 2, exon 3, exon 4, exon 5, exon 6, and/or exon 7, or a part thereof, of a human LAG3 gene. In some embodiments, the sequence encoding the corresponding region of LAG3 comprises exon 2, exon 3, and/or exon 4, or a part thereof, of a human LAG3 gene.

In some embodiments, the sequence encoding the corresponding region of human LAG3 encodes amino acids 25-258 of SEQ ID NO: 4. In some embodiments, the sequence encoding the corresponding region of human LAG3 encodes amino acids 25-465 of SEQ ID NO: 4.

In some embodiments, the region is the extracellular region of LAG3. In some embodiments, the region is the transmembrane region of LAG3. In some embodiments, the animal is a mouse, and the mouse comprises a sequence that is at least 50%, 60%, 70%, 80%, 90%, 95%, or 99% identical to SEQ ID NO: 7, SEQ ID NO: 8, SEQ ID NO: 68, SEQ ID NO: 69, SEQ ID NO: 70, or SEQ ID NO: 71. In some embodiments, the animal is a mouse, and the mouse comprises a sequence that is at least 50%, 60%, 70%, 80%, 90%, 95%, or 99% identical to SEQ ID NO: 42, SEQ ID NO: 43, SEQ ID NO: 67, SEQ ID NO: 45, or SEQ ID NO: 46.

In one aspect, the disclosure relates to a non-human animal comprising at least one cell comprising a nucleotide sequence encoding a chimeric LAG3 polypeptide, In some embodiments, the chimeric LAG3 polypeptide comprises at least 50, 100, 150, 200, 250, 300, 350, or 400 contiguous amino acid residues that are identical to the corresponding contiguous amino acid sequence of a human LAG3. In some embodiments, the animal expresses the chimeric LAG3.

In some embodiments, the chimeric LAG3 polypeptide has at least 50 contiguous amino acid residues that are identical to the corresponding contiguous amino acid sequence of a human LAG3 extracellular region.

In some embodiments, the chimeric LAG3 polypeptide comprises a sequence that is at least 90%, 95%, or 99% identical to amino acids 25-258 of SEQ ID NO: 4.

In some embodiments, the chimeric LAG3 polypeptide comprises a sequence that is at least 90%, 95%, or 99% identical to amino acids 25-465 of SEQ ID NO: 4.

In some embodiments, the nucleotide sequence is operably linked to an endogenous LAG3 regulatory element of the animal.

In some embodiments, the chimeric LAG3 polypeptide comprises an endogenous LAG3 extracellular region and/or an endogenous LAG3 transmembrane region.

In some embodiments, the nucleotide sequence is integrated to an endogenous LAG3 gene locus of the animal.

In some embodiments, the chimeric LAG3 polypeptide comprises a mouse signal polypeptide; a chimeric or human LAG3 extracellular region; a chimeric or endogenous LAG3 transmembrane region; and an endogenous LAG3 cytoplasmic region.

In one aspect, the disclosure relates to a method of making a genetically-modified mouse cell that expresses a chimeric LAG3, the method comprising: replacing at an endogenous mouse LAG3 gene locus, a nucleotide sequence encoding a region of mouse LAG3 with a nucleotide sequence encoding a corresponding region of human LAG3, thereby generating a genetically-modified mouse cell that includes a nucleotide sequence that encodes the chimeric LAG3. In some embodiments, the mouse cell expresses the chimeric LAG3.

In some embodiments, the chimeric LAG3 comprises: a mouse signal polypeptide; a chimeric or human LAG3 extracellular region; an endogenous LAG3 transmembrane region; and an endogenous LAG3 cytoplasmic region.

In some embodiments, the chimeric LAG3 comprises: a mouse signal polypeptide; a chimeric or human LAG3 extracellular region; a chimeric LAG3 transmembrane region; and an endogenous LAG3 cytoplasmic region.

In some embodiments, the nucleotide sequence encoding the chimeric LAG3 is operably linked to an endogenous LAG3 regulatory region, e.g., promoter.

In some embodiments, the animal further comprises a sequence encoding an additional human or chimeric protein. In some embodiments, the additional human or chimeric protein is programmed cell death protein 1 (PD-1), cytotoxic T-lymphocyte-associated protein 4 (CTLA-4), B And T Lymphocyte Associated (BTLA), Programmed Cell Death 1 Ligand 1 (PD-L1), CD27, CD28, CD40, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), Signal regulatory protein α (SIRPα) or TNF Receptor Superfamily Member 4 (OX40).

In one aspect, the disclosure relates to a method of determining effectiveness of an anti-LAG3 antibody for the treatment of cancer, comprising: administering the anti-LAG3 antibody to the animal as described herein, wherein the animal has a tumor; and determining the inhibitory effects of the anti-LAG3 antibody to the tumor.

In some embodiments, the tumor comprises one or more cells that express LAG3. In some embodiments, the animal comprises one or more cells (e.g., immune cells, T cells, natural killer cells, B cells, and/or dendritic cells) that express LAG3. In some embodiments, the tumor comprises one or more cancer cells that are injected into the animal. In some embodiments, determining the inhibitory effects of the anti-LAG3 antibody to the tumor involves measuring the tumor volume in the animal. In some embodiments, the tumor cells are melanoma cells, pancreatic carcinoma cells, mesothelioma cells, or solid tumor cells.

In one aspect, the disclosure relates to a method of determining effectiveness of an anti-LAG3 antibody and an additional therapeutic agent for the treatment of a tumor, comprising administering the anti-LAG3 antibody and the additional therapeutic agent to the animal as described herein, wherein the animal has a tumor; and determining the inhibitory effects on the tumor. In some embodiments, the animal further comprises a sequence encoding a human or chimeric programmed cell death protein 1 (PD-1). In some embodiments, the animal further comprises a sequence encoding a human or chimeric programmed death-ligand 1 (PD-L1). In some embodiments, the additional therapeutic agent is an anti-PD-1 antibody or an anti-PD-L1 antibody. In some embodiments, the tumor comprises one or more tumor cells that express PD-L1 or PD-L2.

In some embodiments, the tumor is caused by injection of one or more cancer cells into the animal. In some embodiments, determining the inhibitory effects of the treatment involves measuring the tumor volume in the animal.

In some embodiments, the animal has melanoma cells, pancreatic carcinoma cells, mesothelioma cells, or solid tumor cells.

In one aspect, the disclosure relates to a protein comprising an amino acid sequence, wherein the amino acid sequence is one of the following:

(a) an amino acid sequence set forth in SEQ ID NO: 9 or SEQ ID NO: 44;

(b) an amino acid sequence that is at least 90% identical to SEQ ID NO: 9 or SEQ ID NO: 44;

(c) an amino acid sequence that is at least 91%, 92%, 93%, 94%, 95%, 96%, 97%, 98%, or 99% identical to SEQ ID NO: 9 or SEQ ID NO: 44;

(d) an amino acid sequence that is different from the amino acid sequence set forth in SEQ ID NO: 9 or SEQ ID NO: 44, by no more than 10, 9, 8, 7, 6, 5, 4, 3, 2 or 1 amino acid; and (e) an amino acid sequence that comprises a substitution, a deletion and/or insertion of one, two, three, four, five or more amino acids to the amino acid sequence set forth in SEQ ID NO: 9 or SEQ ID NO: 44.

In one aspect, the disclosure relates to a nucleic acid comprising a nucleotide sequence, wherein the nucleotide sequence is one of the following:

(a) a sequence that encodes the protein as described herein;

(b) SEQ ID NO: 7, 8, 68, 69, 70, or 71;

(c) SEQ ID NO: 42, 43, 45, 46, or 67;

(d) a sequence that is at least 90%, 91%, 92%, 93%, 94%, 95%, 96%, 97%, 98%, or 99% identical to SEQ ID NO: 7, 8, 68, 69, 70, or 71; and (e) a sequence that is at least 91%, 92%, 93%, 94%, 95%, 96%, 97%, 98%, or 99% identical to SEQ ID NO: 42, 43, 45, 46, or 67.

In one aspect, the disclosure relates to a cell comprising the protein as described herein and/or the nucleic acid protein as described herein.

In one aspect, the disclosure relates to an animal comprising the protein as described herein and/or the nucleic acid protein as described herein.

In another aspect, the disclosure also provides a genetically-modified, non-human animal whose genome comprise a disruption in the animal's endogenous LAG3 gene, wherein the disruption of the endogenous LAG3 gene comprises deletion of exon 1, exon 2, exon 3, exon 4, exon 5, exon 6, exon 7, and/or exon 8 or part thereof of the endogenous LAG3 gene.

In some embodiments, the disruption of the endogenous LAG3 gene comprises deletion of one or more exons or part of exons selected from the group consisting of exon 1, exon 2, exon 3, exon 4, exon 5, exon 6, exon 7, and exon 8 of the endogenous LAG3 gene.

In some embodiments, the disruption of the endogenous LAG3 gene further comprises deletion of one or more introns or part of introns selected from the group consisting of intron 1, intron 2, intron 3, intron 4, intron 5, intron 6, and intron 7 of the endogenous LAG3 gene.

In some embodiments, wherein the deletion can comprise deleting at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, 300, 350, 400, 450, 500, 550, 600, 650, or more nucleotides.

In some embodiments, the disruption of the endogenous LAG3 gene comprises the deletion of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 10, 220, 230, 240, 250, 260, 270, 280, 290, or 300 nucleotides of exon 1, exon 2, exon 3, exon 4, exon 5, exon 6, exon 7, and/or exon 8 (e.g., deletion of at least 10, 20, 30, 40, or 50 nucleotides of exon 2, exon 4, or exon 7).

In some embodiments, the disruption of the endogenous LAG3 gene comprises the deletion of a part of exon 2, intron 2, exon 3, intron 3, and/or a part of exon 4.

In some embodiments, the disruption of the endogenous LAG3 gene comprises the deletion of a part of exon 2, intron 2, exon 3, intron 3, exon 4, intron 4, exon 5, intron 5, exon 6, intron 6, and/or a part of exon 7.

In some embodiments, the mice described in the present disclosure can be mated with the mice containing other human or chimeric genes (e.g., chimeric SIRPa, chimeric PD-1, chimeric PD-L1, chimeric CTLA-4, or other immunomodulatory factors), so as to obtain a mouse expressing two or more human or chimeric proteins. The mice can also, e.g., be used for screening antibodies in the case of a combined use of drugs, as well as evaluating the efficacy of the combination therapy.

In another aspect, the disclosure further provides methods of determining toxicity of an agent (e.g., a LAG3 antagonist or agonist). The methods involve administering the agent to the animal as described herein; and determining weight change of the animal. In some embodiments, the method further involve performing a blood test (e.g., determining red blood cell count).

The disclosure also relates to a method for establishing a genetically-modified non-human animal expressing two human or chimeric (e.g., humanized) genes. The method includes the steps of (a) using the method for establishing a LAG3 gene humanized animal model to obtain a LAG3 gene genetically modified humanized mouse;

(b) mating the LAG3 gene genetically modified humanized mouse obtained in step (a) with another humanized mouse, and then screening to obtain a double humanized mouse model.

In some embodiments, in step (b), the LAG3 gene genetically modified humanized mouse obtained in step (a) is mated with a PD-1 or PD-L1 humanized mouse to obtain a LAG3 and PD-1 double humanized mouse model or a LAG3 and PD-L1 double humanized mouse model.

The disclosure also relates to non-human mammal generated through the methods as described herein.

In some embodiments, the genome thereof contains human gene(s).

In some embodiments, the non-human mammal is a rodent. In some embodiments, the non-human mammal is a mouse.

In some embodiments, the non-human mammal expresses a protein encoded by a humanized LAG3 gene.

The disclosure also relates to an offspring of the non-human mammal.

In another aspect, the disclosure relates to a tumor bearing non-human mammal model, characterized in that the non-human mammal model is obtained through the methods as described herein.

In some embodiments, the non-human mammal is a rodent. In some embodiments, the non-human mammal is a mouse.

The disclosure also relates to a cell (e.g., stem cell or embryonic stem cell) or cell line, or a primary cell culture thereof derived from the non-human mammal or an offspring thereof, or the tumor bearing non-human mammal.

The disclosure further relates to the tissue, organ or a culture thereof derived from the non-human mammal or an offspring thereof, or the tumor bearing non-human mammal.

In another aspect, the disclosure relates to a tumor tissue derived from the non-human mammal or an offspring thereof when it bears a tumor, or the tumor bearing non-human mammal.

In one aspect, the disclosure relates to a LAG3 amino acid sequence of a humanized mouse, wherein the amino acid sequence is selected from the group consisting of:

a) an amino acid sequence shown in SEQ ID NO: 9 or SEQ ID NO: 44;

b) an amino acid sequence having a homology of at least 90% with the amino acid sequence shown in SEQ ID NO: 9 or SEQ ID NO: 44;

c) an amino acid sequence encoded by a nucleic acid sequence, wherein the nucleic acid sequence is able to hybridize to a nucleotide sequence encoding the amino acid shown in SEQ ID NO: 9 or SEQ ID NO: 44 under a low stringency condition or a strict stringency condition;

d) an amino acid sequence having a homology of at least 90%, 91%, 92%, 93%, 94%, 95%, 96%, 97%, 98%, or at least 99% with the amino acid sequence shown in SEQ ID NO: 9 or SEQ ID NO: 44;

e) an amino acid sequence that is different from the amino acid sequence shown in SEQ ID NO: 9 or SEQ ID NO: 44 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 9 or SEQ ID NO: 44.

The disclosure also relates to a LAG3 nucleic acid sequence of a humanized mouse, wherein the nucleic acid sequence is selected from the group consisting of:

a) a nucleic acid sequence that encodes the LAG3 amino acid sequence of a humanized mouse;

b) a nucleic acid sequence that is set forth in SEQ ID NO: 7, 8, 42, or 43;

c) a nucleic acid sequence that can hybridize to the nucleotide sequence as shown in SEQ ID NO: 7, 8, 42, or 43 under a low stringency condition or a strict stringency condition;

d) a nucleic acid sequence that has a homology of at least 90%, 91%, 92%, 93%, 94%, 95%, 96%, 97%, 98%, or at least 99% with the nucleotide sequence as shown in SEQ ID NO: 7, 8, 42, or 43;

f) a nucleic acid sequence that encodes an amino acid sequence, wherein the amino acid sequence has a homology of at least 90% with the amino acid sequence shown in SEQ ID NO: 9 or SEQ ID NO: 44;

g) a nucleic acid sequence that encodes an amino acid sequence, wherein the amino acid sequence has a homology of at least 90%, 91%, 92%, 93%, 94%, 95%, 96%, 97%, 98%, or at least 99% with the amino acid sequence shown in SEQ ID NO: 9 or SEQ ID NO: 44;

h) a nucleic acid sequence that encodes an amino acid sequence, wherein the amino acid sequence is different from the amino acid sequence shown in SEQ ID NO: 9 or SEQ ID NO: 44 by no more than 10, 9, 8, 7, 6, 5, 4, 3, 2 or no more than 1 amino acid; and/or i) a nucleic acid sequence that encodes an amino acid sequence, wherein the amino acid sequence comprises a substitution, a deletion and/or insertion of 1, 2, 3, 4, 5, 6, 7, 8, 9, or more amino acids to the amino acid sequence shown in SEQ ID NO: 9 or SEQ ID NO: 44.

The disclosure further relates to a LAG3 genomic DNA sequence of a humanized mouse, a DNA sequence obtained by a reverse transcription of the mRNA obtained by transcription thereof is consistent with or complementary to the DNA sequence; a construct expressing the amino acid sequence thereof; a cell comprising the construct thereof; a tissue comprising the cell thereof.

The disclosure further relates to the use of the non-human mammal or an offspring thereof, or the tumor bearing non-human mammal, the animal model generated through the method as described herein in the development of a product related to an immunization processes of human cells, the manufacture of a human antibody, or the model system for a research in pharmacology, immunology, microbiology and medicine.

The disclosure also relates to the use of the non-human mammal or an offspring thereof, or the tumor bearing non-human mammal, the animal model generated through the method as described herein in the production and utilization of an animal experimental disease model of an immunization processes involving human cells, the study on a pathogen, or the development of a new diagnostic strategy and/or a therapeutic strategy.

The disclosure further relates to the use of the non-human mammal or an offspring thereof, or the tumor bearing non-human mammal, the animal model generated through the methods as described herein, in the screening, verifying, evaluating or studying the LAG3 gene function, human LAG3 antibodies, the drugs or efficacies for human LAG3 targeting sites, and the drugs for immune-related diseases and antitumor drugs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 9A shows the restriction enzymes digestion results of the recombinant vector by three sets of restriction enzymes. Ck indicates undigested plasmids, which were used as a control. M is the Marker. No. 1-No. 6 are plasmid numbers.

FIG. 9B shows DNA ladder for the Marker.

FIG. 13A is a graph showing the flow cytometry analysis result to detect LAG3 protein expression in unstimulated wild-type C57BL/6 mice, wherein cells were stained by PE anti-mouse LAG3 antibody (mLAG3 PE) and PerCP/Cy5.5 anti-mouse TCR β chain (mTcRβ PerCP).

FIG. 13B is a graph showing the flow cytometry analysis result to detect LAG3 protein expression in anti-mouse CD3 antibody-stimulated wild-type C57BL/6 mice, wherein cells were stained by mLAG-3 PE and mTcRβ PerCP.

FIG. 13C is a graph showing the flow cytometry analysis result to detect LAG3 protein expression in anti-mouse CD3 antibody-stimulated LAG3(s) humanized heterozygous mice, wherein cells were stained by mLAG-3 PE and mTcRβ PerCP.

FIG. 13D is a graph showing the flow cytometry analysis result to detect LAG3 protein expression in wild-type C57BL/6 mice, wherein cells were stained by APC anti-hLAG3 antibody (hLAG3 APC) and mTcRβ PerCP.

FIG. 13E is a graph showing the flow cytometry analysis result to detect LAG3 protein expression in anti-mouse CD3 antibody-stimulated wild-type C57BL/6 mice, wherein cells were stained by hLAG-3 APC and mTcRβ PerCP.

FIG. 13F is a graph showing the flow cytometry analysis result to detect LAG3 protein expression in anti-mouse CD3 antibody-stimulated LAG3 (s) humanized heterozygous mice, wherein cells were stained by hLAG-3 APC and mTcRβ PerCP.

FIG. 20A shows PCR identification results of samples collected from tails of F1 generation mice. Primer pairs WT-F and WT-R were used for amplification of an exon 1-2 fragment of the wild-type LAG3 gene. WT is wild-type. $H_2O$ is a blank control, + is a positive control and M is the Marker.

FIG. 20B shows PCR identification results of samples collected from tails of F1 generation mice. Primer pairs WT-F and Mut-R were used for amplification of an exon 1-2 fragment of modified LAG3 gene, to verify the presence of the recombinant vector and correct insertion into the genomic site. WT is wild-type. $H_2O$ is a blank control, + is a positive control and M is the Marker.

FIG. 20C shows PCR identification results of samples collected from tails of F1 generation mice. Primer pairs Frt-F and Frt-R were used to amplify the Neo fragment to verify the removal of resistant fragments. WT is wild-type. H₂O is a blank control, + is a positive control and M is the Marker.

FIG. 20D shows PCR identification results of samples collected from tails of F1 generation mice. Primer pairs Flp-F2 and Flp-R2 were used to confirm the presence of the Flp fragments. WT is wild-type. H₂O is a blank control, + is a positive control and M is the Marker.

FIG. 21A is a graph showing the flow cytometry analysis result to detect LAG3 protein expression in unstimulated wild-type C57BL/6 mice, wherein cells were stained by mLAG-3 PE and mTcRβ PerCP.

FIG. 21B is a graph showing the flow cytometry analysis result to detect LAG3 protein expression in unstimulated LAG3 (l) humanized heterozygous mice, wherein cells were stained by mLAG-3 PE and mTcRβ PerCP.

FIG. 21C is a graph showing the flow cytometry analysis result to detect LAG3 protein expression in anti-mouse CD3 antibody-stimulated wild-type C57BL/6 mice, wherein cells were stained by mLAG-3 PE and mTcRβ PerCP.

FIG. 21D is a graph showing the flow cytometry analysis result to detect LAG3 protein expression in anti-mouse CD3 antibody-stimulated LAG3 (l) humanized heterozygous mice, wherein cells were stained by mLAG-3 PE and mTcRβ PerCP.

FIG. 21E is a graph showing the flow cytometry analysis result to detect LAG3 protein expression in unstimulated wild-type C57BL/6 mice, wherein cells were stained by hLAG-3 APC and mTcRβ PerCP.

FIG. 21F is a graph showing the flow cytometry analysis result to detect LAG3 protein expression in unstimulated LAG3 (l) humanized heterozygous mice, wherein cells were stained by hLAG-3 APC and mTcRβ PerCP.

FIG. 21G is a graph showing the flow cytometry analysis result to detect LAG3 protein expression in anti-mouse CD3 antibody-stimulated wild-type C57BL/6 mice, wherein cells were stained by hLAG-3 APC and mTcRβ PerCP.

FIG. 21H is a graph showing the flow cytometry analysis result to detect LAG3 protein expression in anti-mouse CD3 antibody-stimulated LAG3 (l) humanized heterozygous mice, wherein cells were stained by hLAG-3 APC and mTcRβ PerCP.

FIG. 25A is a graph showing the flow cytometry analysis result to detect LAG3 protein expression in anti-mouse CD3 antibody-stimulated wild-type C57BL/6 mice, wherein cells were stained by mLAG-3 PE and mTcRβ PerCP.

FIG. 25B is a graph showing the flow cytometry analysis result to detect LAG3 protein expression in anti-mouse CD3 antibody-stimulated LAG3 (s) gene humanized homozygous mice, wherein cells were stained by mLAG-3 PE and mTcRβ PerCP.

FIG. 25C is a graph showing the flow cytometry analysis result to detect LAG3 protein expression in anti-mouse CD3 antibody-stimulated wild-type C57BL/6 mice, wherein cells were stained by hLAG-3 APC and mTcRβ PerCP.

FIG. 25D is a graph showing the flow cytometry analysis result to detect LAG3 protein expression in anti-mouse CD3 antibody-stimulated LAG3 (s) gene humanized homozygous mice, wherein cells were stained by hLAG-3 APC and mTcRβ PerCP.

FIG. 32 shows the alignment between mouse LAG3 amino acid sequence (NP_032505.1; SEQ ID NO: 2) and human LAG3 amino acid sequence (NP_002277.4; SEQ ID NO: 4).

SEQUENCE LISTING

Figure 1:
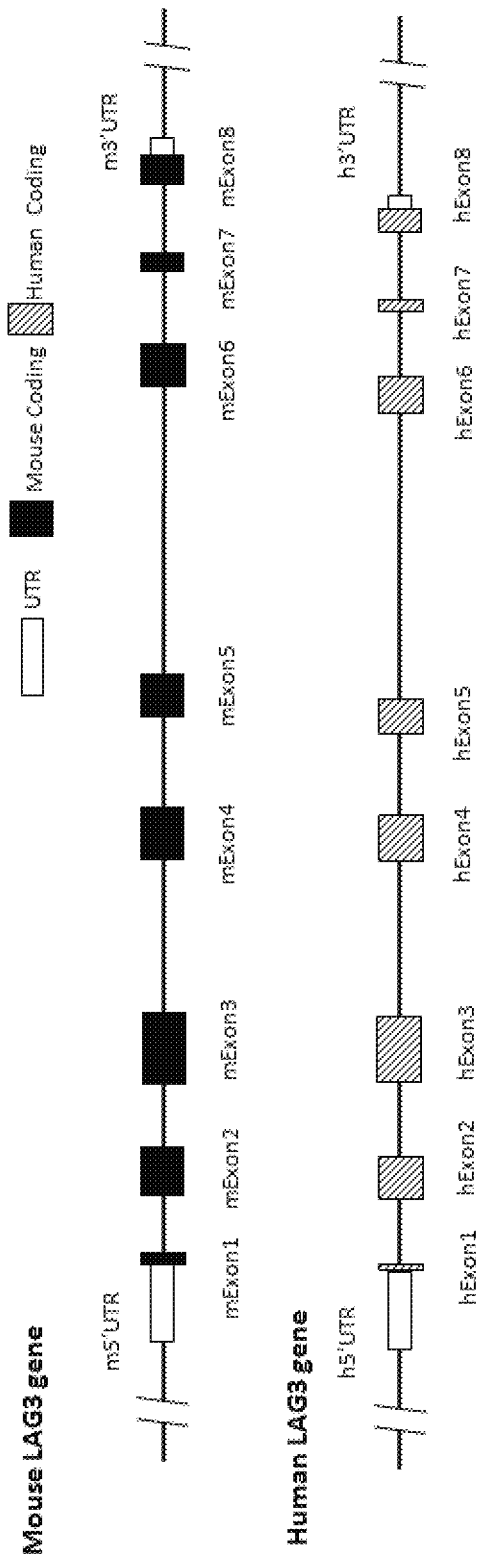
FIG. 1 is a schematic diagram showing the mouse LAG3 gene locus and the human LAG3 gene locus.

The instant application contains a Sequence Listing which has been submitted electronically in ASCII format and is hereby incorporated by reference in its entirety. Said ASCII copy, created on Nov. 10, 2020, is named Updated SEQ.txt and is 64,876 bytes in size.

DETAILED DESCRIPTION

This disclosure relates to transgenic non-human animal with human or chimeric (e.g., humanized) LAG3, and methods of use thereof.

Improved clinical outcomes have been achieved for a number of solid and hematological diseases treated with immune checkpoint blockade (ICB) targeting cytotoxic T lymphocyte associated protein (CTLA)-4 and programmed cell death 1 (PD-1) or its ligand PD-L1. Nevertheless, a large proportion of ICB-treated cancer patients still do not benefit from these drugs. Thus, while initial ICB targets have led to an immunological resurgence in oncology, this lack of widespread clinical benefit together with the occurrence of immune related adverse events (irAEs), principally due to the onset of autoimmune reactions, have focused attention on alternative inhibitory immune checkpoint molecules, e.g., lymphocyte activation gene 3 (LAG3, CD223).

LAG3 is the third inhibitory receptor pathway to be targeted in the clinic. LAG3 functions to control excessive activation following persistent antigen (Ag) exposure in an effort to prevent the onset of autoimmunity; however, it can also contribute to a state of T cell dysfunction in the tumor microenvironment (TME). Dysfunctional T cells are characterized by impaired proliferation and cytokine production that distinguishes their inability to exert effector functions despite previous Ag encounters. Ineffective T cells have been detected in chronic inflammatory settings, including autoimmune diseases and tumors (i.e., tumor infiltrating lymphocytes or TIL). Various drugs targeting LAG3 are now available in the clinic with many more under development. Particularly, anti-human LAG3 antibodies can be potentially used as cancer therapies.

Experimental animal models are an indispensable research tool for studying the effects of these antibodies (e.g., anti-hLAG3 antibodies). Common experimental animals include mice, rats, guinea pigs, hamsters, rabbits, dogs, monkeys, pigs, fish and so on. However, there are many differences between human and animal genes and protein sequences, and many human proteins cannot bind to the animal's homologous proteins to produce biological activity, leading to that the results of many clinical trials do not match the results obtained from animal experiments. A large number of clinical studies are in urgent need of better animal models. With the continuous development and maturation of genetic engineering technologies, the use of human cells or genes to replace or substitute an animal's endogenous similar cells or genes to establish a biological system or disease model closer to human, and establish the humanized experimental animal models (humanized animal model) has provided an important tool for new clinical approaches or means. In this context, the genetically engineered animal model, that is, the use of genetic manipulation techniques, the use of human normal or mutant genes to replace animal homologous genes, can be used to establish the genetically modified animal models that are closer to human gene systems. The humanized animal models have various important applications. For example, due to the presence of human or humanized genes, the animals can express or express in part of the proteins with human functions, so as to greatly reduce the differences in clinical trials between humans and animals, and provide the possibility of drug screening at animal levels.

Unless otherwise specified, the practice of the methods described herein can take advantage of the techniques of cell biology, cell culture, molecular biology, transgenic biology, microbiology, recombinant DNA and immunology. These techniques are explained in detail in the following literature, for examples: Molecular Cloning A Laboratory Manual, 2nd Ed., ed. By Sambrook, Fritsch and Maniatis (Cold Spring Harbor Laboratory Press: 1989); DNA Cloning, Volumes I and II (D. N. Glovered., 1985); Oligonucleotide Synthesis (M. J. Gaited., 1984); Mullisetal U.S. Pat. No. 4,683,195; Nucleic Acid Hybridization (B. D. Hames & S. J. Higginseds. 1984); Transcription And Translation (B. D. Hames & S. J. Higginseds. 1984); Culture Of Animal Cell (R. I. Freshney, Alan R. Liss, Inc., 1987); Immobilized Cells And Enzymes (IRL Press, 1986); B. Perbal, A Practical Guide To Molecular Cloning (1984), the series, Methods In ENZYMOLOGY (J. Abelson and M. Simon, eds.-in-chief, Academic Press, Inc., New York), specifically, Vols. 154 and 155 (Wuetal. eds.) and Vol. 185, "Gene Expression Technology" (D. Goeddel, ed.); Gene Transfer Vectors For Mammalian Cells (J. H. Miller and M. P. Caloseds., 1987, Cold Spring Harbor Laboratory); Immunochemical Methods In Cell And Molecular Biology (Mayer and Walker, eds., Academic Press, London, 1987); Hand book Of Experimental Immunology, Volumes V (D. M. Weir and C. C. Blackwell, eds., 1986); and Manipulating the Mouse Embryo, (Cold Spring Harbor Laboratory Press, Cold Spring Harbor, N. Y., 1986); each of which is incorporated herein by reference in its entirety.

Lymphocyte-Associated Gene 3

Lymphocyte-associated gene 3 (LAG3, LAG-3, or CD223) was identified as a novel transmembrane protein with a structural homology to CD4, as both exhibit four extracellular domains. Furthermore, the LAG3 gene is located close to the CD4 gene on chromosome 12. Despite these similarities on chromosomal localization and similar intron/exon organization, only approximately 20% of the amino acid sequences of these two molecules were identical. Structural properties were also similar with same extracellular folding patterns, which resulted in binding of LAG3 to major histocompatibility complex (MHC) class II as a ligand, even with an up to 100 times higher affinity than CD4.

LAG3 is mainly expressed in activated T and natural killer (NK) cells and was identified to as a marker for the activation of CD4+ and CD8+ T cells. Under pathological conditions, such as chronic inflammation or tumor environment, enhanced LAG3 expression on T cells was observed in combination with other inhibitory receptors such as programmed cell death receptor 1 (PD-1), T cell immunoglobulin and ITIM domain (TIGIT), T cell immunoglobulin-3 (TIM3), CD160, 2B4, which finally led to T cell dysfunction. Furthermore, LAG3 was mainly found on tumor infiltrating regulatory T cells (Tregs) in many types of cancer when compared with non-malignant peripheral cells.

Apart from immune and cancer cells, high LAG3 mRNA expression was commonly found in the red pulp of the spleen, thymic medulla and at the base of the cerebellum.

Modulation of LAG3 expression and its cleavage from the cell surface is an obligatory process for optimal T cell function. Via this cleavage, soluble LAG3 (sLAG3) is released to the circulation, where so far no clear biological function has been identified. Despite a lack of clinical evidence, detection of sLAG3 might serve as a prognostic biomarker in tuberculosis and as a diagnostic biomarker in type 1 diabetes. From a clinical perspective, sLAG3 might provide information on the activation status of LAG3 and could be used as a biomarker in clinical studies testing new immunotherapies.

The co-expression of LAG3 with other inhibitory molecules including PD-1, TIGIT, TIM3, 2B4, CD160 induces the exhaustion of immune cells, which results in diminished cytokine secretion. In line with these findings, the blockade of LAG3 on CD4 cells led to elevated production of interleukin (IL)-2, IL-4, interferon gamma and tumor necrosis factor alpha.

In humans, LAG3 was generally found to be co-expressed with PD-1, which together induced a T cell exhaustion state. Mainly, CD8+ positive tissue infiltrating lymphocytes isolated from patients with hepatocellular carcinoma, ovarian cancer and melanoma showed significant upregulation of LAG3 and high levels of PD-1. MHC class II molecules, as ligands of LAG3, are expressed in a variety of cells and tumors such as melanomas. LAG3 was frequently found to be ligated on MHC class II on melanoma cells, which lead to a clonal exhaustion of melanoma infiltrating T cells, thereby avoiding apoptosis. In colorectal cancer, LAG3 was found at higher extent in microsatellite instability high tumors, which are known to be susceptible to immunotherapy. Furthermore, LAG3 expression was found not only in tissue infiltrating lymphocytes but also in peripheral Tregs, tumor involved lymph nodes and within the tumor tissue itself, in melanoma and colon carcinoma. In patients with head and neck squamous cell carcinoma and non-small cell lung cancer, LAG3 was expressed on tumor infiltrating Tregs.

A detailed description of LAG3 and its function can be found, e.g., in Puhr et al. "New emerging targets in cancer immunotherapy: the role of LAG3." ESMO open 4.2 (2019): e000482; Solinas et al. "LAG3: The biological processes that motivate targeting this immune checkpoint molecule in human cancer." Cancers 11.8 (2019): 1213; each of which is incorporated by reference in its entirety.

In human genomes, LAG3 gene (Gene ID: 3902) locus has eight exons, exon 1, exon 2, exon 3, exon 4, exon 5, exon 6, exon 7, and exon 8 (FIG. 1). The LAG3 protein also has an extracellular region, a transmembrane region, and a cytoplasmic region, and the signal peptide is located at the extracellular region of LAG3. The nucleotide sequence for human LAG3 mRNA is NM_002286.5 (SEQ ID NO: 3), and the amino acid sequence for human LAG3 is NP_002277.4 (SEQ ID NO: 4). The location for each exon and each region in human LAG3 nucleotide sequence and amino acid sequence is listed below:

TABLE 1

| Human LAG-3 (approximate location) | NM_002286.5 1995bp (SEQ ID NO: 3) | NP_002277.4 525aa (SEQ ID NO: 4) |
|---|---|---|
| Exon 1 | 1-407 | 1-19 |
| Exon 2 | 408-555 | 20-69 |
| Exon 3 | 556-860 | 70-170 |
| Exon 4 | 861-1130 | 171-260 |
| Exon 5 | 1131-1406 | 261-352 |
| Exon 6 | 1407-1649 | 353-433 |
| Exon 7 | 1650-1780 | 434-477 |
| Exon 8 | 1781-1992 | 478-525 |
| Signal peptide | 350-415 | 1-22 |
| Extracellular region (excluding signal peptide region) | 416-1699 | 23-450 |
| Transmembrane region | 1700-1762 | 451-471 |
| Cytoplasmic region | 1763-1924 | 472-525 |
| Donor region in LAG3 (s) mice | 422-1123 | 25-258 |
| Donor region in LAG3 (l) mice | 422-1747 | 25-465 |

In mice, LAG3 gene locus has eight exons, exon 1, exon 2, exon 3, exon 4, exon 5, exon 6, exon 7, and exon 8 (FIG. 1). The mouse LAG3 protein also has an extracellular region, a transmembrane region, and a cytoplasmic region, and the signal peptide is located at the extracellular region of LAG3. The nucleotide sequence for mouse LAG3 mRNA is NM_008479.2 (SEQ ID NO: 1), the amino acid sequence for mouse LAG3 is NP_032505.1 (SEQ ID NO: 2). The location for each exon and each region in the mouse LAG3 nucleotide sequence and amino acid sequence is listed below:

TABLE 2

| Mouse LAG-3 (approximate location) | NM_008479.2 2020 bp SEQ ID NO: 1 | NP_032505.1 521aa SEQ ID NO: 2 |
|---|---|---|
| Exon 1 | 1-412 | 1-19 |
| Exon 2 | 413-560 | 20-69 |
| Exon 3 | 561-853 | 70-166 |
| Exon 4 | 854-1117 | 167-254 |
| Exon 5 | 1118-1393 | 255-346 |

TABLE 2-continued

| Mouse LAG-3 (approximate location) | NM_008479.2 2020 bp SEQ ID NO: 1 | NP_032505.1 521aa SEQ ID NO: 2 |
|---|---|---|
| Exon 6 | 1394-1630 | 347-425 |
| Exon 7 | 1631-1761 | 426-469 |
| Exon 8 | 1762-2003 | 470-521 |
| Signal peptide | 355-420 | 1-22 |
| Extracellular region (excluding signal peptide region) | 421-1680 | 23-442 |
| Transmembrane region | 1681-1743 | 443-463 |
| Cytoplasmic region | 1744-1917 | 464-521 |
| Replaced region in LAG3 (s) mice | 427-1110 | 25-252 |
| Replaced region in LAG3 (l) mice | 427-1728 | 25-458 |

The mouse LAG3 gene (Gene ID: 16768) is located in Chromosome 6 of the mouse genome, which is located from 124904359 to 124912434 of NC_000072.6 (GRCm38.p4 (GCF_000001635.24)). The 5'-UTR is from 124911705 to 124911352, exon 1 is from 124911351 to 124911294, the first intron is from 124,911,293 to 124,910,912, exon 2 is from 124,910,911 to 124,910,764, the second intron is from 124,910,763 to 124,910,397, exon 3 is from 124,910,396 to 124,910,104, the third intron is from 124,910,103 to 124,909,490, exon 4 is from 124,909,489 to 124,909,226, the fourth intron is from 124,909,225 to 124,908,653, exon 5 is from 24,908,652 to 124,908,377, the fifth intron is from 124,908,376 to 124,905,493, exon 6 is from 124,905,492 to 124,905,256, the sixth intron is from 124,905,255 to 124,904,969, exon 7 is from 124,904,968 to 124,904,838, the seventh intron is from 124,904,837 to 124,904,601, exon 8 is from 124,904,600 to 124,904,361, the 3'-UTR is from 124,904,441 to 124,904,361, based on transcript NM_008479.2. All relevant information for mouse Lag-3 locus can be found in the NCBI website with Gene ID: 16768, which is incorporated by reference herein in its entirety.

FIG. 32 shows the alignment between mouse LAG3 amino acid sequence (NP_032505.1; SEQ ID NO: 2) and human LAG3 amino acid sequence (NP_002277.4; SEQ ID NO: 4). Thus, the corresponding amino acid residue or region between human and mouse LAG3 can be found in FIG. 32.

LAG3 genes, proteins, and locus of the other species are also known in the art. For example, the gene ID for LAG3 in *Rattus norvegicus* is 297596, the gene ID for LAG3 in *Macaca mulatta* (Rhesus monkey) is 713737, the gene ID for LAG3 in *Canis lupus familiaris* (dog) is 486720, and the gene ID for LAG3 in *Felis catus* (domestic cat) is 101093114. The relevant information for these genes (e.g., intron sequences, exon sequences, amino acid residues of these proteins) can be found, e.g., in NCBI database, which is incorporated by reference herein in its entirety.

The present disclosure provides human or chimeric (e.g., humanized) LAG3 nucleotide sequence and/or amino acid sequences. In some embodiments, the entire sequence of mouse exon 1, exon 2, exon 3, exon 4, exon 5, exon 6, exon 7, exon 8, signal peptide, extracellular region, transmembrane region, and/or cytoplasmic region are replaced by the corresponding human sequence. In some embodiments, a "region" or "portion" of mouse exon 1, exon 2, exon 3, exon 4, exon 5, exon 6, exon 7, exon 8, signal peptide, extracellular region, transmembrane region, and/or cytoplasmic region are replaced by the corresponding human sequence. The term "region" or "portion" can refer to at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 250, 300, 350, 400, 500, or 600 nucleotides, or at least 1, 2, 3, 4, 5, 6, 7, 8, 9, 10, 20, 30, 40, 50, 60, 70, 80, 90, 100, 110, 120, 130, 140, 150, 160, 170, 180, 190, or 200 amino acid residues. In some embodiments, the "region" or "portion" can be at least 50%, 55%, 60%, 65%, 70%, 75%, 80%, 85%, 90%, 95%, or 99% identical to exon 1, exon 2, exon 3, exon 4, exon 5, exon 6, exon 7, exon 8, signal peptide, extracellular region, transmembrane region, or cytoplasmic region. In some embodiments, a region, a portion, or the entire sequence of mouse exon 1, exon 2, exon 3, exon 4, exon 5, exon 6, exon 7, and/or exon 8 (e.g., exon 2, exon 3, exon 4, exon 5, exon 6, exon 7) are replaced by the human exon 1, exon 2, exon 3, exon 4, exon 5, exon 6, exon 7, and/or exon 8 (e.g., exon 2, exon 3, exon 4, exon 5, exon 6, exon 7) sequence.

In some embodiments, the present disclosure also provides a chimeric (e.g., humanized) LAG3 nucleotide sequence and/or amino acid sequences, wherein in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from mouse LAG3 mRNA sequence (e.g., SEQ ID NO: 1), mouse LAG3 amino acid sequence (e.g., SEQ ID NO: 2), or a portion thereof (e.g., exon 2, exon 3, exon 4, exon 5, exon 6, and exon 7); and in some embodiments, at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the sequence are identical to or derived from human LAG3 mRNA sequence (e.g., SEQ ID NO: 3), human LAG3 amino acid sequence (e.g., SEQ ID NO: 4), or a portion thereof (e.g., exon 2, exon 3, exon 4, exon 5, exon 6, and exon 7).

In some embodiments, the sequence encoding amino acids 25-252 of mouse LAG3 (SEQ ID NO: 2) is replaced. In some embodiments, the sequence is replaced by a sequence encoding a corresponding region of human LAG3 (e.g., amino acids 25-258 of human LAG3 (SEQ ID NO: 4)).

In some embodiments, the sequence encoding amino acids 25-458 of mouse LAG3 (SEQ ID NO: 2) is replaced. In some embodiments, the sequence is replaced by a sequence encoding a corresponding region of human LAG3 (e.g., amino acids 25-465 of human LAG3 (SEQ ID NO: 4)).

In some embodiments, the nucleic acids as described herein are operably linked to a promotor or regulatory element, e.g., an endogenous mouse LAG3 promotor, an inducible promoter, an enhancer, and/or mouse or human regulatory elements.

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that are different from a portion of or the entire mouse LAG3 nucleotide sequence (e.g., exon 1, exon 2, exon 3, exon 4, exon 5, exon 6, exon 7, exon 8, or NM_008479.2 (SEQ ID NO: 1)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire mouse LAG3 nucleotide sequence (e.g., exon 1, exon 2, exon 3, exon 4, exon 5, exon 6, exon 7, exon 8, or NM_008479.2 (SEQ ID NO: 1)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is different from a portion of or the entire human LAG3 nucleotide sequence (e.g., exon 1, exon 2, exon 3, exon 4, exon 5, exon 6, exon 7, exon 8, or NM_002286.5 (SEQ ID NO: 3)).

In some embodiments, the nucleic acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 nucleotides, e.g., contiguous or non-contiguous nucleotides) that is the same as a portion of or the entire human LAG3 nucleotide sequence (e.g., exon 1, exon 2, exon 3, exon 4, exon 5, exon 6, exon 7, exon 8, or NM_002286.5 (SEQ ID NO: 3)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire mouse LAG3 amino acid sequence (e.g., exon 1, exon 2, exon 3, exon 4, exon 5, exon 6, exon 7, exon 8, or NP_032505.1 (SEQ ID NO: 2)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire mouse LAG3 amino acid sequence (e.g., exon 1, exon 2, exon 3, exon 4, exon 5, exon 6, exon 7, exon 8, or NP_032505.1 (SEQ ID NO: 2)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is different from a portion of or the entire human LAG3 amino acid sequence (e.g., exon 1, exon 2, exon 3, exon 4, exon 5, exon 6, exon 7, exon 8, or NP_002277.4 (SEQ ID NO: 4)).

In some embodiments, the amino acid sequence has at least a portion (e.g., at least 1, 2, 3, 4, 5, 6, 7, 8, 9, 10, 11, 12, 13, 14, 15, 20, 30, 40, 50, 60, 70, 80, 90, or 100 amino acid residues, e.g., contiguous or non-contiguous amino acid residues) that is the same as a portion of or the entire human LAG3 amino acid sequence (e.g., exon 1, exon 2, exon 3, exon 4, exon 5, exon 6, exon 7, exon 8, or NP_002277.4 (SEQ ID NO: 4)).

The present disclosure also provides a humanized LAG3 mouse amino acid sequence, wherein the amino acid sequence is selected from the group consisting of:

a) an amino acid sequence shown in SEQ ID NO: 9 or 44;

b) an amino acid sequence having a homology of at least 90% with or at least 90% identical to the amino acid sequence shown in SEQ ID NO: 9 or 44;

c) an amino acid sequence encoded by a nucleic acid sequence, wherein the nucleic acid sequence is able to hybridize to a nucleotide sequence encoding the amino acid shown in SEQ ID NO: 9 or 44 under a low stringency condition or a strict stringency condition;

d) an amino acid sequence having a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the amino acid sequence shown in SEQ ID NO: 9 or 44;

e) an amino acid sequence that is different from the amino acid sequence shown in SEQ ID NO: 9 or 44 by no more than 10, 9, 8, 7, 6, 5, 4, 3, 2 or no more than 1 amino acid; or f) an amino acid sequence that comprises a substitution, a deletion and/or insertion of one or more amino acids to the amino acid sequence shown in SEQ ID NO: 9 or 44.

The present disclosure also relates to a LAG3 nucleic acid (e.g., DNA or RNA) sequence, wherein the nucleic acid sequence can be selected from the group consisting of:

a) a nucleic acid sequence as shown in SEQ ID NO: 8 or 43, or a nucleic acid sequence encoding a homologous LAG3 amino acid sequence of a humanized mouse;

b) a nucleic acid sequence that is shown in SEQ ID NO: 7, 8, 68, 69, 70, 71, 42, 43, 45, 46, or 67;

c) a nucleic acid sequence that is able to hybridize to the nucleotide sequence as shown in SEQ ID NO: 7, 8, 68, 69, 70, 71, 42, 43, 45, 46, or 67 under a low stringency condition or a strict stringency condition;

d) a nucleic acid sequence that has a homology of at least 90%, 91%, 92%, 93%, 94%, 95%, 96%, 97%, 98%, or 99%, or at least 90%, 91%, 92%, 93%, 94%, 95%, 96%, 97%, 98%, or 99% identical to the nucleotide sequence as shown in SEQ ID NO: 7, 8, 68, 69, 70, 71, 42, 43, 45, 46, or 67;

e) a nucleic acid sequence that encodes an amino acid sequence, wherein the amino acid sequence has a homology of at least 90% with or at least 90% identical to the amino acid sequence shown in SEQ ID NO: 9 or 44;

f) a nucleic acid sequence that encodes an amino acid sequence, wherein the amino acid sequence has a homology of at least 90%, 91%, 92%, 93%, 94%, 95%, 96%, 97%, 98%, or 99% with, or at least 90%, 91%, 92%, 93%, 94%, 95%, 96%, 97%, 98%, or 99% identical to the amino acid sequence shown in SEQ ID NO: 9 or 44;

g) a nucleic acid sequence that encodes an amino acid sequence, wherein the amino acid sequence is different from the amino acid sequence shown in SEQ ID NO: 9 or 44 by no more than 10, 9, 8, 7, 6, 5, 4, 3, 2 or no more than 1 amino acid; and/or h) a nucleic acid sequence that encodes an amino acid sequence, wherein the amino acid sequence comprises a substitution, a deletion and/or insertion of one or more amino acids to the amino acid sequence shown in SEQ ID NO: 9 or 44.

The present disclosure further relates to a LAG3 genomic DNA sequence of a humanized mouse. The DNA sequence is obtained by a reverse transcription of the mRNA obtained by transcription thereof is consistent with or complementary to the DNA sequence homologous to the sequence shown in SEQ ID NO: 8 or SEQ ID NO: 43.

The disclosure also provides an amino acid sequence that has a homology of at least 90% with, or at least 90% identical to the sequence shown in SEQ ID NO: 9 or 44, and has protein activity. In some embodiments, the homology with the sequence shown in SEQ ID NO: 9 or 44 is at least about 90%, 91%, 92%, 93%, 94%, 95%, 96%, 97%, 98%, or at least 99%. In some embodiments, the foregoing homology is at least about 60%, 61%, 62%, 63%, 64%, 65%, 66%, 67%, 68%, 69%, 70%, 71%, 72%, 73%, 74%, 75%, 80%, or 85%.

In some embodiments, the percentage identity with the sequence shown in SEQ ID NO: 9 or 44 is at least about 90%, 91%, 92%, 93%, 94%, 95%, 96%, 97%, 98%, or at least 99%. In some embodiments, the foregoing percentage identity is at least about 60%, 61%, 62%, 63%, 64%, 65%, 66%, 67%, 68%, 69%, 70%, 71%, 72%, 73%, 74%, 75%, 80%, or 85%.

The disclosure also provides a nucleotide sequence that has a homology of at least 90%, or at least 90% identical to the sequence shown in SEQ ID NO: 8 or SEQ ID NO: 43, and encodes a polypeptide that has protein activity. In some embodiments, the homology with the sequence shown in SEQ ID NO: 8 or SEQ ID NO: 43 is at least about 90%, 91%, 92%, 93%, 94%, 95%, 96%, 97%, 98%, or at least 99%. In some embodiments, the foregoing homology is at least about 50%, 55%, 60%, 65%, 66%, 67%, 68%, 69%, 70%, 71%, 72%, 73%, 74%, 75%, 80%, or 85%.

In some embodiments, the percentage identity with the sequence shown in SEQ ID NO: 8 or SEQ ID NO: 43 is at least about 90%, 91%, 92%, 93%, 94%, 95%, 96%, 97%, 98%, or at least 99%. In some embodiments, the foregoing percentage identity is at least about 50%, 55%, 60%, 65%, 66%, 67%, 68%, 69%, 70%, 71%, 72%, 73%, 74%, 75%, 80%, or 85%.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any peptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, 500, or 600 nucleotides. In some embodiments, the amino acid sequence is less than 5, 6, 7, 8, 9, 10, 20, 30, 40, 50, 60, 70, 80, 90, 100, 110, 120, 130, 140, 150, 160, 170, 180, 190, or 200 amino acid residues.

In some embodiments, the amino acid sequence (i) comprises an amino acid sequence; or (ii) consists of an amino acid sequence, wherein the amino acid sequence is any one of the sequences as described herein.

In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The percentage of residues conserved with similar physicochemical properties (percent homology), e.g. leucine and isoleucine, can also be used to measure sequence similarity. Families of amino acid residues having similar physicochemical properties have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The homology percentage, in many cases, is higher than the identity percentage.

Cells, tissues, and animals (e.g., mouse) are also provided that comprise the nucleotide sequences as described herein, as well as cells, tissues, and animals (e.g., mouse) that express human or chimeric (e.g., humanized) LAG3 from an endogenous non-human LAG3 locus.

Genetically Modified Animals

As used herein, the term "genetically-modified non-human animal" refers to a non-human animal having exogenous DNA in at least one chromosome of the animal's genome. In some embodiments, at least one or more cells, e.g., at least 1%, 2%, 3%, 4%, 5%, 10%, 20%, 30%, 40%, 50% of cells of the genetically-modified non-human animal have the exogenous DNA in its genome. The cell having exogenous DNA can be various kinds of cells, e.g., an endogenous cell, a somatic cell, an immune cell, a T cell, a B cell, an antigen presenting cell, a macrophage, a dendritic cell, a germ cell, a blastocyst, or an endogenous tumor cell. In some embodiments, genetically-modified non-human animals are provided that comprise a modified endogenous LAG3 locus that comprises an exogenous sequence (e.g., a human sequence), e.g., a replacement of one or more non-human sequences with one or more human sequences. The animals are generally able to pass the modification to progeny, i.e., through germline transmission.

As used herein, the term "chimeric gene" or "chimeric nucleic acid" refers to a gene or a nucleic acid, wherein two or more portions of the gene or the nucleic acid are from different species, or at least one of the sequences of the gene or the nucleic acid does not correspond to the wild-type nucleic acid in the animal. In some embodiments, the chimeric gene or chimeric nucleic acid has at least one portion of the sequence that is derived from two or more different sources, e.g., sequences encoding different proteins or sequences encoding the same (or homologous) protein of two or more different species. In some embodiments, the chimeric gene or the chimeric nucleic acid is a humanized gene or humanized nucleic acid.

As used herein, the term "chimeric protein" or "chimeric polypeptide" refers to a protein or a polypeptide, wherein two or more portions of the protein or the polypeptide are from different species, or at least one of the sequences of the protein or the polypeptide does not correspond to wild-type amino acid sequence in the animal. In some embodiments, the chimeric protein or the chimeric polypeptide has at least one portion of the sequence that is derived from two or more different sources, e.g., same (or homologous) proteins of different species. In some embodiments, the chimeric protein or the chimeric polypeptide is a humanized protein or a humanized polypeptide.

As used herein, the term "chimeric exon" refers to an exon, wherein two or more portions of the gene or the exon sequences are from different species. In some embodiments, at least 10%, 20%, 30%, 40%, 50%, 60%, 70%, 80%, or 90% of the exon sequences are from a human exon. In some embodiments, at least 10%, 20%, 30%, 40%, 50%, 60%, 70%, 80%, or 90% of the exon sequences are from a mouse exon.

In some embodiments, the chimeric gene or the chimeric nucleic acid is a humanized LAG3 gene or a humanized LAG3 nucleic acid. In some embodiments, at least one or more portions of the gene or the nucleic acid is from the human LAG3 gene, at least one or more portions of the gene or the nucleic acid is from a non-human LAG3 gene. In some embodiments, the gene or the nucleic acid comprises a sequence that encodes a LAG3 protein. The encoded LAG3 protein is functional or has at least one activity of the human LAG3 protein or the non-human LAG3 protein, e.g., binding with human or non-human MHC class II molecules, downregulating the immune response, inhibiting T effector cells, and/or or inducing Treg suppressive activity.

In some embodiments, the chimeric protein or the chimeric polypeptide is a humanized LAG3 protein or a humanized LAG3 polypeptide. In some embodiments, at least one or more portions of the amino acid sequence of the protein or the polypeptide is from a human LAG3 protein, and at least one or more portions of the amino acid sequence of the protein or the polypeptide is from a non-human LAG3 protein. The humanized LAG3 protein or the humanized LAG3 polypeptide is functional or has at least one activity of the human LAG3 protein or the non-human LAG3 protein.

In some embodiments, the humanized LAG3 locus has mouse exon 1, chimeric exon 2, human exon 3, chimeric exon 4, mouse exon 5, mouse exon 6, mouse exon 7, and mouse exon 8.

In some embodiments, the humanized LAG3 locus has mouse exon 1, chimeric exon 2, human exon 3, human exon 4, human exon 5, human exon 6, chimeric exon 7, and mouse exon 8.

The genetically modified non-human animal can be various animals, e.g., a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable embryonic stem (ES) cells are not readily available, other methods are employed to make a non-human animal comprising the genetic modification. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo. These methods are known in the art, and are described, e.g., in A. Nagy, et al., "Manipulating the Mouse Embryo: A Laboratory Manual (Third Edition)," Cold Spring Harbor Laboratory Press, 2003, which is incorporated by reference herein in its entirety.

In one aspect, the animal is a mammal, e.g., of the superfamily Dipodoidea or Muroidea. In some embodiments, the genetically modified animal is a rodent. The rodent can be selected from a mouse, a rat, and a hamster. In some embodiments, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some embodiments, the genetically modified rodent is selected from a true mouse or rat (family Muridae), a gerbil, a spiny mouse, and a crested rat. In some embodiments, the non-human animal is a mouse.

In some embodiments, the animal is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some embodiments, the mouse is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129S6 (129/SvEvTac), 129S7, 129S8, 129T1, 129T2. These mice are described, e.g., in Festing et al., Revised nomenclature for strain 129 mice, Mammalian Genome 10: 836 (1999); Auerbach et al., Establishment and Chimera Analysis of 129/SvEv- and C57BL/6-Derived Mouse Embryonic Stem Cell Lines (2000), both of which are incorporated herein by reference in the entirety. In some embodiments, the genetically modified mouse is a mix of the 129 strain and the C57BL/6 strain. In some embodiments, the mouse is a mix of the 129 strains, or a mix of the BL/6 strains. In some embodiments, the mouse is a BALB strain, e.g., BALB/c strain. In some embodiments, the mouse is a mix of a BALB strain and another strain. In some embodiments, the mouse is from a hybrid line (e.g., 50% BALB/c-50% 12954/Sv; or 50% C57BL/6-50% 129).

In some embodiments, the animal is a rat. The rat can be selected from a Wistar rat, an LEA strain, a Sprague Dawley strain, a Fischer strain, F344, F6, and Dark Agouti. In some embodiments, the rat strain is a mix of two or more strains selected from the group consisting of Wistar, LEA, Sprague Dawley, Fischer, F344, F6, and Dark Agouti.

The animal can have one or more other genetic modifications, and/or other modifications, that are suitable for the particular purpose for which the humanized LAG3 animal is made. For example, suitable mice for maintaining a xenograft (e.g., a human cancer or tumor), can have one or more modifications that compromise, inactivate, or destroy the immune system of the non-human animal in whole or in part. Compromise, inactivation, or destruction of the immune system of the non-human animal can include, for example, destruction of hematopoietic cells and/or immune cells by chemical means (e.g., administering a toxin), physical means (e.g., irradiating the animal), and/or genetic modification (e.g., knocking out one or more genes). Non-limiting examples of such mice include, e.g., NOD mice, SCID mice, NOD/SCID mice, IL2Rγ knockout mice, NOD/SCID/γcnull mice (Ito, M. et al., NOD/SCID/γcnull mouse: an excellent recipient mouse model for engraftment of human cells, Blood 100(9): 3175-3182, 2002), nude mice, and Rag1 and/or Rag2 knockout mice. These mice can optionally be irradiated, or otherwise treated to destroy one or more immune cell type. Thus, in various embodiments, a genetically modified mouse is provided that can include a humanization of at least a portion of an endogenous non-human LAG3 locus, and further comprises a modification that compromises, inactivates, or destroys the immune system (or one or more cell types of the immune system) of the non-human animal in whole or in part. In some embodiments, modification is, e.g., selected from the group consisting of a modification that results in NOD mice, SCID mice, NOD/SCID mice, IL-2Rγ knockout mice, NOD/SCID/γcnull mice, nude mice, Rag1 and/or Rag2 knockout mice, and a combination thereof. These genetically modified animals are described, e.g., in US20150106961, which is incorporated herein by reference in its entirety. In some embodiments, the mouse can include a replacement of all or part of mature LAG3 coding sequence with human mature LAG3 coding sequence.

Genetically modified non-human animals that comprise a modification of an endogenous non-human LAG3 locus. In some embodiments, the modification can comprise a human nucleic acid sequence encoding at least a portion of a mature LAG3 protein (e.g., at least 10%, 20%, 30%, 40%, 50%, 60%, 70%, 80%, 90%, 95%, 96%, 97%, 98%, or 99% identical to the mature LAG3 protein sequence). Although genetically modified cells are also provided that can comprise the modifications described herein (e.g., ES cells, somatic cells), in many embodiments, the genetically modified non-human animals comprise the modification of the endogenous LAG3 locus in the germline of the animal.

Genetically modified animals can express a human LAG3 and/or a chimeric (e.g., humanized) LAG3 from endogenous mouse loci, wherein the endogenous mouse LAG3 gene has been replaced with a human LAG3 gene and/or a nucleotide sequence that encodes a region of human LAG3 sequence or an amino acid sequence that is at least 10%, 20%, 30%, 40%, 50%, 60%, 70%, 80%, 90%, 95%, 96%, 97%, 98%, or 99% identical to the human LAG3 sequence. In various embodiments, an endogenous non-human LAG3 locus is modified in whole or in part to comprise human nucleic acid sequence encoding at least one protein-coding sequence of a mature LAG3 protein.

In some embodiments, the genetically modified mice express the human LAG3 and/or chimeric LAG3 (e.g., humanized LAG3) from endogenous loci that are under control of mouse promoters and/or mouse regulatory elements. The replacement(s) at the endogenous mouse loci provide non-human animals that express human LAG3 or chimeric LAG3 (e.g., humanized LAG3) in appropriate cell types and in a manner that does not result in the potential pathologies observed in some other transgenic mice known in the art. The human LAG3 or the chimeric LAG3 (e.g., humanized LAG3) expressed in animal can maintain one or more functions of the wildtype mouse or human LAG3 in the animal. For example, human or non-human LAG3 ligands can bind to the expressed LAG3, downregulating the immune response, inhibiting T effector cells, and/or or inducing Treg suppressive activity. Furthermore, in some embodiments, the animal does not express endogenous LAG3 or expresses a decreased level of endogenous LAG3. As used herein, the term "endogenous LAG3" refers to LAG3 protein that is expressed from an endogenous LAG3 nucleotide sequence of the non-human animal (e.g., mouse) before any genetic modification.

The genome of the animal can comprise a sequence encoding an amino acid sequence that is at least 70%, 75%, 80%, 85%, 90%, 95%, 99%, or 100% identical to human LAG3 (NP_002277.4) (SEQ ID NO: 4). In some embodiments, the genome comprises a sequence encoding an amino acid sequence that is at least 70%, 75%, 80%, 85%, 90%, 95%, 99%, or 100% identical to SEQ ID NO: 9 or 44.

The genome of the genetically modified animal can comprise a replacement at an endogenous LAG3 gene locus of a sequence encoding a region of endogenous LAG3 with a sequence encoding a corresponding region of human LAG3. In some embodiments, the sequence that is replaced is any sequence within the endogenous LAG3 gene locus, e.g., exon 1, exon 2, exon 3, exon 4, exon 5, exon 6, exon 7, exon 8, 5'-UTR, 3'-UTR, the first intron, the second intron, and the third intron, the fourth intron, the fifth intron, the sixth intron, the seventh intron, etc. In some embodiments, the sequence that is replaced is within the regulatory region of the endogenous LAG3 gene. In some embodiments, the sequence that is replaced is exon 2, exon 3, exon 4, or part thereof, of an endogenous mouse LAG3 gene locus. In some embodiments, the sequence that is replaced is exon 2, exon 3, exon 4, exon 5, exon 6, exon 7 or part thereof, of an endogenous mouse LAG3 gene locus. In some embodiments, exon 1, exon 2, exon 3, exon 4, exon 5, exon 6, exon 7, exon 8, 5'-UTR, 3'-UTR, the first intron, the second intron, and the third intron, the fourth intron, the fifth intron, the sixth intron, or the seventh intron is a chimeric nucleic acid.

The genetically modified animal can have one or more cells expressing a human or chimeric LAG3 (e.g., humanized LAG3) having an extracellular region, a transmembrane region and a cytoplasmic region, wherein the extracellular region comprises a sequence that is at least 50%, 60%, 70%, 80%, 90%, 95%, 99% identical to the extracellular region of human LAG3. In some embodiments, the extracellular region of the humanized LAG3 has a sequence that has at least 10, 20, 30, 40, 50, 60, 70, 80, 90, 100, 110, 120, 130, 140, 150, 160, 170, or 180 amino acids (e.g., contiguously or non-contiguously) that are identical to human LAG3. Because human LAG3 and non-human LAG3 (e.g., mouse LAG3) sequences, in many cases, are different, antibodies that bind to human LAG3 will not necessarily have the same binding affinity with non-human LAG3 or have the same effects to non-human LAG3. Therefore, the genetically modified animal having a human or a humanized extracellular region can be used to better evaluate the effects of anti-human LAG3 antibodies in an animal model.

In some embodiments, the genome of the genetically modified animal comprises a sequence encoding an amino acid sequence that corresponds to part or the entire sequence of exon 2, exon 3, and/or exon 4 of human LAG3, part or the entire sequence of extracellular region of human LAG3 (with or without signal peptide), or part or the entire sequence of amino acids 25-258 of SEQ ID NO: 4.

In some embodiments, the genome of the genetically modified animal comprises a sequence encoding an amino acid sequence that corresponds to part or the entire sequence of exon 2, exon 3, exon 4, exon 5, exon 6, and/or exon 7 of human LAG3, part or the entire sequence of extracellular region of human LAG3 (with or without signal peptide), or part or the entire sequence of amino acids 25-465 of SEQ ID NO: 4.

In some embodiments, the non-human animal can have, at an endogenous LAG3 gene locus, a nucleotide sequence encoding a chimeric human/non-human LAG3 polypeptide, wherein a human portion of the chimeric human/non-human LAG3 polypeptide comprises a portion of human LAG3 extracellular domain, and wherein the animal expresses a functional LAG3 on a surface of a cell of the animal. The human portion of the chimeric human/non-human LAG3 polypeptide can comprise a portion of exon 2, exon 3, and/or exon 4 of human LAG3. In some embodiments, the human portion of the chimeric human/non-human LAG3 polypeptide can comprise a sequence that is at least 80%, 85%, 90%, 95%, or 99% identical to amino acids 25-258 of SEQ ID NO: 4.

In some embodiments, the non-human animal can have, at an endogenous LAG3 gene locus, a nucleotide sequence encoding a chimeric human/non-human LAG3 polypeptide, wherein a human portion of the chimeric human/non-human LAG3 polypeptide comprises a portion of human LAG3 extracellular domain, and wherein the animal expresses a functional LAG3 on a surface of a cell of the animal. The human portion of the chimeric human/non-human LAG3 polypeptide can comprise a portion of exon 2, exon 3, exon 4, exon 5, exon 6, and/or exon 7 of human LAG3. In some embodiments, the human portion of the chimeric human/non-human LAG3 polypeptide can comprise a sequence that is at least 80%, 85%, 90%, 95%, or 99% identical to amino acids 25-465 of SEQ ID NO: 4.

In some embodiments, the non-human portion of the chimeric human/non-human LAG3 polypeptide comprises transmembrane and/or cytoplasmic regions of an endogenous non-human LAG3 polypeptide. There may be several advantages that are associated with the transmembrane and/or cytoplasmic regions of an endogenous non-human LAG3 polypeptide. For example, once a LAG3 ligand or an anti-LAG3 antibody binds to LAG3, they can properly transmit extracellular signals into the cells and initiate the downstream pathway. A human or humanized transmembrane and/or cytoplasmic regions may not function properly in non-human animal cells. In some embodiments, a few extracellular amino acids that are close to the transmembrane region of LAG3 are also derived from endogenous sequence. These amino acids can also be important for transmembrane signal transmission. In some embodiments, the transmembrane region is chimeric.

Furthermore, the genetically modified animal can be heterozygous with respect to the replacement at the endogenous LAG3 locus, or homozygous with respect to the replacement at the endogenous LAG3 locus.

In some embodiments, the humanized LAG3 locus lacks a human LAG3 5'-UTR. In some embodiment, the humanized LAG3 locus comprises a rodent (e.g., mouse) 5'-UTR. In some embodiments, the humanization comprises a human 3'-UTR. In appropriate cases, it may be reasonable to presume that the mouse and human LAG3 genes appear to be similarly regulated based on the similarity of their 5'-flanking sequence. As shown in the present disclosure, humanized LAG3 mice that comprise a replacement at an endogenous mouse LAG3 locus, which retain mouse regulatory elements but comprise a humanization of LAG3 encoding sequence, do not exhibit pathologies. Both genetically modified mice that are heterozygous or homozygous for humanized LAG3 are grossly normal.

The present disclosure further relates to a non-human mammal generated through the method mentioned above. In some embodiments, the genome thereof contains human gene(s).

In some embodiments, the non-human mammal is a rodent, and preferably, the non-human mammal is a mouse.

In some embodiments, the non-human mammal expresses a protein encoded by a humanized LAG3 gene.

In addition, the present disclosure also relates to a tumor bearing non-human mammal model, characterized in that the non-human mammal model is obtained through the methods as described herein. In some embodiments, the non-human mammal is a rodent (e.g., a mouse).

The present disclosure further relates to a cell or cell line, or a primary cell culture thereof derived from the non-human mammal or an offspring thereof, or the tumor bearing non-human mammal; the tissue, organ or a culture thereof derived from the non-human mammal or an offspring thereof, or the tumor bearing non-human mammal; and the tumor tissue derived from the non-human mammal or an offspring thereof when it bears a tumor, or the tumor bearing non-human mammal.

The present disclosure also provides non-human mammals produced by any of the methods described herein. In some embodiments, a non-human mammal is provided; and the genetically modified animal contains the DNA encoding human or humanized LAG3 in the genome of the animal.

In some embodiments, the non-human mammal comprises the genetic construct as described herein (e.g., gene construct as shown in FIG. 2, FIG. 3, FIG. 4, FIG. 6, FIG. 7, FIG. 15). In some embodiments, a non-human mammal expressing human or humanized LAG3 is provided. In some embodiments, the tissue-specific expression of human or humanized LAG3 protein is provided.

In some embodiments, the expression of human or humanized LAG3 in a genetically modified animal is controllable, as by the addition of a specific inducer or repressor substance.

Non-human mammals can be any non-human animal known in the art and which can be used in the methods as described herein. Preferred non-human mammals are mammals, (e.g., rodents). In some embodiments, the non-human mammal is a mouse.

Genetic, molecular and behavioral analyses for the non-human mammals described above can performed. The present disclosure also relates to the progeny produced by the non-human mammal provided by the present disclosure mated with the same or other genotypes.

The present disclosure also provides a cell line or primary cell culture derived from the non-human mammal or a progeny thereof. A model based on cell culture can be prepared, for example, by the following methods. Cell cultures can be obtained by way of isolation from a non-human mammal, alternatively cell can be obtained from the cell culture established using the same constructs and the standard cell transfection techniques. The integration of genetic constructs containing DNA sequences encoding human LAG3 protein can be detected by a variety of methods.

There are many analytical methods that can be used to detect exogenous DNA, including methods at the level of nucleic acid (including the mRNA quantification approaches using reverse transcriptase polymerase chain reaction (RT-PCR) or Southern blotting, and in situ hybridization) and methods at the protein level (including histochemistry, immunoblot analysis and in vitro binding studies). In addition, the expression level of the gene of interest can be quantified by ELISA techniques well known to those skilled in the art. Many standard analysis methods can be used to complete quantitative measurements. For example, transcription levels can be measured using RT-PCR and hybridization methods including RNase protection, Southern blot analysis, RNA dot analysis (RNAdot) analysis. Immunohistochemical staining, flow cytometry, Western blot analysis can also be used to assess the presence of human or humanized LAG3 protein.

Vectors

The present disclosure relates to a targeting vector, comprising: a) a DNA fragment homologous to the 5' end of a region to be altered (5' arm), which is selected from the LAG3 gene genomic DNAs in the length of 100 to 10,000 nucleotides; b) a desired/donor DNA sequence encoding a donor region; and c) a second DNA fragment homologous to the 3' end of the region to be altered (3' arm), which is selected from the LAG3 gene genomic DNAs in the length of 100 to 10,000 nucleotides.

In some embodiments, a) the DNA fragment homologous to the 5' end of a conversion region to be altered (5' arm) is selected from the nucleotide sequences that have at least 90% homology to the NCBI accession number NC_000072.6; c) the DNA fragment homologous to the 3' end of the region to be altered (3' arm) is selected from the nucleotide sequences that have at least 90% homology to the NCBI accession number NC_000072.6.

In some embodiments, a) the DNA fragment homologous to the 5' end of a region to be altered (5' arm) is selected from the nucleotides from the position 124911766 to the position 124910898 of the NCBI accession number NC_000072.6; c) the DNA fragment homologous to the 3' end of the region to be altered (3' arm) is selected from the nucleotides from the position 124909232 to the position 124908030 of the NCBI accession number NC_000072.6.

In some embodiments, a) the DNA fragment homologous to the 5' end of a region to be altered (5' arm) is selected from the nucleotides from the position 124915890 to the position 124910898 of the NCBI accession number NC_000072.6; c) the DNA fragment homologous to the 3' end of the region to be altered (3' arm) is selected from the nucleotides from the position 124904008 to the position 124900076 of the NCBI accession number NC_000072.6.

In some embodiments, the length of the selected genomic nucleotide sequence in the targeting vector can be more than about 1 kb, about 1.5 kb, about 2 kb, about 2.5 kb, about 3 kb, about 3.5 kb, about 4 kb, about 4.5 kb, about 5 kb, about 5.5 kb, or about 6 kb.

In some embodiments, the region to be altered is exon 1, exon 2, exon 3, exon 4, exon 5, exon 6, exon 7, and/or exon 8 of LAG3 gene (e.g., exon 2, exon 3, exon 4, exon 5, exon 6, and/or exon 7 of mouse LAG3 gene). In some embodiments, the region to be altered is exon 2, exon 3, and exon 4.

The targeting vector can further include a selected gene marker.

In some embodiments, the sequence of the 5' arm is shown in SEQ ID NO: 5; and the sequence of the 3' arm is shown in SEQ ID NO: 6.

In some embodiments, the sequence of the 5' arm is shown in SEQ ID NO: 40; and the sequence of the 3' arm is shown in SEQ ID NO: 41.

In some embodiments, the sequence is derived from human (e.g., 6773206-6774857 of NC_000012.12). For example, the target region in the targeting vector is a part or entirety of the nucleotide sequence of a human LAG3, preferably exon 2, exon 3, exon 4, exon 5, exon 6, and/or exon 7 of the human LAG3. In some embodiments, the nucleotide sequence of the humanized LAG3 encodes the entire or the part of human LAG3 protein with the NCBI accession number NP_002277.4 (SEQ ID NO: 4). In some embodiments, the DNA fragment is SEQ ID NO: 7 or 42.

The disclosure also provides vectors for constructing a humanized animal model or a knock-out model. In some embodiments, the vectors comprise sgRNA sequence, wherein the sgRNA sequence target LAG3 gene, and the sgRNA is unique on the target sequence of the gene to be altered, and meets the sequence arrangement rule of 5'-NNN (20)-NGG3' or 5'-CCN—N(20)-3'; and in some embodiments, the targeting site of the sgRNA in the mouse LAG3 gene is located on the exon 1, exon 2, exon 3, exon 4, exon 5, exon 6, exon 7, exon 8, intron 1, intron 2, intron 3, intron 4, intron 5, intron 6, intron 7, upstream of exon 1, or downstream of exon 8 of the mouse LAG3 gene. In some embodiments, the sgRNAs target exon 2 and/or exon 4.

In some embodiments, the 5' targeting sequence for the sequence is shown as SEQ ID NOS: 10-16, and the sgRNA sequence recognizes the 5' targeting site. In some embodiments, the 3' targeting sequence for the knockout sequence is shown as SEQ ID NOS: 17-23 and the sgRNA sequence recognizes the 3' targeting site. Thus, the disclosure provides sgRNA sequences for constructing a genetic modified animal model.

In some embodiments, the oligonucleotide sgRNA sequences are set forth in SEQ ID NOS: 24-31.

In some embodiments, the disclosure relates to a plasmid construct (e.g., pT7-sgRNA) including the sgRNA sequence, and/or a cell including the construct. The disclosure also relates to a cell comprising the targeting vectors as described above.

In addition, the present disclosure further relates to a non-human mammalian cell, having any one of the foregoing targeting vectors, and one or more in vitro transcripts of the construct as described herein. In some embodiments, the cell includes Cas9 mRNA or an in vitro transcript thereof.

In some embodiments, the genes in the cell are heterozygous. In some embodiments, the genes in the cell are homozygous.

In some embodiments, the non-human mammalian cell is a mouse cell. In some embodiments, the cell is a fertilized egg cell.

Methods of Making Genetically Modified Animals

Genetically modified animals can be made by several techniques that are known in the art, including, e.g., non-homologous end-joining (NHEJ), homologous recombination (HR), zinc finger nucleases (ZFNs), transcription activator-like effector-based nucleases (TALEN), and the clustered regularly interspaced short palindromic repeats (CRISPR)-Cas system. In some embodiments, homologous recombination is used. In some embodiments, CRISPR-Cas9 genome editing is used to generate genetically modified animals. Many of these genome editing techniques are known in the art, and is described, e.g., in Yin et al., "Delivery technologies for genome editing," Nature Reviews Drug Discovery 16.6 (2017): 387-399, which is incorporated by reference in its entirety. Many other methods are also provided and can be used in genome editing, e.g., micro-injecting a genetically modified nucleus into an enucleated oocyte, and fusing an enucleated oocyte with another genetically modified cell.

Thus, in some embodiments, the disclosure provides replacing in at least one cell of the animal, at an endogenous LAG3 gene locus, a sequence encoding a region of an endogenous LAG3 with a sequence encoding a corresponding region of human or chimeric LAG3. In some embodiments, the replacement occurs in a germ cell, a somatic cell, a blastocyst, or a fibroblast, etc. The nucleus of a somatic cell or the fibroblast can be inserted into an enucleated oocyte.

Figure 4:
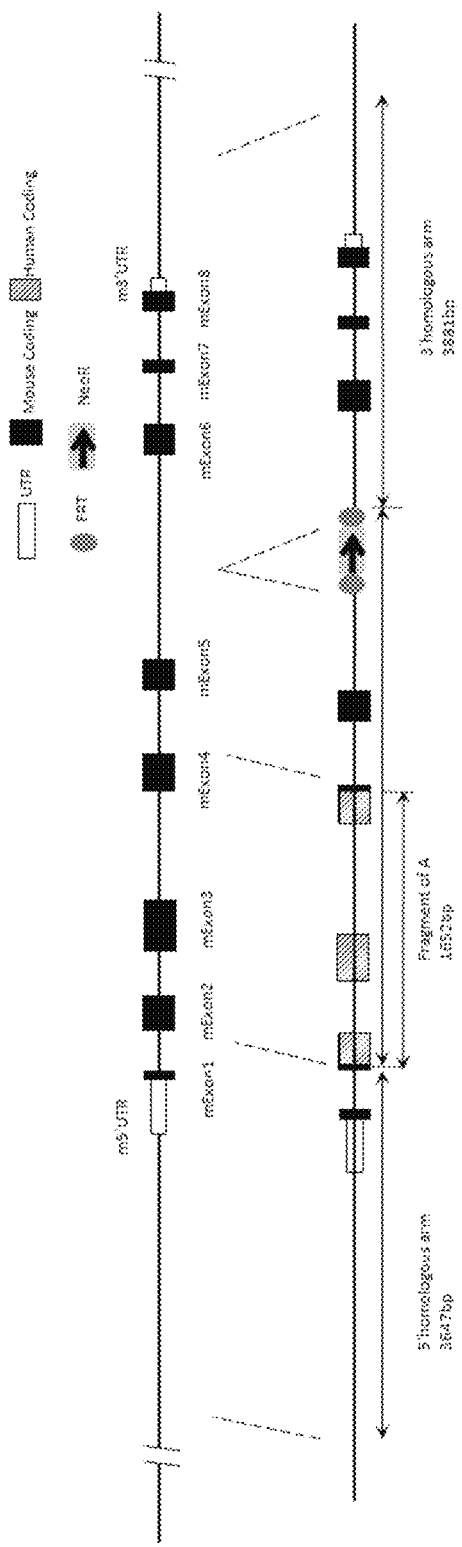
FIG. 4 is a schematic diagram showing a LAG3 gene targeting strategy for LAG3(s) mice.
Figure 7:
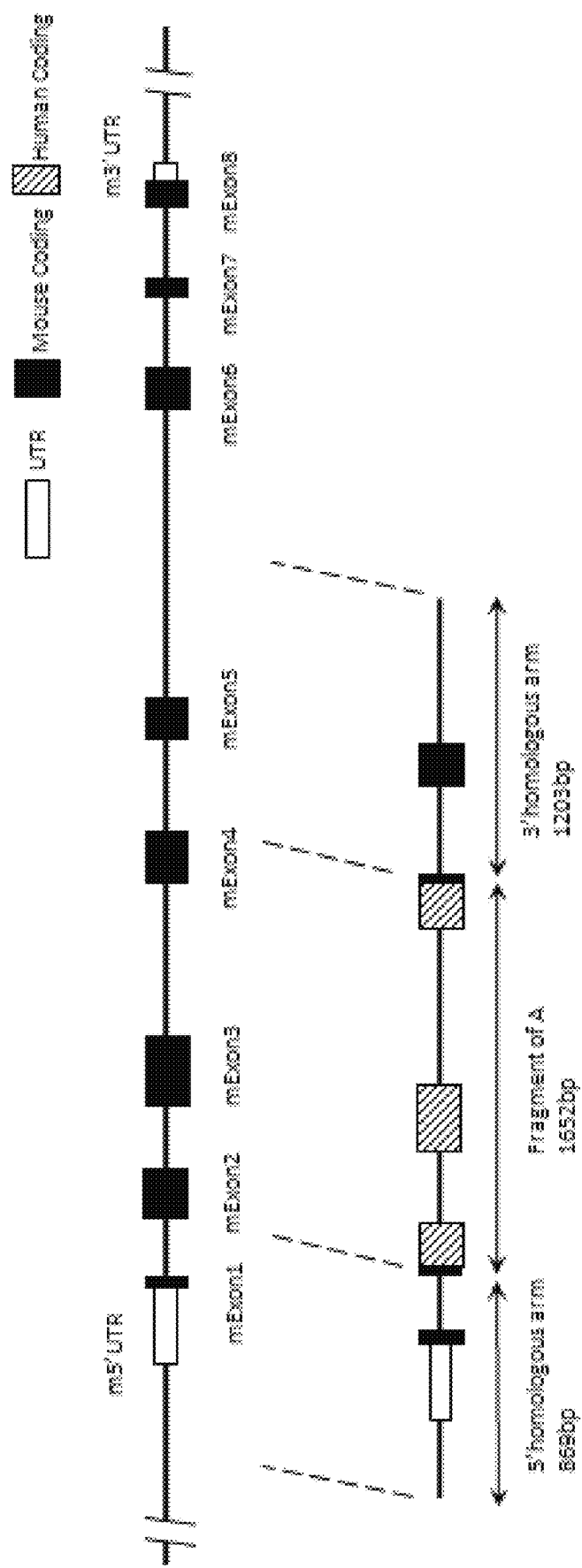
FIG. 7 is a schematic diagram showing a LAG3 gene targeting strategy for LAG3(s) mice.

FIG. 4 and FIG. 7 show a humanization strategy for a mouse LAG3 locus. In FIG. 4, the targeting strategy involves a vector comprising the 5' end homologous arm, human LAG3 gene fragment, mouse LAG3 gene fragment, an antibiotic resistance gene for positive clone screening (e.g., a Neo cassette), 3' end homologous arm and a negative selection marker (e.g., DTA). The process can involve replacing endogenous LAG3 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous LAG3 sequence with human LAG3 sequence.

In FIG. 7, the targeting strategy involves a vector comprising the 5' end homologous arm, human LAG3 gene fragment, 3' end homologous arm. The process can involve replacing endogenous LAG3 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous LAG3 sequence with human LAG3 sequence.

Figure 15:
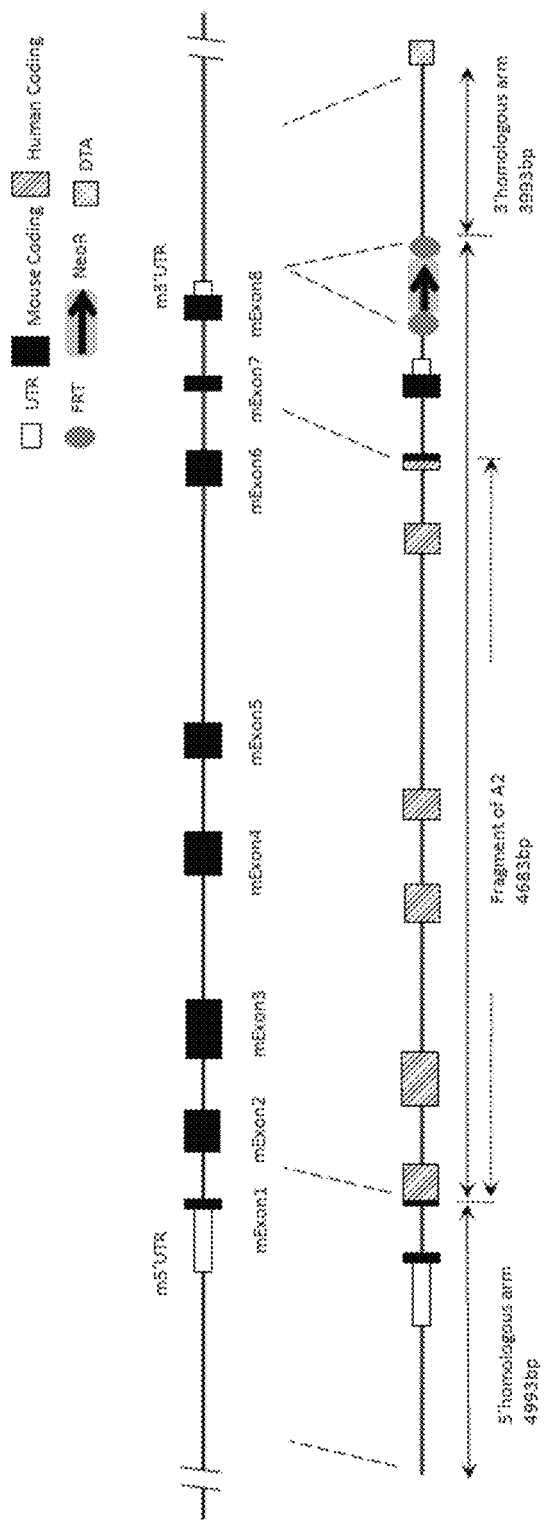
FIG. 15 is a schematic diagram showing a LAG3 gene targeting strategy for LAG (l) mice.

FIG. 15 shows a humanization strategy for a mouse LAG3 locus. In FIG. 15, the targeting strategy involves a vector comprising the 5' end homologous arm, human LAG3 gene fragment, mouse LAG3 gene fragment, an antibiotic resistance gene for positive clone screening (e.g., a Neo cassette), 3' end homologous arm and a negative selection marker (e.g., DTA). The process can involve replacing endogenous LAG3 sequence with human sequence by homologous recombination. In some embodiments, the cleavage at the upstream and the downstream of the target site (e.g., by zinc finger nucleases, TALEN or CRISPR) can result in DNA double strands break, and the homologous recombination is used to replace endogenous LAG3 sequence with human LAG3 sequence.

Thus, in some embodiments, the methods for making a genetically modified, humanized animal, can include the step of replacing at an endogenous LAG3 locus (or site), a nucleic acid encoding a sequence encoding a region of endogenous LAG3 with a sequence encoding a corresponding region of human LAG3. The sequence can include a region (e.g., a part or the entire region) of exon 1, exon 2, exon 3, exon 4, exon 5, exon 6, exon 7, and/or exon 8 of a human LAG3 gene. In some embodiments, the sequence includes a region of exon 2, exon 3 and exon 4, of a human LAG3 gene (e.g., amino acids 25-258 of SEQ ID NO: 4). In some embodiments, the sequence includes a region of exon 2, exon 3, exon 4, exon 5, exon 6, and exon 7 of a human LAG3 gene (e.g., amino acids 25-465 of SEQ ID NO: 4). In some embodiments, the region is located within the extracellular region of LAG3. In some embodiments, the endogenous LAG3 locus is exon 2, exon 3, exon 4, exon 5, exon 6, and/or exon 7 of mouse LAG3. In some embodiments, the endogenous LAG3 locus is exon 2, exon 3, and/or exon 4 of mouse LAG3.

In some embodiments, the methods of modifying a LAG3 locus of a mouse to express a chimeric human/mouse LAG3 peptide can include the steps of replacing at the endogenous mouse LAG3 locus a nucleotide sequence encoding a mouse LAG3 with a nucleotide sequence encoding a human LAG3, thereby generating a sequence encoding a chimeric human/mouse LAG3.

In some embodiments, the nucleotide sequence encoding the chimeric human/mouse LAG3 can include a first nucleotide sequence encoding an extracellular region of mouse LAG3 (with or without the mouse or human signal peptide sequence); a second nucleotide sequence encoding an extracellular region of human LAG3; a third nucleotide sequence encoding a transmembrane and a cytoplasmic region of a mouse LAG3.

In some embodiments, the nucleotide sequence encoding the chimeric human/mouse LAG3 can include a first nucleotide sequence encoding an extracellular region of mouse LAG3 (with or without the mouse or human signal peptide sequence); a second nucleotide sequence encoding an extracellular region of human LAG3; a third nucleotide sequence encoding an extracellular region of mouse LAG3; a fourth nucleotide sequence encoding a transmembrane and a cytoplasmic region of a mouse LAG3.

In some embodiments, the nucleotide sequence encoding the chimeric human/mouse LAG3 can include a first nucleotide sequence encoding an extracellular region of mouse LAG3 (with or without the mouse or human signal peptide sequence); a second nucleotide sequence encoding an extracellular region of human LAG3; a third nucleotide sequence encoding a transmembrane region of human LAG3; and a fourth nucleotide sequence encoding a transmembrane region and a cytoplasmic region of a mouse LAG3.

In some embodiments, the nucleotide sequences as described herein do not overlap with each other (e.g., the first nucleotide sequence, the second nucleotide sequence, and/or the third nucleotide sequence do not overlap). In some embodiments, the amino acid sequences as described herein do not overlap with each other.

The present disclosure further provides a method for establishing a LAG3 gene humanized animal model, involving the following steps:

(a) providing the cell (e.g. a fertilized egg cell) based on the methods described herein;

(b) culturing the cell in a liquid culture medium;

(c) transplanting the cultured cell to the fallopian tube or uterus of the recipient female non-human mammal, allowing the cell to develop in the uterus of the female non-human mammal;

(d) identifying the germline transmission in the offspring genetically modified humanized non-human mammal of the pregnant female in step (c).

In some embodiments, the non-human mammal in the foregoing method is a mouse (e.g., a C57BL/6 mouse).

In some embodiments, the non-human mammal in step (c) is a female with pseudo pregnancy (or false pregnancy).

In some embodiments, the fertilized eggs for the methods described above are C57BL/6 fertilized eggs. Other fertilized eggs that can also be used in the methods as described herein include, but are not limited to, FVB/N fertilized eggs, BALB/c fertilized eggs, DBA/1 fertilized eggs and DBA/2 fertilized eggs.

Fertilized eggs can come from any non-human animal, e.g., any non-human animal as described herein. In some embodiments, the fertilized egg cells are derived from rodents. The genetic construct can be introduced into a fertilized egg by microinjection of DNA. For example, by way of culturing a fertilized egg after microinjection, a cultured fertilized egg can be transferred to a false pregnant non-human animal, which then gives birth of a non-human mammal, so as to generate the non-human mammal mentioned in the methods described above.

Methods of Using Genetically Modified Animals

Replacement of non-human genes in a non-human animal with homologous or orthologous human genes or human sequences, at the endogenous non-human locus and under control of endogenous promoters and/or regulatory elements, can result in a non-human animal with qualities and characteristics that may be substantially different from a typical knockout-plus-transgene animal. In the typical knockout-plus-transgene animal, an endogenous locus is removed or damaged and a fully human transgene is inserted into the animal's genome and presumably integrates at random into the genome. Typically, the location of the integrated transgene is unknown; expression of the human protein is measured by transcription of the human gene and/or protein assay and/or functional assay. Inclusion in the human transgene of upstream and/or downstream human sequences are apparently presumed to be sufficient to provide suitable support for expression and/or regulation of the transgene.

In some cases, the transgene with human regulatory elements expresses in a manner that is unphysiological or otherwise unsatisfactory, and can be actually detrimental to the animal. The disclosure demonstrates that a replacement with human sequence at an endogenous locus under control of endogenous regulatory elements provides a physiologically appropriate expression pattern and level that results in a useful humanized animal whose physiology with respect to the replaced gene are meaningful and appropriate in the context of the humanized animal's physiology.

Genetically modified animals that express human or humanized LAG3 protein, e.g., in a physiologically appropriate manner, provide a variety of uses that include, but are not limited to, developing therapeutics for human diseases and disorders, and assessing the toxicity and/or the efficacy of these human therapeutics in the animal models.

In various aspects, genetically modified animals are provided that express human or humanized LAG3, which are useful for testing agents that can decrease or block the interaction between LAG3 and LAG3 ligands (e.g., MHC class II molecules) or the interaction between LAG3 and anti-human LAG3 antibodies, testing whether an agent can increase or decrease the immune response, and/or determining whether an agent is an LAG3 agonist or antagonist. The genetically modified animals can be, e.g., an animal model of a human disease, e.g., the disease is induced genetically (a knock-in or knockout). In various embodiments, the genetically modified non-human animals further comprise an impaired immune system, e.g., a non-human animal genetically modified to sustain or maintain a human xenograft, e.g., a human solid tumor or a blood cell tumor (e.g., a lymphocyte tumor, e.g., a B or T cell tumor).

In some embodiments, the genetically modified animals can be used for determining effectiveness of an anti-LAG3 antibody for the treatment of cancer. The methods involve administering the anti-LAG3 antibody (e.g., anti-human LAG3 antibody) to the animal as described herein, wherein the animal has a tumor; and determining the inhibitory effects of the anti-LAG3 antibody to the tumor. The inhibitory effects that can be determined include, e.g., a decrease of tumor size or tumor volume, a decrease of tumor growth, a reduction of the increase rate of tumor volume in a subject (e.g., as compared to the rate of increase in tumor volume in the same subject prior to treatment or in another subject without such treatment), a decrease in the risk of developing a metastasis or the risk of developing one or more additional metastasis, an increase of survival rate, and an increase of life expectancy, etc. The tumor volume in a subject can be determined by various methods, e.g., as determined by direct measurement, MRI or CT.

In some embodiments, the tumor comprises one or more cancer cells (e.g., human or mouse cancer cells) that are injected into the animal. In some embodiments, the anti-LAG3 antibody prevents MHC class II molecules from binding to LAG3. In some embodiments, the anti-LAG3 antibody or anti-MHC class II molecule antibody does not prevent MHC II class II molecules from binding to LAG3.

In some embodiments, the genetically modified animals can be used for determining whether an anti-LAG3 antibody is a LAG3 agonist or antagonist. In some embodiments, the methods as described herein are also designed to determine the effects of the agent (e.g., anti-LAG3 antibodies) on LAG3, e.g., whether the agent can stimulate immune cells or inhibit immune cells (e.g., T effector cells, Treg), whether the agent can increase or decrease the production of cytokines, whether the agent can activate or deactivate immune cells, and/or whether the agent can upregulate the immune response or downregulate immune response. In some embodiments, the genetically modified animals can be used for determining the effective dosage of a therapeutic agent for treating a disease in the subject, e.g., cancer, or autoimmune diseases.

The inhibitory effects on tumors can also be determined by methods known in the art, e.g., measuring the tumor volume in the animal, and/or determining tumor (volume) inhibition rate ($TGI_{TV}$). The tumor growth inhibition rate can be calculated using the formula $TGI_{TV}$ (%)=(1−TVt/TVc)×100, where TVt and TVc are the mean tumor volume (or weight) of treated and control groups.

In some embodiments, the anti-LAG3 antibody is designed for treating various cancers. As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancerous cells. Cancers that can be treated or diagnosed using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. In some embodiments, the agents described herein are designed for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, the anti-LAG3 antibody is designed for treating melanoma (e.g., advanced melanoma), non-small cell lung carcinoma (NSCLC), small cell lung cancer (SCLC), B-cell non-Hodgkin lymphoma, bladder cancer, and/or prostate cancer (e.g., metastatic hormone-refractory prostate cancer). In some embodiments, the anti-LAG3 antibody is designed for treating hepatocellular, ovarian, colon, or cervical carcinomas. In some embodiments, the anti-LAG3 antibody is designed for treating advanced breast cancer, advanced ovarian cancer, and/or advanced refractory solid tumor. In some embodiments, the anti-LAG3 antibody is designed for treating metastatic solid tumors, NSCLC, melanoma, non-Hodgkin lymphoma, colorectal cancer, and multiple myeloma. In some embodiments, the anti-LAG3 antibody is designed for treating melanoma, pancreatic carcinoma, mesothelioma, hematological malignancies (e.g., Non-Hodgkin's lymphoma, lymphoma, chronic lymphocytic leukemia), or solid tumors (e.g., advanced solid tumors). In some embodiments, the anti-LAG3 antibody is designed for treating carcinomas (e.g., nasopharynx carcinoma, bladder carcinoma, cervix carcinoma, kidney carcinoma or ovary carcinoma).

In some embodiments, the anti-LAG3 antibody is designed for treating various autoimmune diseases. Thus, the methods as described herein can be used to determine the effectiveness of an anti-LAG3 antibody in inhibiting immune response.

The present disclosure also provides methods of determining toxicity of an antibody (e.g., anti-LAG3 antibody). The methods involve administering the antibody to the animal as described herein. The animal is then evaluated for its weight change, red blood cell count, hematocrit, and/or hemoglobin. In some embodiments, the antibody can decrease the red blood cells (RBC), hematocrit, or hemoglobin by more than 20%, 30%, 40%, or 50%. In some embodiments, the animals can have a weight that is at least 5%, 10%, 20%, 30%, or 40% smaller than the weight of the control group (e.g., average weight of the animals that are not treated with the antibody).

In one aspect, the disclosure relates to a method of determining effectiveness of a LAG3 pathway modulator for treating a disease (e.g., reducing inflammation, treating an immune disorder, treating cancer). The method involves administering the LAG3 pathway modulator to the animal as described herein; and determining the effects of the LAG3 pathway modulator on the LAG3 pathway activity.

The present disclosure also relates to the use of the animal model generated through the methods as described herein in the development of a product related to an immunization processes of human cells, the manufacturing of a human antibody, or the model system for a research in pharmacology, immunology, microbiology and medicine.

In some embodiments, the disclosure provides the use of the animal model generated through the methods as described herein in the production and utilization of an animal experimental disease model of an immunization processes involving human cells, the study on a pathogen, or the development of a new diagnostic strategy and/or a therapeutic strategy.

The disclosure also relates to the use of the animal model generated through the methods as described herein in the screening, verifying, evaluating or studying the LAG3 gene function, human LAG3 antibodies, drugs for human LAG3 targeting sites, the drugs or efficacies for human LAG3 targeting sites, the drugs for immune-related diseases and antitumor drugs.

Genetically Modified Animal Model with Two or More Human or Chimeric Genes

The present disclosure further relates to methods for generating genetically modified animal model with two or more human or chimeric genes. The animal can comprise a human or chimeric LAG3 gene and a sequence encoding an additional human or chimeric protein.

In some embodiments, the additional human or chimeric protein can be programmed cell death protein 1 (PD-1), cytotoxic T-lymphocyte-associated protein 4 (CTLA-4), B And T Lymphocyte Associated (BTLA), Programmed Cell Death 1 Ligand 1 (PD-L1), CD27, CD28, CD40, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), Signal regulatory protein α (SIRPα) or TNF Receptor Superfamily Member 4 (TNFRSF4 or OX40).

The methods of generating genetically modified animal model with two or more human or chimeric genes (e.g., humanized genes) can include the following steps:

(a) using the methods of introducing human LAG3 gene or chimeric LAG3 gene as described herein to obtain a genetically modified non-human animal;

(b) mating the genetically modified non-human animal with another genetically modified non-human animal, and then screening the progeny to obtain a genetically modified non-human animal with two or more human or chimeric genes.

In some embodiments, in step (b) of the method, the genetically modified animal can be mated with a genetically modified non-human animal with human or chimeric PD-1, CTLA-4, BTLA, PD-L1, CD27, CD28, CD40, CD47, CD137, CD154, TIGIT, TIM-3, GITR, SIRPα, or OX40. Some of these genetically modified non-human animal are described, e.g., in PCT/CN2017/090320, PCT/CN2017/099577, PCT/CN2017/110435, PCT/CN2017/099576, PCT/CN2017/099574, PCT/CN2017/106024, PCT/CN2017/110494, PCT/CN2017/110435, PCT/CN2017/117984, PCT/CN2018/081628, PCT/CN2017/120388, PCT/CN2017/099575, and PCT/CN2018/081629; each of which is incorporated herein by reference in its entirety.

In some embodiments, the LAG3 humanization is directly performed on a genetically modified animal having a human or chimeric PD-1, CTLA-4, BTLA, PD-L1, CD27, CD28, CD40, CD47, CD137, CD154, TIGIT, TIM-3, GITR, SIRPα, or OX40 gene.

As these proteins may involve different mechanisms, a combination therapy that targets two or more of these proteins thereof may be a more effective treatment. In fact, many related clinical trials are in progress and have shown a good effect. The genetically modified animal model with two or more human or humanized genes can be used for determining effectiveness of a combination therapy that targets two or more of these proteins, e.g., an anti-LAG3 antibody and an additional therapeutic agent for the treatment of cancer. The methods include administering the anti-LAG3 antibody and the additional therapeutic agent to the animal, wherein the animal has a tumor; and determining the inhibitory effects of the combined treatment to the tumor. In some embodiments, the additional therapeutic agent is an antibody that specifically binds to PD-1, CTLA-4, BTLA, PD-L1, CD27, CD28, CD40, CD47, CD137, CD154, TIGIT, TIM-3, GITR, SIRPα, or OX40. In some embodiments, the additional therapeutic agent is an anti-CTLA4 antibody (e.g., ipilimumab), an anti-PD-1 antibody (e.g., nivolumab), or an anti-PD-L1 antibody.

In some embodiments, the animal further comprises a sequence encoding a human or humanized PD-1, a sequence encoding a human or humanized PD-L1, or a sequence encoding a human or humanized CTLA-4. In some embodiments, the additional therapeutic agent is an anti-PD-1 antibody (e.g., nivolumab, pembrolizumab), an anti-PD-L1 antibody, or an anti-CTLA-4 antibody. In some embodiments, the tumor comprises one or more tumor cells that express CD80, CD86, PD-L1, and/or PD-L2.

In some embodiments, the combination treatment is designed for treating various cancer as described herein, e.g., melanoma, non-small cell lung carcinoma (NSCLC), small cell lung cancer (SCLC), bladder cancer, prostate cancer (e.g., metastatic hormone-refractory prostate cancer), advanced breast cancer, advanced ovarian cancer, and/or advanced refractory solid tumor. In some embodiments, the combination treatment is designed for treating metastatic solid tumors, NSCLC, melanoma, B-cell non-Hodgkin lymphoma, colorectal cancer, and multiple myeloma. In some embodiments, the combination treatment is designed for treating melanoma, carcinomas (e.g., pancreatic carcinoma), mesothelioma, hematological malignancies (e.g., Non-Hodgkin's lymphoma, lymphoma, chronic lymphocytic leukemia), or solid tumors (e.g., advanced solid tumors).

In some embodiments, the methods described herein can be used to evaluate the combination treatment with some other methods. The methods of treating a cancer that can be used alone or in combination with methods described herein, include, e.g., treating the subject with chemotherapy, e.g., campothecin, doxorubicin, cisplatin, carboplatin, procarbazine, mechlorethamine, cyclophosphamide, adriamycin, ifosfamide, melphalan, chlorambucil, bisulfan, nitrosurea, dactinomycin, daunorubicin, bleomycin, plicomycin, mitomycin, etoposide, verampil, podophyllotoxin, tamoxifen, taxol, transplatinum, 5-flurouracil, vincristin, vinblastin, and/or methotrexate. Alternatively or in addition, the methods can include performing surgery on the subject to remove at least a portion of the cancer, e.g., to remove a portion of or all of a tumor(s), from the patient.

EXAMPLES

The invention is further described in the following examples, which do not limit the scope of the invention described in the claims.
Materials and Methods
The following materials were used in the following examples.

Ambion in vitro transcription kit was purchased from Ambion (Catalog number: AM1354).

E. coli TOP10 competent cells were purchased from the Tiangen Biotech (Beijing) Co. (Catalog number: CB104-02).

EcoRI, ScaI, HindIII, BamHI, XhoI, EcoRV, SalI, BbsI restriction enzymes were purchased from NEB (Catalog numbers: R3101M, R3122M, R3104M, R3136M, R0146M, R3195M, R3138M, R0539L, respectively).

Cas9 mRNA was purchased from SIGMA (Catalog number: CAS9MRNA-1EA).

C57BL/6 mice were purchased from the China Food and Drugs Research Institute National Rodent Experimental Animal Center.

Mouse colon cancer cell MC38 was purchased from Shanghai Enzyme Research Biotechnology Co. Ltd.

Bacterial Artificial Chromosome (BAC) bacteria were ordered from Invitrogen (Catalog number RPCI23.0 and RPCI11.C).

BV711 Hamster Anti-Mouse CD3e (mCD3) antibody was purchased from BD (Catalog number: 563123).

PE anti-mouse CD223 (LAG3) antibody (mLAG3 PE) was purchased from BioLegend (Catalog number 125208).

Alexa Fluor® 647 anti-human CD223 (LAG3) Antibody (hLAG3 AlexaFluor647) was purchased from BioLegend (Catalog number: 369304).

CD223 (LAG3) Monoclonal Antibody (3DS223H) (hLAG3 APC) was purchased from eBioscience (Catalog number: 17-2239-42).

PerCP/Cy5.5 anti-mouse TCR β chain (mTcRβ PerCP) was purchased from BioLegend (Catalog number: 109228).

Alexa Fluor® 647 AffiniPure F(ab)$_2$ Fragment Goat Anti-Human IgG, Fcγ fragment specific (anti-hIgG Alexa Fluor 647) was purchased from Jackson (Catalog number: 109-606-170).

FITC anti-Mouse TCR β Chain (mTcRβ FITC) was purchased from BioLegend (Catalog number: 109205).

Flow cytometer was purchased from BD Biosciences (model: FACS Calibur™).

Example 1: LAG3 Gene Humanized Mice

A schematic diagram for the mouse LAG3 gene (NCBI Gene ID: 16768, Primary source: MGI: 106588, UniProt ID: Q61790; located at 124904359 to 124912434 of chromosome 6 (NC_000072.6); based on the transcript of NCBI accession number NM_008479.2 NP_032505.1, wherein mRNA sequence is provided in SEQ ID NO: 1, and the corresponding protein sequence is provided in SEQ ID NO: 2) is shown in FIG. 1

FIG. 1 also shows the human LAG3 gene (NCBI Gene ID: 3902, Primary source: HGNC: 6476, UniProt ID: P18627; located at 6772483 to 6778455 of chromosome 12 (NC_000012.12); based on the transcript of NCBI accession number NM_002286.5→NP_002277.4, wherein mRNA sequence was provided in SEQ ID NO: 3, and the corresponding protein sequence is provided in SEQ ID NO: 4).

Figure 2:
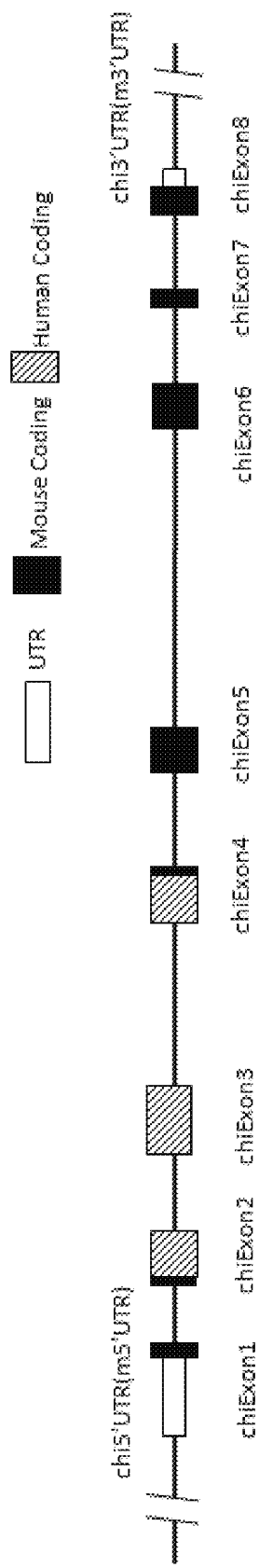
FIG. 2 is a schematic diagram showing humanized LAG3 gene locus in LAG3(short) (or LAG3(s)) mice. All or part of exon 2 to exon 4 are humanized.
Figure 3:
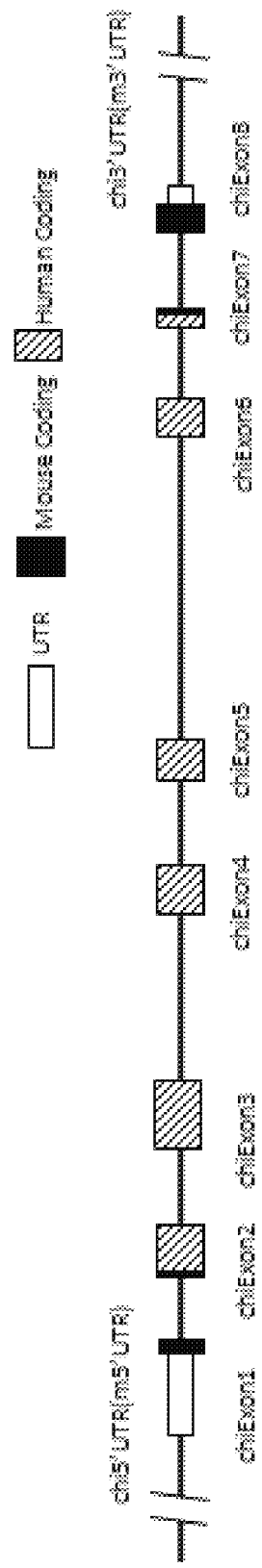
FIG. 3 is a schematic diagram showing humanized LAG3 gene locus in LAG3(long) (or LAG2(l)) mice. All or part of exon 2 to exon 7 are humanized.

For the purpose of the present experiments, a gene sequence encoding the human LAG3 protein can be introduced into the extracellular region of the endogenous mouse LAG3 locus, such that the mouse could express a human or humanized LAG3 protein. Mouse cells can be modified by gene editing techniques, for example, replacement of specific mouse LAG3 gene sequences with human LAG3 gene sequences at the endogenous mouse LAG3 locus. Under control of a mouse or human LAG3 regulatory element, a humanization strategy to obtain humanized LAG3 locus is shown in FIG. 2. Another LAG3 mouse humanization strategy is to replace a longer sequence in the extracellular region of the LAG3 gene, and the humanized mouse LAG3 locus is shown in FIG. 3.

The humanized LAG3 mouse shown in FIG. 2 was prepared by the following method. The targeting strategy was shown in FIG. 4. Mouse and human LAG3 DNA were obtained using bacterial artificial chromosomes (BAC) RP23-121J20 and RP11-578M14, respectively. The targeting vector in FIG. 4 contains a 5' homologous arm, a 3' homologous arm, and a DNA fragment containing the human LAG3 sequence (abbreviated as "A fragment"; SEQ ID NO: 7). The 5' homologous arm is identical to the nucleotide sequence of 124914544-124910898 of the NCBI accession number NC_000072.6; the 3' homologous arm is the same as the nucleotide sequence of 124903953-124907833 of the NCBI accession number NC_000072.6; the A fragment is the same as nucleotide sequence 6773206-6774857 of the NCBI accession number NC_000012.12. The mRNA sequence of the humanized mouse LAG3 and its encoded protein sequence are shown in SEQ ID NO: 8 and SEQ ID NO: 9, respectively.

The targeting vector also included an antibiotic resistance gene for positive clone screening (neomycin phosphotransferase encoding sequence Neo), and two Frt recombination sites on both sides of the antibiotic resistance gene that formed a Neo cassette. The junction between the 5' end of the Neo cassette and the mouse LAG3 locus was designed as (SEQ ID NO: 68)
5'-GAGGGACTCCCCTACTCTGAATTGCCAGGATGTCCAAGAAGGTAGAAA

CAGAGATGATAAAAATTTGAAAGAAAAATTTGAATGGTT*TGATCAAAGCTT*

*GAATTCCGAAGTTCCTATTCTCTAGAAAGTATAGGAAC*-3', wherein Neo cassette sequence is italic.

The junction between the 3' end of the Neo cassette with the mouse LAG3 locus was (SEQ ID NO: 69)
5'-*AGTTCCTATTCTCTAGAAAGTATAGGAACTTCATCAGTCAGGTACATA ATGGTG*AAAAGAATGAGGCATATATTTTTGAACCCTTGTCTGCTTTTGGCC TAGGGCTCTGTTAAAAT-3', wherein Neo cassette sequence is italic. The junction between the 5' end of the human LAG3 gene to mouse LAG3 locus was designed as (SEQ ID NO: 70)
5'-CTTGGCTCAATGCCCTTGGCCTCTCTTTTGTTCCACTAGTTGTGTC TTCAGGG*CCAGGGGCTGAGGTCCCGGTGGTGTGGGCCCAGGAGGGGGCT CCTGCCCAGCTCCCCTGCAGCCCCACAATCCCCCTC*-3', wherein the human LAG3 gene sequence is italic. The junction between the 3' end of the human LAG3 gene to mouse LAG3 locus was designed as (SEQ ID NO: 71)
5'-*TCCTCACCTACAGAGATGGCTTCAACGTCTCCATCATGTATAACCTC ACT*GTTCTGGGTAACTCTTCTAAGCAGCCTTGACCACAACCTTCCTGCTC ACCACCTCTCCTGACTCATGCATGGACCCCCAAAACTTTCTCAGCTGCGT GTGGTCTCACTCCACATCACTT-3', wherein the human LAG3 gene sequence is italic.

In addition, a negative selection marker (a sequence encoding the diphtheria toxin A subunit (DTA)) was also inserted downstream of the 3' homologous arm of the recombinant vector.

The targeting vectors were constructed by routine methods, such as PCR amplification, restriction enzyme digestion/ligation, gene synthesis, etc. Two constructed recombinant vectors were selected and verified by sequencing. The correct recombinant vector was electroporated and transfected into embryonic stem cells of C57BL/6 mice. The positive selectable marker gene was used to screen the cells, and gene recombination was confirmed by PCR using the following primer pairs:

```
WT-F1 (SEQ ID NO: 72):
5'-CTCCCTTCAACAGGGAG GCATGATG-3;

MT-R1 (SEQ ID NO: 73):
5'-CTTCAGAGGGAGTGACACCTCAGGG-3';
``` wherein positive clones had a 360 bp of PCR amplification products.

Figure 5A:
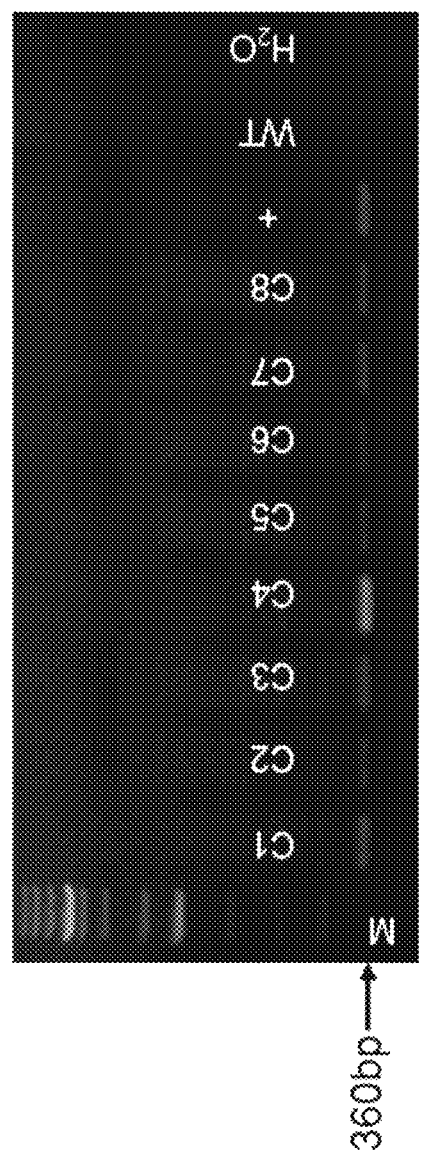
FIG. 5A shows PCR identification results. Primer pairs (WT-F1/MT-R1) were used for amplification. WT is wild-type. $H_2O$ is a blank control, + is a positive control and M is the Marker. C1-C8 are clone numbers.
Figure 5B:
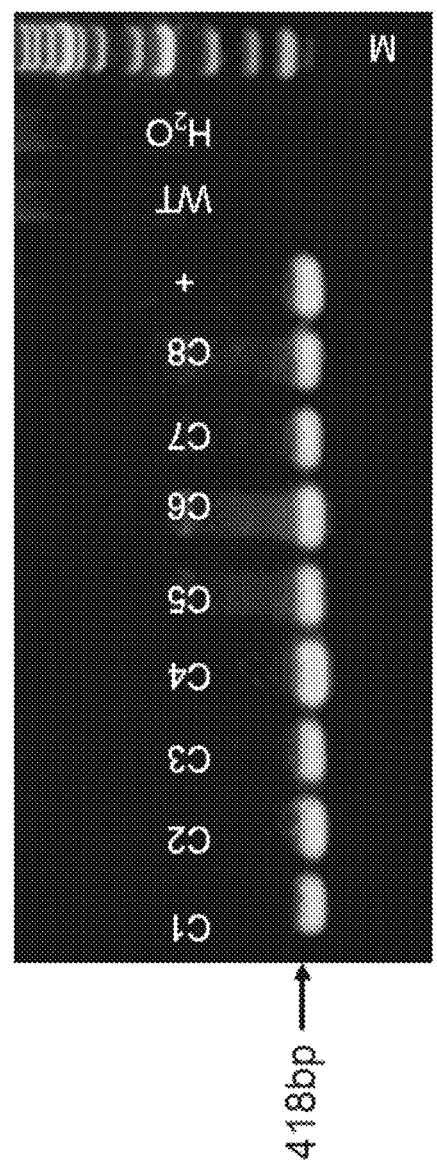
FIG. 5B shows PCR identification results. Primer pairs (MUT-F1/WT-R1) were used for amplification. WT is wild-type. $H_2O$ is a blank control, + is a positive control and M is the Marker. C1-C8 are clone numbers.
Figure 6:
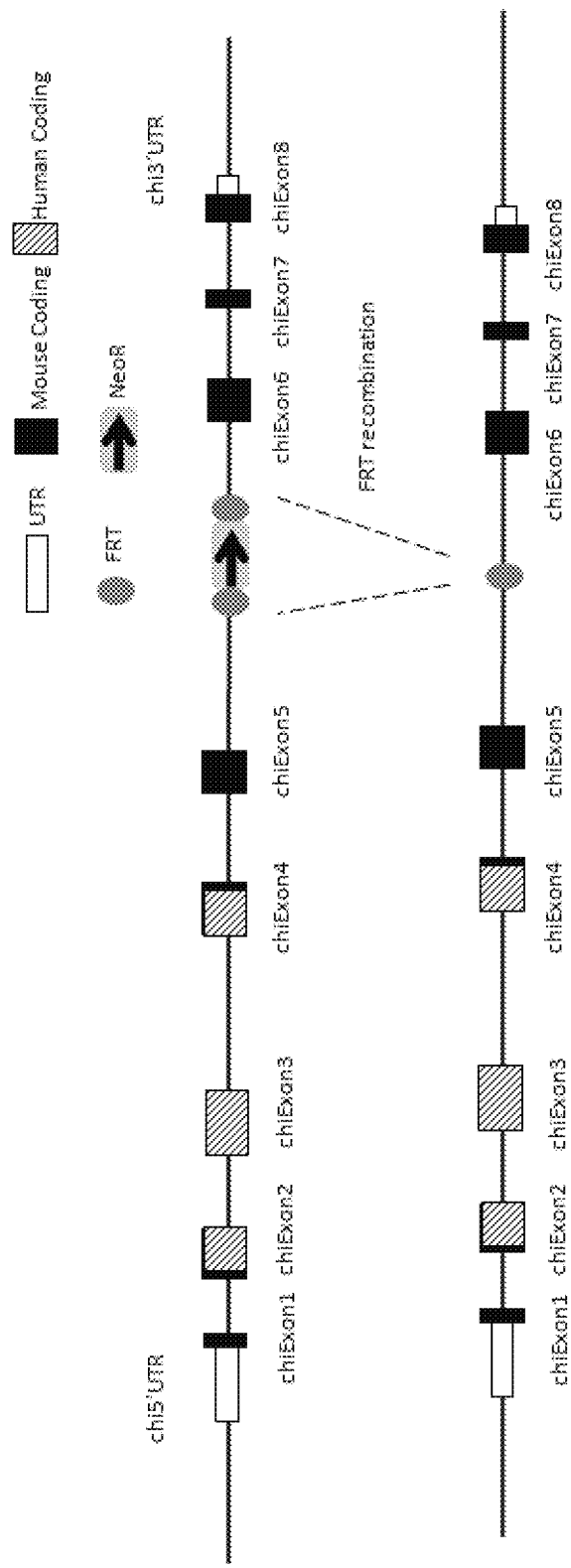
FIG. 6 is a schematic diagram showing the FRT recombination process that removes NeoR.

The following primer pairs were also used:

```
MUT-F1 (SEQ ID NO: 74):
5'-CAGGATCTCTCAGAGCCTCCGACTG-3';

WT-R1 (SEQ ID NO: 75):
5'-AGACAGCAGCTAAAAGATGCCCAGAG-3';
``` wherein positive clones had a 418 bp of PCR amplification products. The detection results are shown in FIGS. 5A-5B, indicating that all 8 cells were positive clones.

The positive clones from the screening (black mice) were introduced into isolated blastocysts (white mice), and the obtained chimeric blastocysts were transferred to the culture medium for a short-term culture and then transplanted to the fallopian tubes of the recipient mother (white mice) to produce the F0 chimeric mice (black and white). The F2 generation homozygous mice were obtained by backcrossing the F0 generation chimeric mice with wild-type mice to obtain the F1 generation mice, and then mating the F1 generation heterozygous mice with each other. The positive mice were also mated with the Flp tool mice to remove the positive selectable marker gene (the process was shown in FIG. 6), and then the humanized LAG3 homozygous mice expressing humanized LAG3 protein can be obtained by mating with each other.

CRISPR/Cas9 gene editing technology can also be used to obtain humanized mice for the replacement strategy shown in FIG. 2. The targeting strategy is shown in FIG. 7. The target sequences are important for the targeting specificity of sgRNAs and the efficiency of Cas9-induced cleavage. Based on the targeting strategy, sgRNA sequences recognizing the 5' end targeting site (sgRNA1-sgRNA7) and the 3' end targeting site (sgRNA8-sgRNA14) were designed and synthesized. The 5' end targeting site and the 3' end targeting site are located in exon 2 and exon 4 of the mouse LAG3 gene, respectively.

The targeting site sequences on LAG3 for each sgRNA are shown below:

```
sgRNA-1 target sequence (SEQ ID NO: 10):
5'-GTTCCACTAGTTGTGTCTTCAGG-3' sgRNA-2 target sequence (SEQ ID NO: 11):
5'-GGCCCTGAAGACACAACTAGTGG-3' sgRNA-3 target sequence (SEQ ID NO: 12):
5'-ACCACGGGGAGCTCTTTCCCAGG-3' sgRNA-4 target sequence (SEQ ID NO: 13):
5'-CTAGTTGTGTCTTCAGGGCCTGG-3' sgRNA-5 target sequence (SEQ ID NO: 14):
5'-GCCTGGGAAAGAGCTCCCCGTGG-3' sgRNA-6 target sequence (SEQ ID NO: 15):
5'-CCTCCTGGGCCCACACCACGGGG-3' sgRNA-7 target sequence (SEQ ID NO: 16):
5'-GGAAAGAGCTCCCCGTGGTGTGG-3' sgRNA-8 target sequence (SEQ ID NO: 17):
5'-TGACGCGGTGAGTTGTAGACAGG-3' sgRNA-9 target sequence (SEQ ID NO: 18):
5'-TGTAGACAGGCACTCGGTTCTGG-3' sgRNA-10 target sequence (SEQ ID NO: 19):
5'-CTCCATCACGTACAACCTCA AGG-3' sgRNA-11 target sequence (SEQ ID NO: 20):
5'-AGTCCTCAAGCTGTCTGATTGGG-3' sgRNA-12 target sequence (SEQ ID NO: 21):
5'-GTTTCAGCTAAAAAATGACGCGG-3' sgRNA-13 target sequence (SEQ ID NO: 22):
5'-GTCTCTGTGCACTGGTTCCAGGG-3' sgRNA-14 target sequence (SEQ ID NO: 23):
5'-CAGGCACTCGGTTCTGGCCCTGG-3'
```

Figures 8A, 8B:
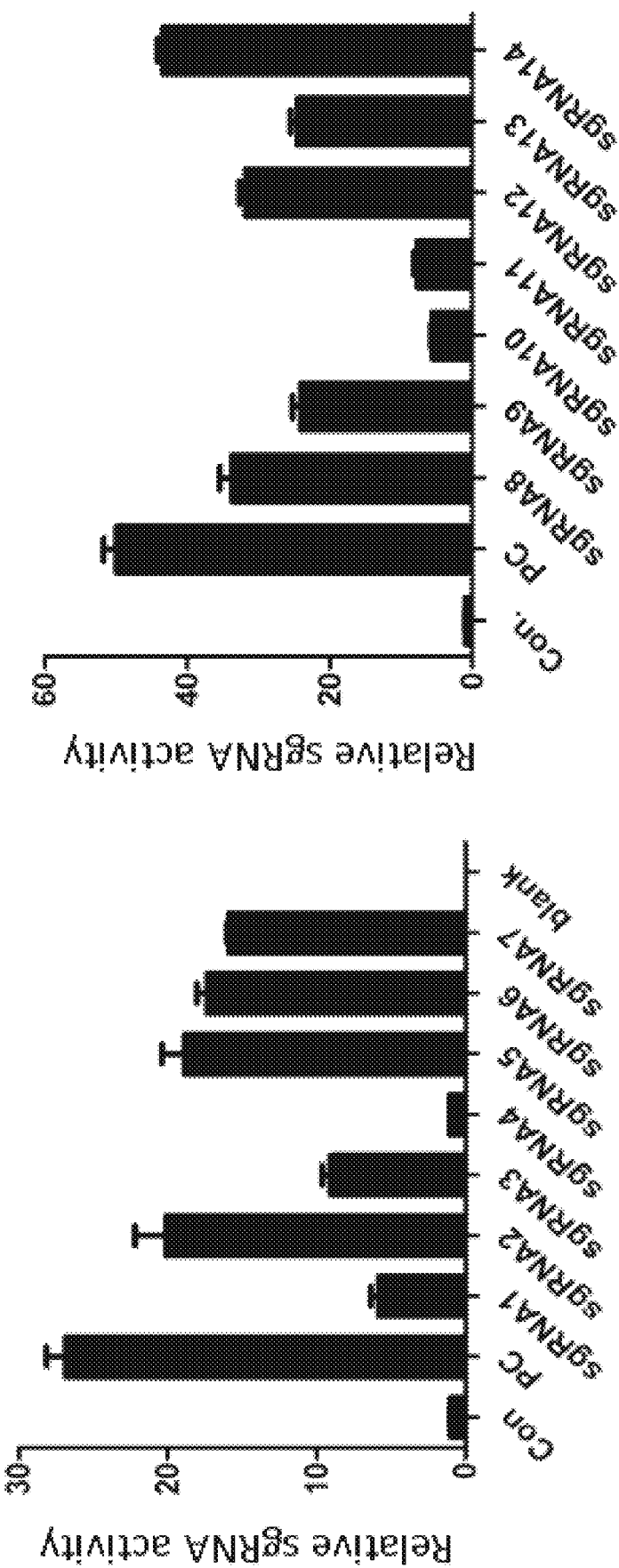
FIG. 8A is a histogram showing activity testing results for sgRNA1-sgRNA7. Con is a negative control; PC is a positive control; and blank is a blank control.
FIG. 8B is a histogram showing activity testing results for sgRNA8-sgRNA14. Con is a negative control; and PC is a positive control.

The UCA kit was used to detect the activities of sgRNAs. The results showed that the sgRNAs had different activities (see Table 3 and FIGS. 8A-8B). Because of the relatively high activities, sgRNA-5 and sgRNA-8 were selected for subsequent experiments. Oligonucleotides were added to the 5' end and the complementary strand to obtain a forward oligonucleotide and a reverse oligonucleotide (see Table 4 for the sequence). After annealing, the products were ligated to the pT7-sgRNA plasmid (the plasmid was first linearized with BbsI), respectively, to obtain expression vectors pT7-sgRNA5 and pT7-sgRNA8.

The pT7-sgRNA vector had a DNA fragment containing the T7 promoter and sgRNA scaffold (SEQ ID NO: 62), and was ligated to the backbone vector (Takara, Catalog number: 3299) by restriction enzyme digestion (EcoRI and BamHI) and ligation. The final plasmid was confirmed by sequencing.

TABLE 3 sgRNA activity test results

| 5' end targeting site test results | | 3' end targeting site test results | |
|---|---|---|---|
| Con. | 1.00 ± 0.17 | Con. | 1.00 ± 0.01 |
| PC | 26.85 ± 2.26 | PC | 49.99 ± 3.05 |
| sgRNA-1 | 5.85 ± 0.88 | sgRNA-8 | 33.79 ± 2.90 |
| sgRNA-2 | 20.12 ± 3.61 | sgRNA-9 | 24.11 ± 2.04 |
| sgRNA-3 | 9.07 ± 0.98 | sgRNA-10 | 5.66 ± 0.41 |
| sgRNA-4 | 1.07 ± 0.02 | sgRNA-11 | 7.79 ± 0.83 |
| sgRNA-5 | 18.84 ± 2.73 | sgRNA-12 | 31.88 ± 1.59 |
| sgRNA-6 | 17.34 ± 1.23 | sgRNA-13 | 24.62 ± 1.67 |
| sgRNA-7 | 15.91 ± 0.27 | sgRNA-14 | 43.44 ± 1.35 |

TABLE 4 sgRNA sequences

| | | |
|---|---|---|
| sgRNA-5 sequence | | |
| SEQ ID NO: 24 | | Upstream: 5'-gcctgggaaagagctccccg-3' |
| SEQ ID NO: 25 (forward oligonucleotide) | | Upstream: 5'-taggcctgggaaagagctccccg-3' |
| SEQ ID NO: 26 | | Downstream: 5'-cggggagctctttcccagg-3' |
| SEQ ID NO: 27 (reverse oligonucleotide) | | Downstream: 5'-aaaccggggagctctttcccagg-3' |
| sgRNA-8 sequence | | |
| SEQ ID NO: 28 | | Upstream: 5'-acgcggtgagttgtagac-3' |
| SEQ ID NO: 29 (forward oligonucleotide) | | Upstream: 5'-taggacgcggtgagttgtagac-3' |
| SEQ ID NO: 30 | | Downstream: 5'-gtctacaactcaccgcgt-3' |
| SEQ ID NO: 31 (reverse oligonucleotide) | | Downstream: 5'-aaacgtctacaactcaccgcgt-3' |

In the schematic diagram of the targeting strategy shown in FIG. 7, wherein the targeting vector comprises a 5' homologous arm (SEQ ID NO: 5), a 3' homologous arm (SEQ ID NO: 6), and a DNA fragment comprising the human LAG3 sequence. (referred to as "A fragment", SEQ ID NO: 7). The 5' homologous arm is identical to nucleotide sequence of 124911766-124910898 of the NCBI accession number NC_000072.6; the 3' homologous arm is identical to nucleotide sequence of 124909232-124908030 of the NCBI accession number NC_000072.6; and the A fragment is identical to nucleotide sequence of 6773206-6774857 of the NCBI accession number NC_000012.12. The mRNA sequence of the modified humanized mouse LAG3 and its encoded protein sequence are shown in SEQ ID NO: 8 and SEQ ID NO: 9, respectively.

The targeting vector can be constructed. The constructed recombinant vectors were initially verified by sequencing or enzymatic digestion, and the verification results are shown in FIGS. 9A-9B. Three sets of restriction enzymes were used for verification. Among them, BamHI+EcoRI should generate 2086 bp+5154 bp fragments; HindIII should generate 2472 bp+4768 bp fragments; and XhoI+NotI should generate 2064 bp+5176 bp fragments; the results of the enzyme digestion were in line with expectations. Among them, plasmids 2 and 3 were further confirmed by sequencing, and the confirmed plasmid 2 was used in subsequent experiments.

The pre-mixed Cas9 mRNA, in vitro transcription products of pT7-sgRNA5, pT7-sgRNA8 plasmids, and the targeting vectors were injected into the cytoplasm or nucleus of mouse fertilized eggs (C57BL/6 background) with a microinjection instrument (using Ambion in vitro transcription kit to carry out the transcription according to the method provided in the product instruction). The embryo microinjection was carried out according to the method described, e.g., in A. Nagy, et al., "Manipulating the Mouse Embryo: A Laboratory Manual (Third Edition)," Cold Spring Harbor Laboratory Press, 2003. The injected fertilized eggs were then transferred to a culture medium for a short time culture, and then was transplanted into the oviduct of the recipient mouse to produce the genetically modified humanized mice (F0 generation).

Figure 10A:
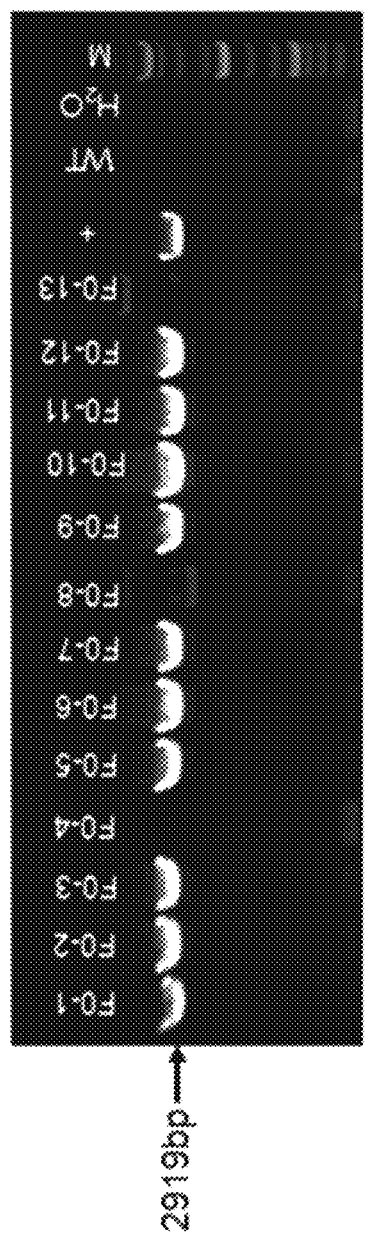
FIG. 10A shows PCR identification results of samples collected from tails of F0 generation mice. 5' primer pairs (L-GT-F/L-GT-R) were used for amplification. WT is wild-type. $H_2O$ is a blank control, + is a positive control and M is the Marker.
Figure 10B:
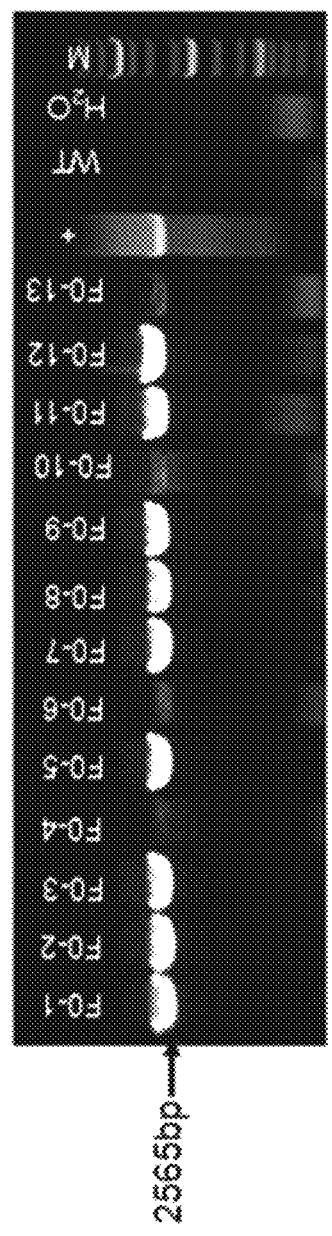
FIG. 10B shows PCR identification results of samples collected from tails of F0 generation mice. 3' primer pairs (R-GT-F/R-GT-R) were used for amplification. WT is wild-type. $H_2O$ is a blank control, + is a positive control and M is the Marker.
Figure 11A:
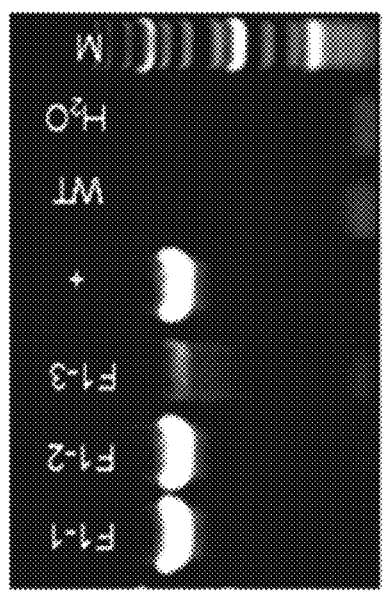
FIG. 11A shows PCR identification results of samples collected from tails of F1 generation mice. 5' primer pairs (L-GT-F/L-GT-R) were used for amplification. WT is wild-type. $H_2O$ is a blank control, + is a positive control and M is the Marker.
Figure 11B:
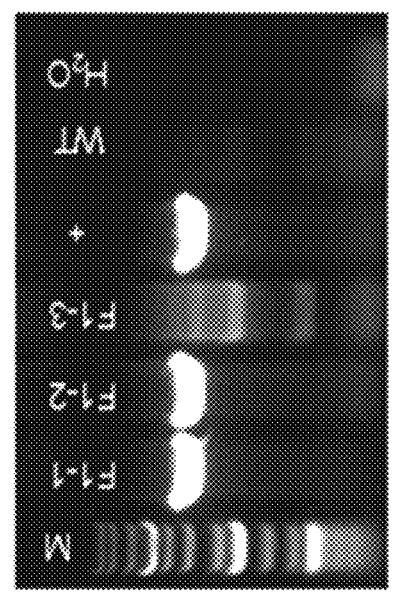
FIG. 11B shows PCR identification results of samples collected from tails of F1 generation mice. 3' primer pairs (R-GT-F/R-GT-R) were used for amplification. WT is wild-type. $H_2O$ is a blank control, + is a positive control and M is the Marker.

Genetically modified humanized mice obtained by the method above were verified by PCR. The identification results of some F0 mice are shown in FIGS. 10A-10B. Among them, seven mice numbered F0-1, F0-2, F0-3, F0-5, F0-7, F0-9, F0-11, and F0-12 were positive clones. The PCR analysis included the following primers:

L-GT-F:
(SEQ ID NO: 32)
5'-AGCATTCACACAGGGTGGGGAATTT-3';

L-GT-R:
(SEQ ID NO: 33)
5'-CTGGCCTGGAGTTTACTTGGCATCAG-3';

R-GT-F:
(SEQ ID NO: 34)
5'-CCCCTGGAGCTTCTCAACTCCATTC-3';

R-GT-R:
(SEQ ID NO: 35)
5'-CTCTGTTTCTACCTTCTTGGACATCCTGGC-3'.

The obtained F0 generation positive clone mice were mated with wild-type C57BL/6 mice to obtain F1 generation mice. The same PCR method can be used to identify the F1 mice, and the results of some F1 mice were shown in FIGS.

Figure 12:
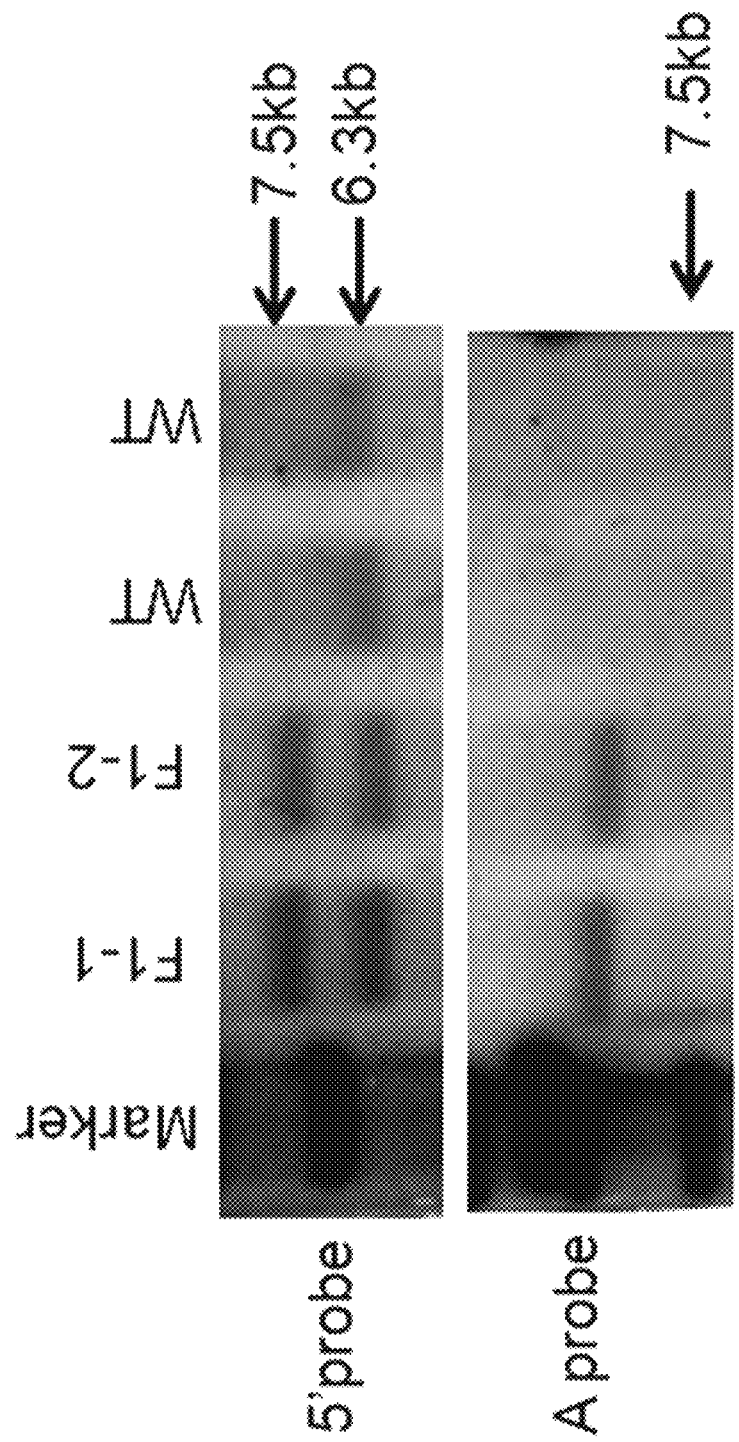
FIG. 12 is an image showing Southern blot results. WT indicates wild-type. F1-1 and F1-2 are mouse numbers.

11A-11B. The results showed that the mice numbered F1-1 and F1-2 were positive mice. Further detection results using Southern Blot technique are shown in FIG. 12. The results showed that the two mice, F1-1 and F1-2, were positive heterozygotes and no random insertions were detected. This indicated that this method can be used to construct genetically engineered mice without random insertions (hereinafter referred to as LAG3(s)).

DNA was digested with BamHI during Southern Blot and hybridized using 2 probes. The probes were as follows:

```
5' Probe:
F:
                                        (SEQ ID NO: 36)
5'-GGCCACTTATCATCACTTGCCC-3';

R:
                                        (SEQ ID NO: 37)
5'-GGTGGTAAAGGGGCCTAGGAG-3';

A Probe:
F:
                                        (SEQ ID NO: 38)
5'-CTCCAGAAGTGGATGCGGCCAGTCC-3';

R:
                                        (SEQ ID NO: 39)
5'-GCGGCAGGAGAGGGCGCGGTCCCTG-3'.
```

The expression of humanized LAG3 protein in mice were confirmed. Anti-mouse LAG3 antibody PE anti-mouse CD223 (LAG3) Antibody (mLAG3 PE) in combination with murine T cell surface antibody PerCP/Cy5.5 anti-mouse TCR β chain (mTcRβ PerCP), or anti-human LAG3 antibody CD223 (LAG3) Monoclonal Antibody (3DS223H) (hLAG3 APC) in combination with mTcRβ PerCP, were used to stain spleen cells that were obtained from anti-mouse CD3 antibody (mCD3)-stimulated mice. The results were analyzed by flow cytometry. The flow cytometry analysis (FIGS. 13A-13F) showed that the mouse LAG3 protein (FIG. 13C) and the humanized LAG3 protein (FIG. 13F) were detected in the spleen of the humanized heterozygous mice of LAG3 (s) gene. However, in the spleen of wild-type C57BL/6 mice, only the mouse LAG3 protein was detected (FIGS. 13A-13B), and no cells expressing human or humanized LAG3 protein were detected (FIGS. 13D-13E).

Heterozygous mice that were identified as positive were mated to each other to obtain humanized homozygous mice of LAG3 (s) gene. Wild-type C57BL/6 mice and humanized homozygous LAG3 (s) mice of 7-8 weeks old were subjected to the same method for flow cytometry detection of LAG3 protein expression. The results (FIGS. 25A-25D) indicated that the humanized LAG3 protein can be detected in the humanized homozygous LAG3 (s) gene (FIG. 25D). However, in wild-type mice, only expression of the mouse LAG3 protein was detected (FIG. 25A), and no cells expressing human or humanized LAG3 protein were detected (FIG. 25C).

Figures 26A, 26B, 26C, 26D, 26E, 26F:
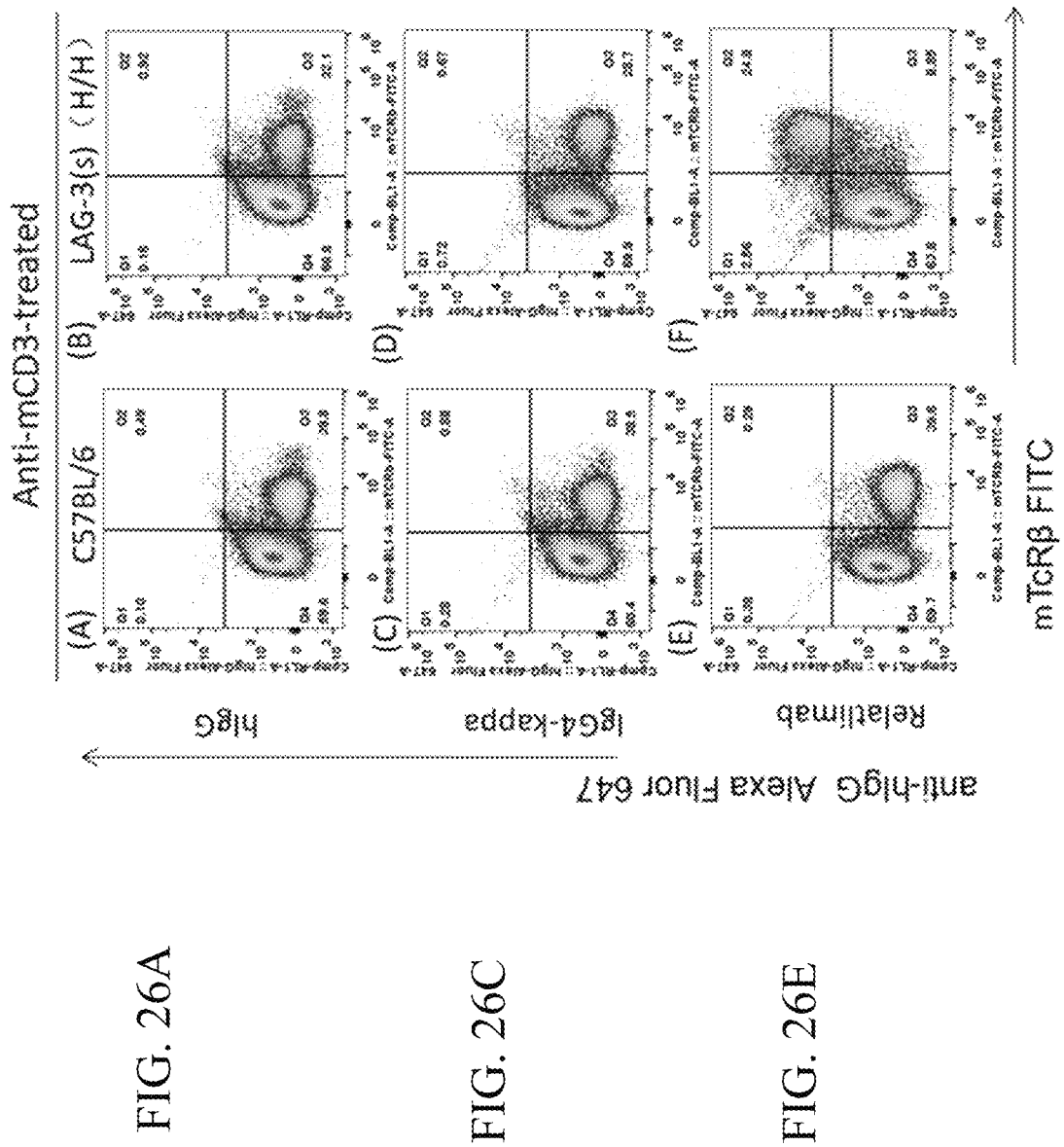
FIG. 26A is a graph showing the flow cytometry analysis result of anti-mouse CD3 antibody-stimulated wild-type C57BL/6 mice, wherein cells were stained by hIgG, anti-hIgG Alexa Fluor 647 and mTcRβ FITC. Flow cytometry was used to detect the binding ability of activated T cells to human LAG3 antibodies in mice.
FIG. 26B is a graph showing the flow cytometry analysis result of anti-mouse CD3 antibody-stimulated LAG3 (s) gene humanized homozygous mice, wherein cells were stained by hIgG, anti-hIgG Alexa Fluor 647 and mTcRβ FITC. Flow cytometry was used to detect the binding ability of activated T cells to human LAG3 antibodies in mice.
FIG. 26C is a graph showing the flow cytometry analysis result of anti-mouse CD3 antibody-stimulated wild-type C57BL/6 mice, wherein cells were stained by IgG4-kappa, anti-hIgG Alexa Fluor 647 and mTcRβ FITC. Flow cytometry was used to detect the binding ability of activated T cells to human LAG3 antibodies in mice.
FIG. 26D is a graph showing the flow cytometry analysis result of anti-mouse CD3 antibody-stimulated LAG3 (s) gene humanized homozygous mice, wherein cells were stained by IgG4-kappa, anti-hIgG Alexa Fluor 647 and mTcRβ FITC. Flow cytometry was used to detect the binding ability of activated T cells to human LAG3 antibodies in mice.
FIG. 26E is a graph showing the flow cytometry analysis result of anti-mouse CD3 antibody-stimulated wild-type C57BL/6 mice, wherein cells were stained by Relatlimab, anti-hIgG Alexa Fluor 647 and mTcRβ FITC. Flow cytometry was used to detect the binding ability of activated T cells to human LAG3 antibodies in mice.
FIG. 26F is a graph showing the flow cytometry analysis result of anti-mouse CD3 antibody-stimulated LAG3 (s) gene humanized homozygous mice, wherein cells were stained by Relatlimab, anti-hIgG Alexa Fluor 647 and mTcRβ FITC. Flow cytometry was used to detect the binding ability of activated T cells to human LAG3 antibodies in mice.
Figures 27A, 27B, 27C, 27D, 27E, 27F:
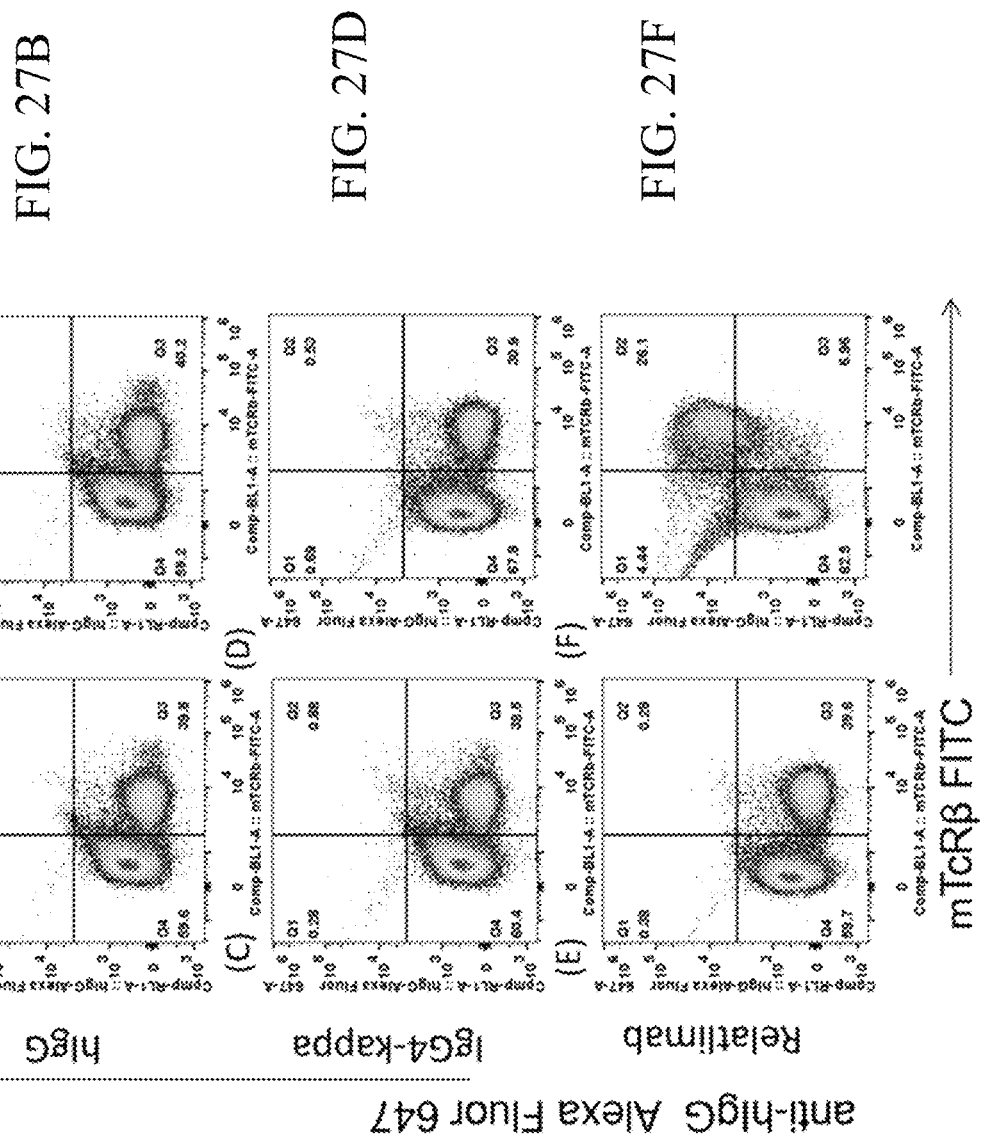
FIG. 27A is a graph showing the flow cytometry analysis result of anti-mouse CD3 antibody-stimulated wild-type C57BL/6 mice, wherein cells were stained by hIgG, anti-hIgG Alexa Fluor 647 and mTcRβ FITC. Flow cytometry was used to detect the binding ability of activated T cells to human LAG3 antibodies in mice.
FIG. 27B is a graph showing the flow cytometry analysis result of anti-mouse CD3 antibody-stimulated LAG3 (l) gene humanized homozygous mice, wherein cells were stained by hIgG, anti-hIgG Alexa Fluor 647 and mTcRβ FITC. Flow cytometry was used to detect the binding ability of activated T cells to human LAG3 antibodies in mice.
FIG. 27C is a graph showing the flow cytometry analysis result of anti-mouse CD3 antibody-stimulated wild-type C57BL/6 mice, wherein cells were stained by IgG4-kappa, anti-hIgG Alexa Fluor 647 and mTcRβ FITC. Flow cytometry was used to detect the binding ability of activated T cells to human LAG3 antibodies in mice.
FIG. 27D is a graph showing the flow cytometry analysis result of anti-mouse CD3 antibody-stimulated LAG3 (l) gene humanized homozygous mice, wherein cells were stained by IgG4-kappa, anti-hIgG Alexa Fluor 647 and mTcRβ FITC. Flow cytometry was used to detect the binding ability of activated T cells to human LAG3 antibodies in mice.
FIG. 27E is a graph showing the flow cytometry analysis result of anti-mouse CD3 antibody-stimulated wild-type C57BL/6 mice, wherein cells were stained by Relatlimab, anti-hIgG Alexa Fluor 647 and mTcRβ FITC. Flow cytometry was used to detect the binding ability of activated T cells to human LAG3 antibodies in mice.
FIG. 27F is a graph showing the flow cytometry analysis result of anti-mouse CD3 antibody-stimulated LAG3 (l) gene humanized homozygous mice, wherein cells were stained by Relatlimab, anti-hIgG Alexa Fluor 647 and mTcRβ FITC. Flow cytometry was used to detect the binding ability of activated T cells to human LAG3 antibodies in mice.
Figure 28:
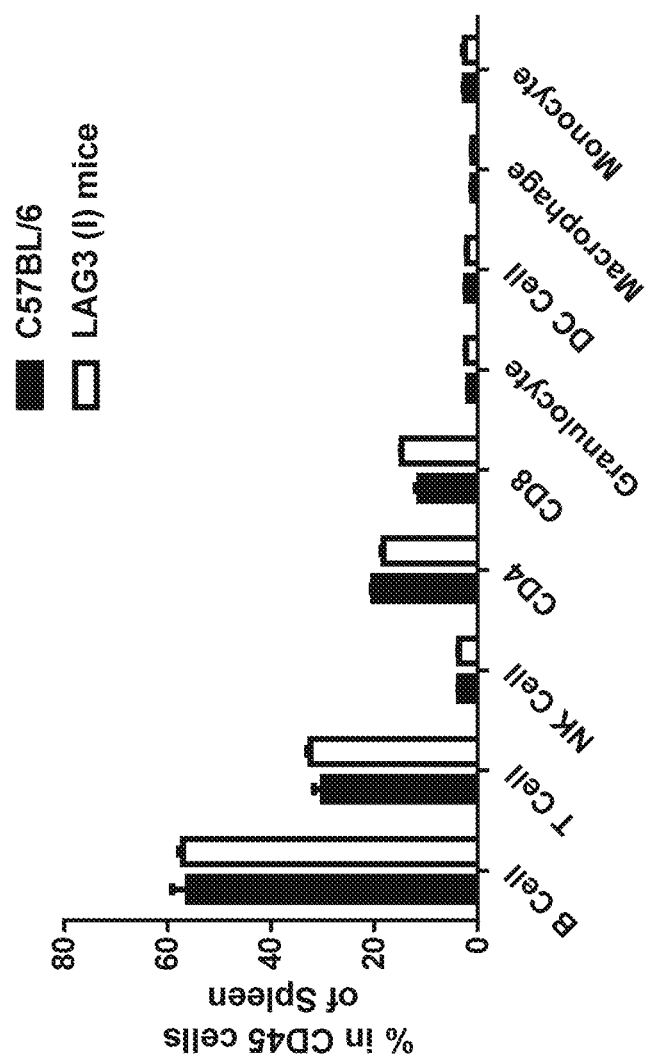
FIG. 28 is a histogram showing percentages of various immune cells in CD45+ cells from the spleen of wild-type C57BL/6 and LAG3 (l) gene humanized homozygous mice. The immune cells included: B cell, T cell, NK cell, CD4 cell, CD8 cell, granulocyte, DC cell, microphage and monocyte.
Figure 29:
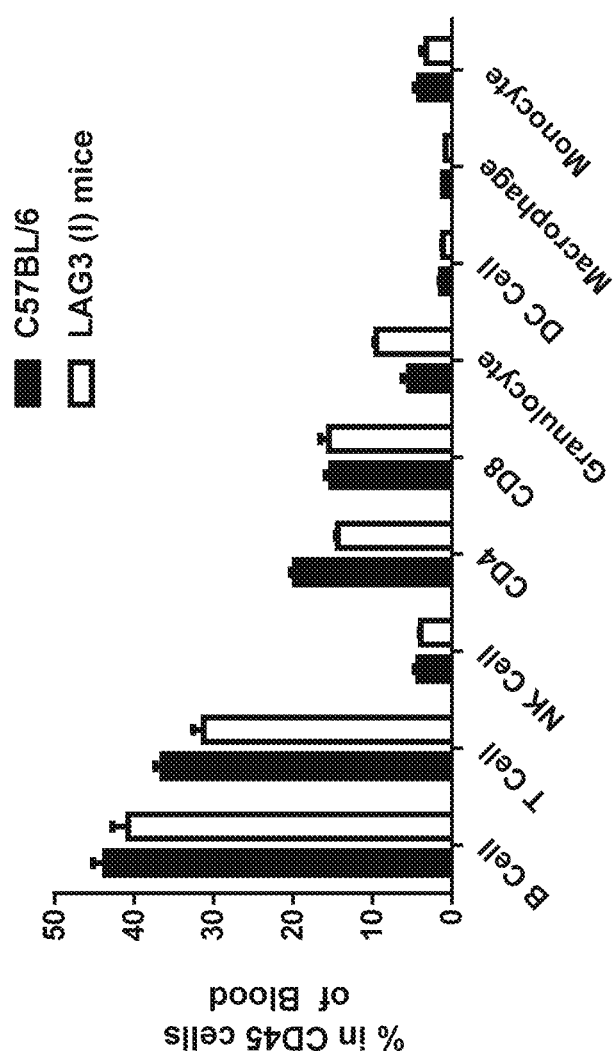
FIG. 29 is a histogram showing percentages of various immune cells among CD45+ cells from the peripheral blood of wild-type C57BL/6 and LAG3 (l) gene humanized homozygous mice. The immune cells included: B cell, T cell, NK cell, CD4 cell, CD8 cell, granulocyte, DC cell, microphage and monocyte.
Figure 30:
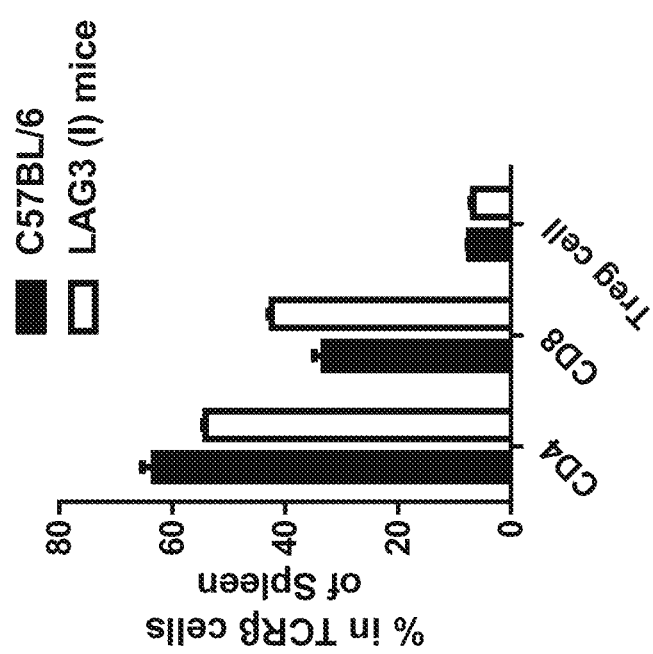
FIG. 30 is a histogram showing percentages of CD4, CD8 and Treg cells among TCRβ+ cells from the spleen of wild-type C57BL/6 and LAG3 (l) gene humanized homozygous mice.
Figure 31:
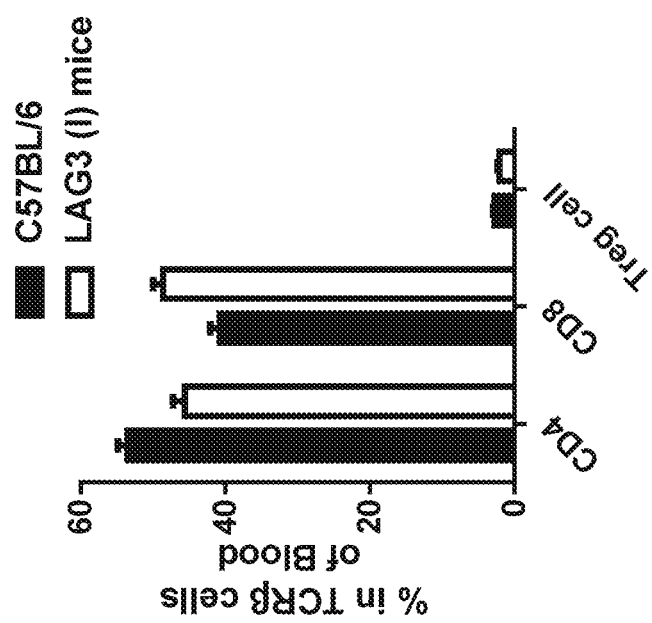
FIG. 31 is histogram showing percentages of CD4, CD8 and Treg cells among TCRβ+ cells from the peripheral blood of wild-type C57BL/6 and LAG3 (l) gene humanized homozygous mice.

One homozygous mouse was selected (6 weeks old), and one wild-type C57BL/6 mouse was selected as a control. The mouse spleen cells were stimulated with anti-mouse CD3 antibody (mCD3) and then divided into three groups. Relatlimab or IgG4-kappa (isotype control) were added to two randomly selected groups, respectively. Human IgG4 was added as a control. The cells and the antibodies were incubated for 30 minutes. After the incubation, Alexa Fluor® 647 AffiniPure F(ab')2 Fragment Goat Anti-Human IgG, Fcγ fragment specific (anti-hIgG Alexa Fluor 647), and murine T cell surface antibody FITC anti-Mouse TCR β Chain (mTcRβ FITC) were simultaneously used to stain T cells. The stained cells were washed with PBS. Protein expression was determined by flow cytometry analysis. Compared with the control groups (FIGS. 26A-26D), the human LAG3 antibody Relatlimab (FIGS. 26E-26F) exhibited good binding to the activated T cells from humanized LAG3 homozygous mice (LAG3 (s)).

Figure 14A:
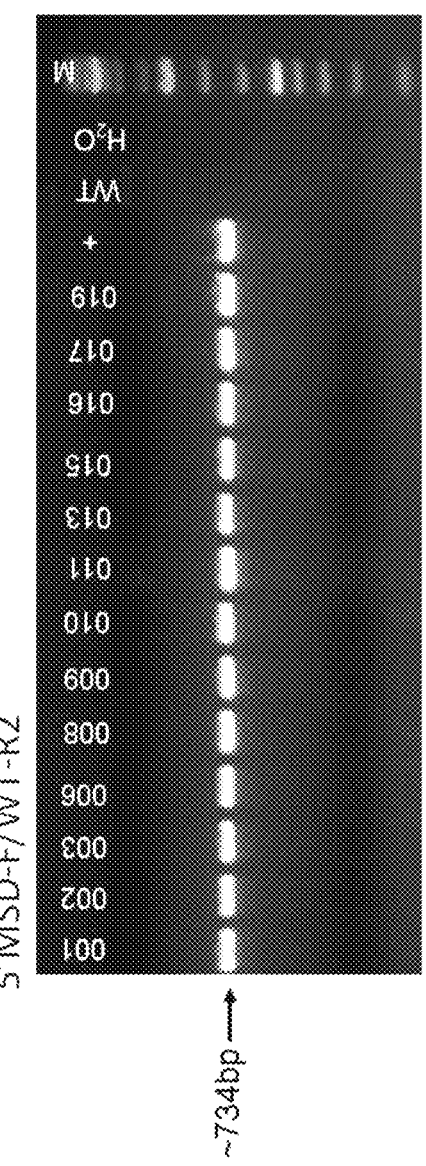
FIG. 14A shows PCR identification results of samples collected from tails of LAG-3 gene knockout mice. Primer pairs 5'MSD-F and WT-R2 were used for amplification. WT is wild-type. $H_2O$ is a blank control, + is a positive control and M is the Marker.
Figure 14B:
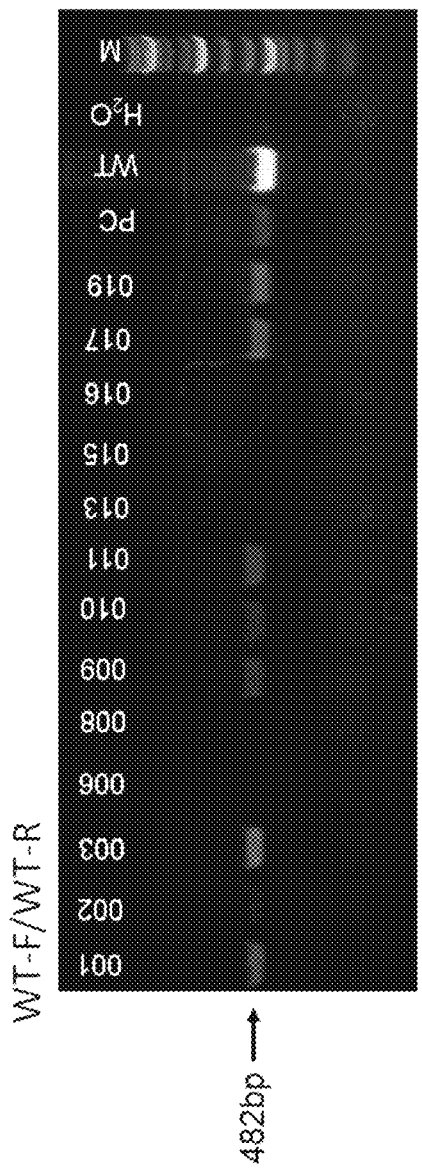
FIG. 14B shows PCR identification results of samples collected from tails of LAG-3 gene knockout mice. Primer pairs WT-F and WT-R were used for amplification. WT is wild-type. $H_2O$ is a blank control, + is a positive control and M is the Marker.

In addition, due to the double-strand break of genomic DNA caused by cleavage of Cas9, the insertion/deletion mutation is randomly generated by repairing through chromosomal homologous recombination. The method herein can also generate LAG3 knockout mice. Gene deletion can be detected by routine PCR method. The results of the identification are shown in FIGS. 14A-14B. Regarding FIGS. 14A-14B, mice with labels 001, 002, 003, 009, 010, 011, 017, and 019 were heterozygous knockout mice. Mice with labels 006, 008, 013, 015, and 016 were homozygous knockout mice. PCR analysis was performed using the following primers:

```
5' MSD-F:
                                        (SEQ ID NO: 63)
5'-GCTTTGGGAAGCTCCAGGTAAG-3'

WT-R2:
                                        (SEQ ID NO: 64)
5'-AGACAGCAGCTAAAAGATGCCCAG-3'

WT-F:
                                        (SEQ ID NO: 65)
5'-CTCCCTTCAACAGGGAGGCATGAT-3'

WT-R:
                                        (SEQ ID NO: 66)
5'-ATAACTACCCCTGTCCCCACTTCCG-3'
```

Example 2: LAG3 Gene Humanized Mice with Different Targeting Strategies

Gene humanization can be achieved to various degrees by different replacement strategies. The animals described herein can be prepared through various gene editing techniques, including but not limited to: gene homologous recombination on embryonic stem cells (ES), zinc finger nuclease (ZFN), transcriptional activator-like effector factor nuclease (TALEN), homing endonuclease (megakable base ribozyme), or other techniques.

To make a humanized mouse LAG3 locus as shown in FIG. 3, a targeting strategy shown in FIG. 15 was designed. Mouse and human LAG3 DNA were obtained using bacterial artificial chromosomes (BAC) RP23-121J20 and RP11-578M14, respectively. The targeting vector shown in FIG. 15 contains a 5' homologous arm (SEQ ID NO: 40), a 3' homologous arm (SEQ ID NO: 41), and a DNA fragment containing the human LAG3 sequence (abbreviated as "A2 fragment"., SEQ ID NO: 42). The 5' homologous arm is identical to the nucleotide sequence of 124915890-124910898 of the NCBI accession number NC_000072.6; the 3' homologous arm is the same as the nucleotide sequence of 124904008-124900076 of the NCBI accession number NC_000072.6; the A2 fragment is the same as nucleotide sequence 6773206-6777888 of the NCBI accession number NC_000012.12. The upstream of the DNA fragment containing the human LAG3 sequence was directly linked to the 5' homologous arm. The downstream junction to the mouse LAG3 locus was designed to be (SEQ ID NO: 67)
5'-GTTTCTCATCCTTGGTGTCCTTTCTCTGCTCCTTTTGG<u>TGACT</u><u>GGGGC</u>
CTTTGGCTTTCACTGGTGGAGAAAACAGGTGAGAC-3', wherein the last "T" of the sequence "<u>TGACT</u>" is the last nucleotide of the human sequence, and the first "G" of the sequence "<u>GGGGC</u>" is the first nucleotide of the mouse LAG3 locus. The mRNA sequence of the humanized mouse LAG3 and its encoded protein sequence are provided in SEQ ID NO: 43 and SEQ ID NO: 44, respectively.

The targeting vector also included an antibiotic resistance gene for positive clone screening (neomycin phosphotransferase encoding sequence Neo), and two Frt recombination sites on both sides of the antibiotic resistance gene that formed a Neo cassette. The junction between the 5' end of the Neo cassette and the mouse LAG3 locus was designed as (SEQ ID NO: 45)
5'-GGCCCACACCTAGCTCAGCTGCAC<u>TTCAGT</u><u>CTCGA</u>GGTCGACGGTATC
GATAAGCTTGATATCGAATTCCGAAGTTCCTATTCTCTAGAAAGTATAGGA
ACTTC-3', wherein the last "T" of the sequence "<u>TTCAGT</u>" is the last nucleotide of the mouse sequence, and the first "C" of the sequence "<u>CTCGA</u>" is the first nucleotide of the Neo cassette. The junction between the 3' end of the Neo cassette with the mouse LAG3 locus was designed to be (SEQ ID NO: 46)
5'-GTTCCTATTCTCTAGAAAGTATAGGAACTTCATCAGTCAGGTACATA
ATGGTGGATCCA<u>CTAGTC</u><u>ACTTG</u>TGCTCAGACCCCTGGCTACAGAGAA
GGAAAGC-3', wherein the last "C" of the sequence "<u>CTAGTC</u>" is the last nucleotide of the Neo cassette, and the "A" of the sequence "<u>ACTTG</u>" is the first nucleotide of the mouse sequence. In addition, a negative selection marker (a sequence encoding the diphtheria toxin A subunit (DTA)) was also inserted downstream of the 3' homologous arm of the recombinant vector.

Figure 16A:
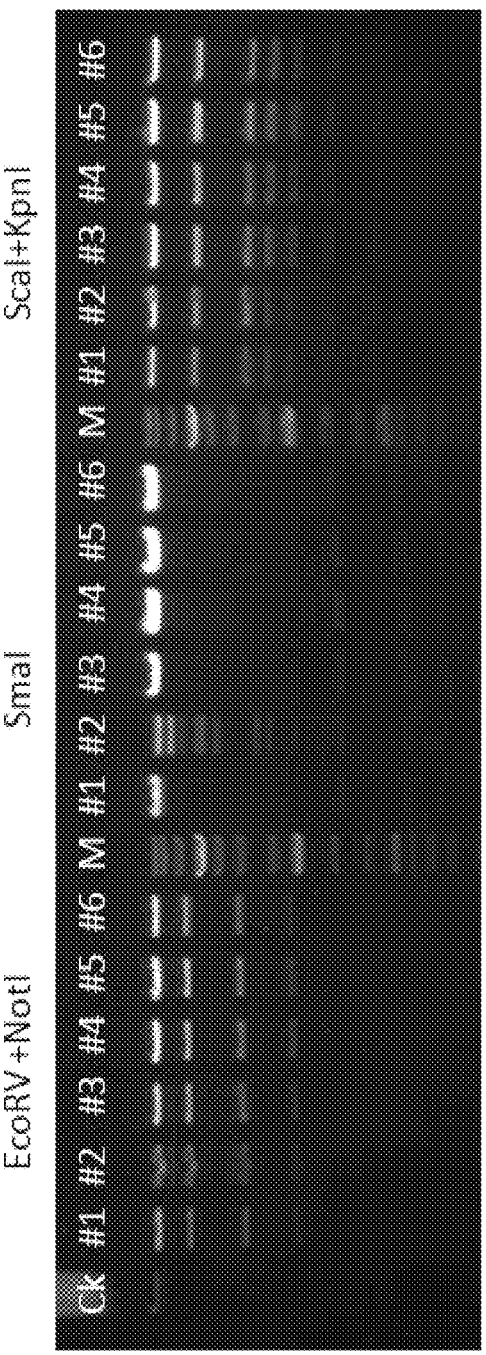
FIG. 16A shows the restriction enzymes digestion results of the recombinant vector by three sets of restriction enzymes. Ck indicates undigested plasmids, which were used as a control. M is the Marker. #1 to #6 are plasmid numbers.
Figure 16B:
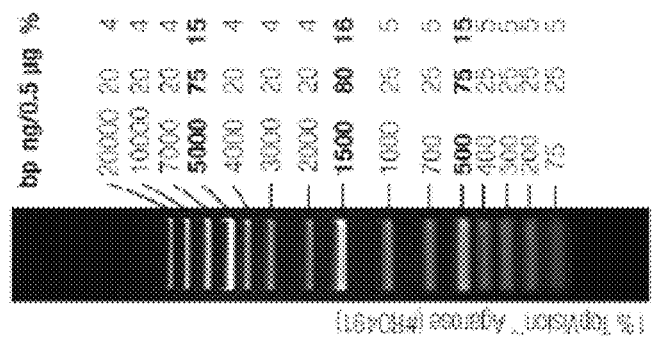
FIG. 16B shows DNA ladder for the Marker.
Figure 17A:
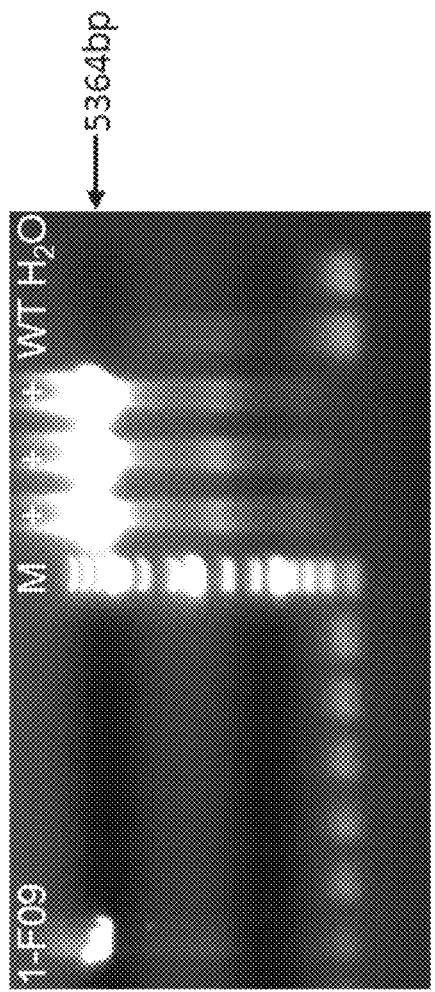
FIG. 17A shows PCR identification results of mouse embryonic stem cells. Primer pairs F1 and R1 were used for amplification. WT is wild-type. $H_2O$ is a blank control, + is a positive control and M is the Marker. Lanes labelled with clone numbers were positive clones, and lanes not labelled with clone numbers were negative.
Figure 17B:
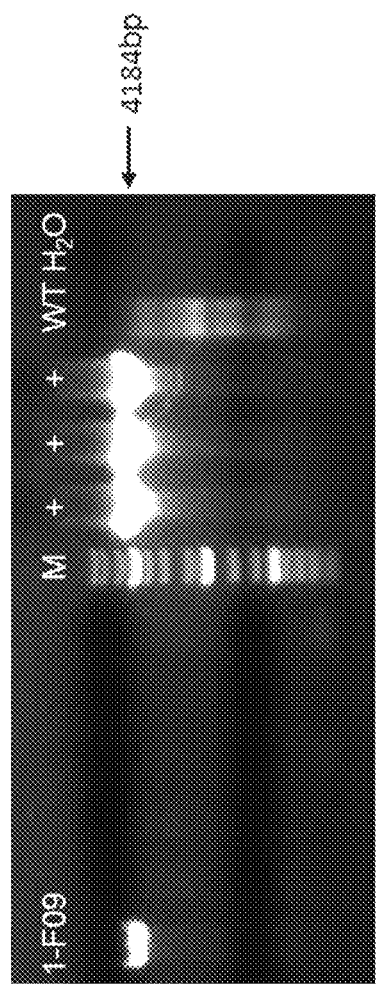
FIG. 17B shows PCR identification results of mouse embryonic stem cells. Primer pairs F2 and R2 were used for amplification. WT is wild-type. $H_2O$ is a blank control, + is a positive control and M is the Marker. Lanes labelled with clone numbers were positive clones, and lanes not labelled with clone numbers were negative.
Figure 18:
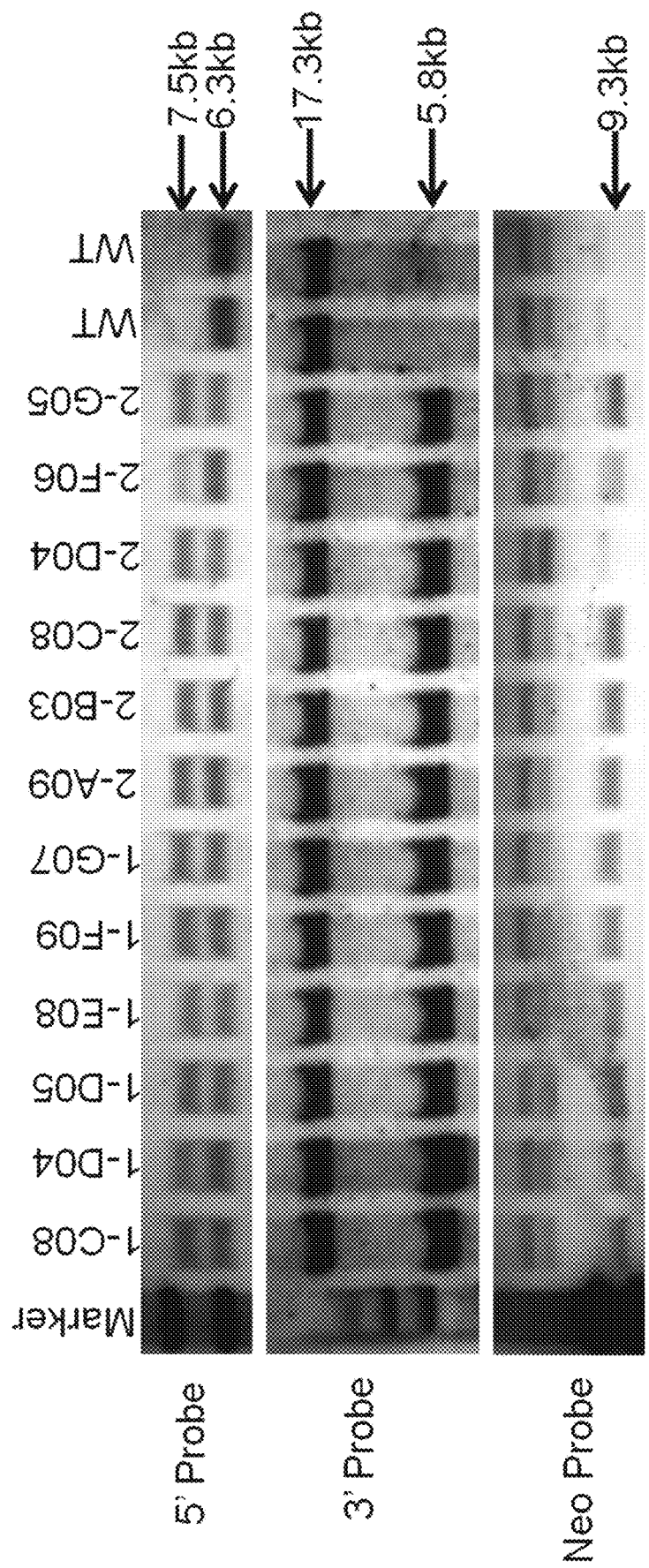
FIG. 18 is an image showing Southern blot results. WT indicates wild-type.

The targeting vectors were constructed. The constructed recombinant vectors were initially verified by sequencing or enzymatic digestion, and the verification results were shown in FIGS. 16A-16B. Three sets of restriction enzymes were used for verification. Among them, EcoRV+NotI should generate 11530 bp+5808 bp+2910 bp+1570 bp fragments; SmaI should generate 10959 bp+9297 bp+910 bp+414 bp+238 bp fragments; and ScaI+KpnI should generate 10358 bp+4596 bp+2294 bp+1769 bp+1359 bp+916 bp+526 bp fragments. The results of the enzyme digestion showed that except for the #2 clone, the rest were in line with expectations. Among them, plasmid #4 and #5 were further confirmed by sequencing. The correct recombinant vector was electroporated and transfected into embryonic stem cells of C57BL/6 mice. The positive selectable marker gene was used to screen the cells, and the integration of exogenous genes was confirmed by PCR and Southern Blot. PCR and Southern Blot results (digested with BamHI or AseI or SspI, respectively, and hybridized with 3 probes) for some of the clones were shown in FIGS. 17A-17B and 18. FIGS. 17A-17B showed that cells numbered 1-F09 were positive clones, and the remaining unlabeled lanes were negative clones. The Southern Blot test results in FIG. 18 indicated that among the 12 clones that were identified as positive by PCR, 9 clones (1-008, 1-D05, 1-E08, 1-F09, 1-G07, 2-A09, 2-B03, 2-008 and 2-G05) were identified as positive heterozygous clones and no random insertions were detected.

The PCR assay was performed using the following primers:

F:
(SEQ ID NO: 47)
5'-GTAATACAAGTGCCCAAACCCACCA-3',

R:
(SEQ ID NO: 48)
5'-CGGGTGTGGGGTTGAGTGCT-3'.

Southern Blot assay was performed using the following probes:

5' Probe:
F:
(SEQ ID NO: 49)
5'-ATGTGTGAGTTGGTGTTAGCCTGGG-3',

R:
(SEQ ID NO: 50)
5'-GACACTCCACTCCCTTCTCCCTTCA-3';

3' Probe:
F:
(SEQ ID NO: 51)
5'-ACTCCTATAATGAGGTGAGAGGCAG-3',

R:
(SEQ ID NO: 52)
5'-GCCCCGCTGGGATTTAGGACAGCAAC-3';

Neo Probe:
F:
(SEQ ID NO: 53)
5'-GGATCGGCCATTGAACAAGATGG-3',

R:
(SEQ ID NO: 54)
5'-CAGAAGAACTCGTCAAGAAGGCG-3'.

Figure 19:
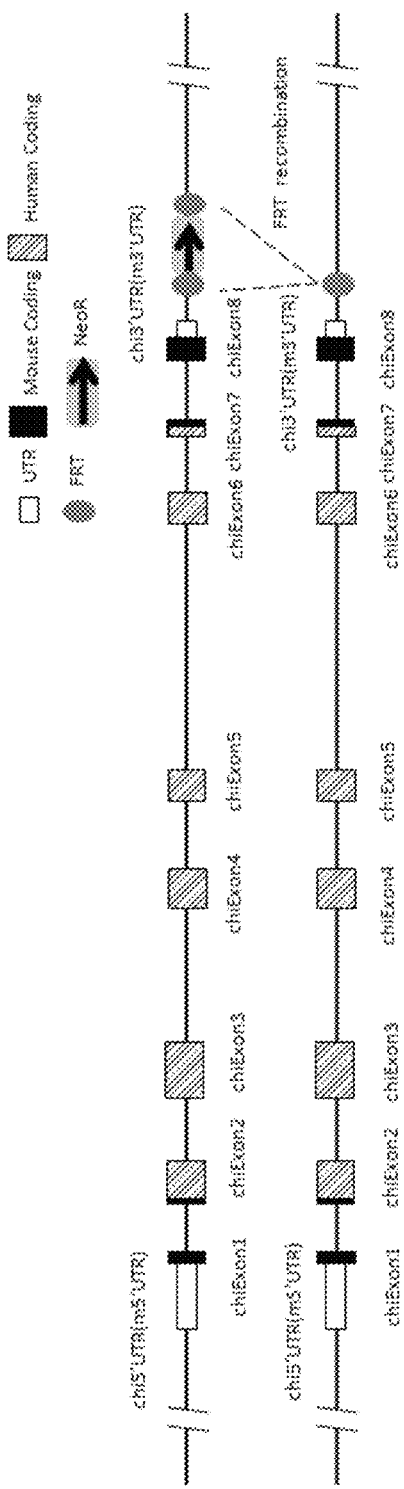
FIG. 19 is a schematic diagram showing the FRT recombination process that removes NeoR.

The positive clones from the screening (black mice) were introduced into isolated blastocysts (white mice), and the obtained chimeric blastocysts were transferred to the culture medium for a short-term culture and then transplanted to the fallopian tubes of the recipient mother (white mice) to produce the F0 chimeric mice (black and white). The F2 generation homozygous mice were obtained by backcrossing the F0 generation chimeric mice with wild-type mice to obtain the F1 generation mice, and then mating the F1 generation heterozygous mice with each other. The positive mice were also mated with the Flp tool mice to remove the positive selectable marker gene (the process was shown in FIG. 19), and then the humanized LAG3 homozygous mice expressing humanized LAG3 protein can be obtained by mating with each other. The genotype of the progeny mice was identified by PCR, and the results for the F1 generation mice (Neo-removed) are shown in FIGS. 20A-20D, wherein the mouse with number F1-2 was a positive heterozygous mouse.

The following primers were used in PCR:

```
WT-F:
                                  (SEQ ID NO: 55)
5'-GCCAGGGCATTTCTCTATTCTCCAATC-3',

WT-R:
                                  (SEQ ID NO: 56)
5'-GAGGTGGGGCACTACAGGATGC-3',

Mut-R:
                                  (SEQ ID NO: 57)
5'-CGGGTGTGGGGTTGAGTGCT-3';

Frt-F:
                                  (SEQ ID NO: 58)
5'-GACCTCCGTAATCCTTTCCCCAT-3',
```

-continued
```
Frt-R:
                                  (SEQ ID NO: 59)
5'-TTCTGGATTTCACATGGGTGGTGT-3';

Flp-F2:
                                  (SEQ ID NO: 60)
5'-GACAAGCGTTAGTAGGCACATATAC-3',

Flp-R2:
                                  (SEQ ID NO: 61)
5'-GCTCCAATTTCCCACAACATTAGT-3'.
```

This indicates that the present method can be used to generate genetically engineered LAG3 humanized mice (hereinafter referred to as B-hLAG-3 or LAG3 (1)) with no random insertions.

Similarly, the expression of the humanized LAG3 protein in these mice were determined by flow cytometry (FIGS. 21A-21H). The binding of the humanized LAG3 with the antibody Relatlimab was shown in FIGS. 27A-27F. The results were similar to those of LAG3(s) mice. No significant differences were detected. Further, the immune cells of the mouse peripheral blood and spleen were also examined, and no significant difference was observed compared to the wild-type mice (FIGS. 28-31). The results indicated that the humanized mice were grossly normal.

Example 3: Pharmacological Validation of LAG3 Gene Humanized Mouse Model

The humanized LAG3 heterozygotes prepared by the gene editing strategies of FIG. 2 or FIG. 3 can be mated to each other to obtain homozygotes.

The LAG3 (s) humanized homozygous mice (4-6 weeks) were subcutaneously inoculated with mouse colon cancer cell line MC38. After the tumor volume reached about 100 mm$^3$, they were randomly divided into a control group or a treatment group (n=8/group). The treatment group was administrated with a randomly selected anti-human LAG3 monoclonal antibody (AB1, obtained by immunizing mice using routine methods, see Murphy et al., Janeway's immunobiology (9th Edition). Garland Science, 2016) by intraperitoneal injection. The dosage was 10 mg/kg, and the control group was injected with saline solution. The frequency of administration was twice a week for a total of 6 times. Tumor volume was measured twice a week, and euthanasia was performed when the tumor volume in a single mouse reached 3000 mm$^3$ after inoculation.

Some data and analysis results of each experiment are listed in Table 5. The table shows the tumor volume at the time of grouping and 14 days after grouping, the tumor volume at the end of the experiment, the survival ratio, the tumor free cases and Tumor Growth Inhibition value ($TGI_{TV}$).

TABLE 5

| | Tumor Volume (mm$^3$) | | | Tumor | | | P value | |
| | Day 0 | Day 14 | Day 21 | Survival | Free | $TGI_{TV}$% | Body weight | Tumor Volume |
|---|---|---|---|---|---|---|---|---|
| Control Group G1 | 126 ± 4 | 1032 ± 69 | 2514 ± 280 | 8/8 | 0/8 | N/A | N/A | N/A |
| Treatment Group G2 | 126 ± 5 | 704 ± 143 | 1455 ± 256 | 8/8 | 0/8 | 44.35% | 0.599 | 0.015 |

Figure 22:
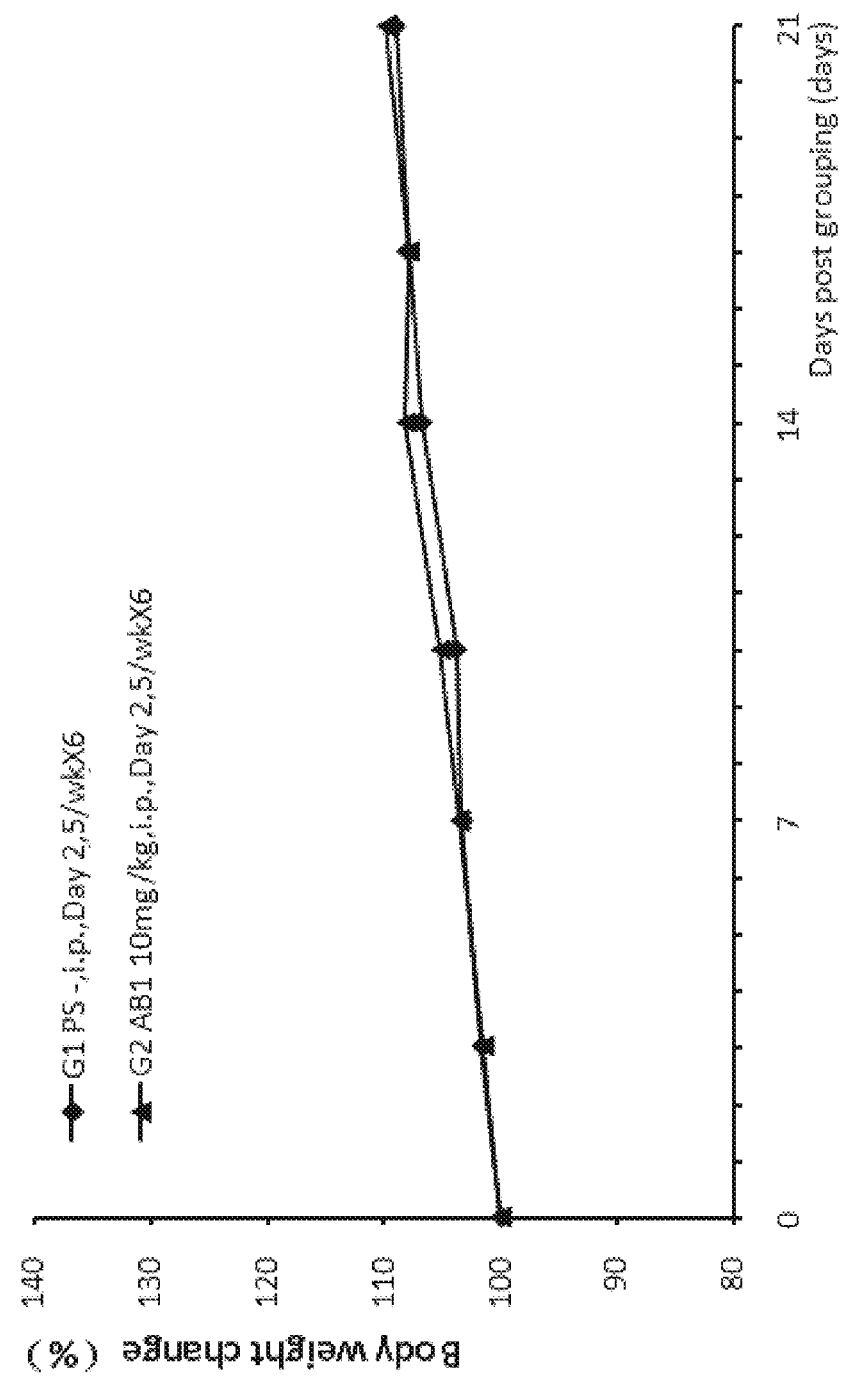
FIG. 22 shows the average body weight of humanized LAG3 gene homozygous mice that were injected with mouse colon cancer cells MC38 and were treated with an anti-human LAG3 antibody.
Figure 23:
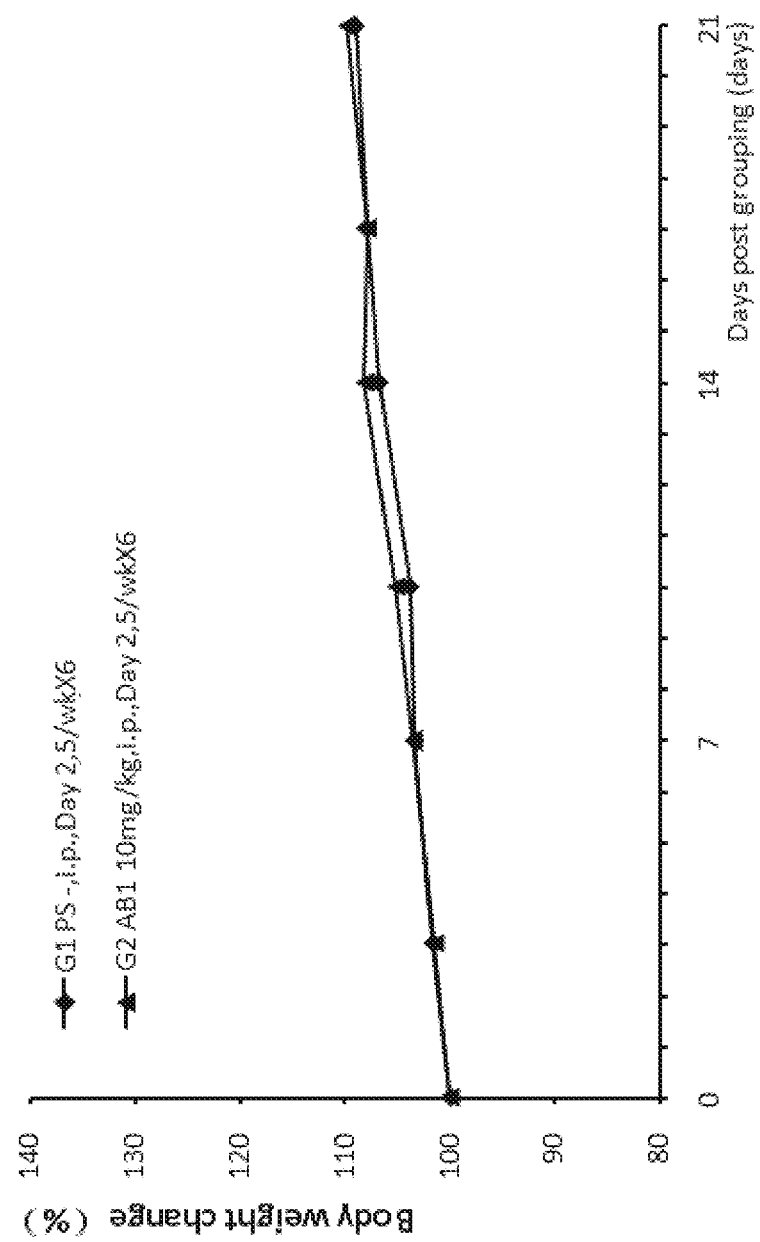
FIG. 23 shows the average body weight change of humanized LAG3 gene homozygous mice that were injected with mouse colon cancer cells MC38 and were treated with an anti-human LAG3 antibody.
Figure 24:
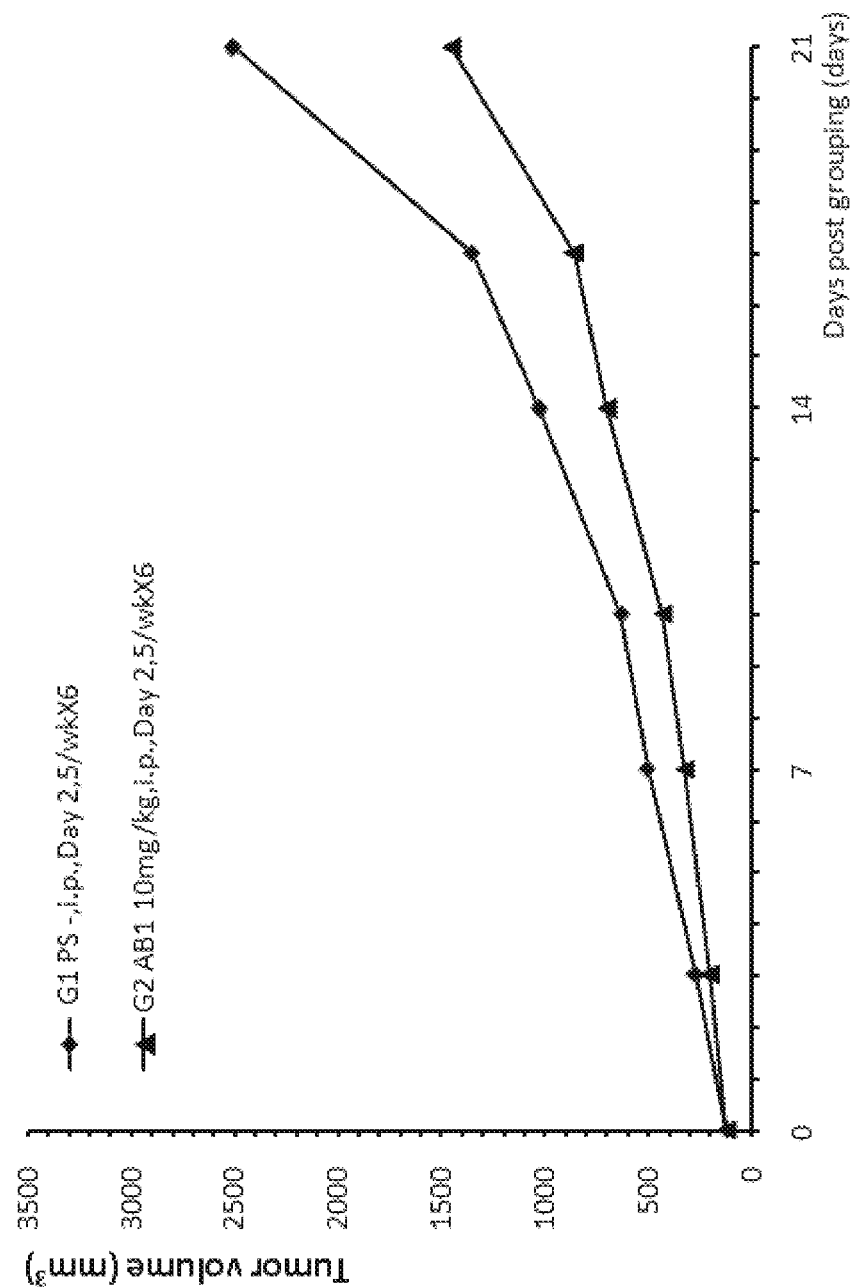
FIG. 24 shows the average tumor volume of humanized LAG3 gene homozygous mice that were injected with mouse colon cancer cells MC38 and were treated with an anti-human LAG3 antibody.

Overall, the animals in each group were healthy during the experimental period. At the end of each experiment, the body weights of all the treatment and control group mice increased. No significant differences between the groups were detected. This indicated that the anti-hLAG3 antibody was well tolerated by the animal. The average weight gains of the treatment group (G2) and the control group (G1) did not differ significantly during the whole experimental period (FIGS. 22-23), indicating that the antibody did not have obvious toxic effects on animals. As shown in FIG. 24, the tumor volume in the treatment group was much smaller than that of the control group, indicating that this anti-human LAG3 monoclonal antibody had some effects in inhibiting tumor growth. This demonstrated that the humanized LAG3 mice prepared by the method herein can be used for screening anti-human LAG3 antibody or determining in vivo drug efficacy.

Example 4: Preparation and Verification of Mice with Two or More Humanized Genes Mice with the humanized LAG3 gene (e.g., animal model with humanized LAG3 prepared using the methods as described in the present disclosure) can also be used to prepare an animal model with double-humanized or multi-humanized genes. As shown in Example 1 or Example 2, the fertilized egg cell or embryonic stem cell used in the microinjection and embryo transfer process can be selected from other genetically modified mice, so as to obtain double- or multiple-gene modified mouse models. The fertilized eggs of LAG3 humanized mice can also be further genetically engineered to produce mouse lines with one or more humanized or otherwise genetically modified mouse models. In addition, the humanized LAG3 animal model homozygote or heterozygote can be mated with other genetically modified homozygous or heterozygous animal models, and the progeny can be screened. According to the Mendel's law, there is a chance to obtain the double-gene or multiple-gene modified heterozygous animals, and then the heterozygous animals can be mated with each other to finally obtain the double-gene or multiple-gene modified homozygotes. These double- or multi-gene modified mice can be used to evaluate the in vivo efficacy of human LAG3-targeting molecules (e.g., LAG3 modulators).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A genetically-modified rodent whose genome comprises at least one chromosome comprising a sequence encoding a chimeric Lymphocyte-associated gene 3 (LAG3) protein, wherein the sequence comprises a humanized LAG3 exon 2, a human LAG3 exon 3, a human LAG3 exon 4, a human LAG3 exon 5, a human LAG3 exon 6, a humanized LAG3 exon 7, and an endogenous LAG3 exon 8; wherein the rodent has one or more cells expressing the chimeric LAG3 protein, wherein an anti-human LAG3 antibody can bind to the expressed chimeric LAG3 protein and block the interaction of the chimeric LAG3 protein with a LAG3 ligand, thereby increasing immune response, wherein the chimeric LAG3 protein comprises the amino acid sequence of SEQ ID NO: 44.

2. The rodent of claim 1, wherein the sequence encoding the chimeric LAG3 protein is operably linked to an endogenous regulatory element at the endogenous LAG3 gene locus in the at least one chromosome.

3. The rodent of claim 1, wherein the rodent is a mouse.

4. The rodent of claim 1, wherein the rodent does not express an endogenous LAG3 protein.

5. The rodent of claim 1, wherein the one or more cells comprise activated T cells, natural killer cells, or regulatory T cells (Tregs).

6. A genetically-modified rodent, wherein the genome of the rodent comprises a replacement of a nucleotide sequence comprising a contiguous sequence starting from within exon 2 and ending within exon 7 of an endogenous LAG3 gene with a nucleotide sequence comprising a contiguous sequence starting from within exon 2 and ending within exon 7 of a human LAG3 gene at an endogenous LAG3 gene locus thereby generating a chimeric LAG3 gene, wherein the rodent has one or more cells expressing a chimeric LAG3 protein encoded by the chimeric LAG3 gene, wherein an anti-human LAG3 antibody can bind to the expressed chimeric LAG3 protein and block the interaction of the chimeric LAG3 protein with a LAG3 ligand, thereby increasing immune response, wherein the chimeric LAG3 protein comprises the amino acid sequence of SEQ ID NO: 44.

7. The rodent of claim 6, wherein the replaced nucleotide sequence comprises a sequence encoding the extracellular region of LAG3.

8. The rodent of claim 6, wherein the rodent is homozygous with respect to the chimeric LAG3 gene.

9. The rodent of claim 1, wherein the rodent further comprises a sequence encoding an additional human or chimeric protein.

10. The rodent of claim 9, wherein the additional human or chimeric protein is programmed cell death protein 1 (PD-1), cytotoxic T-lymphocyte-associated protein 4 (CTLA-4), B And T Lymphocyte Associated (BTLA), Programmed Cell Death 1 Ligand 1 (PD-L1), CD27, CD28, CD40, CD47, CD137, CD154, T-Cell Immunoreceptor With Ig And ITIM Domains (TIGIT), T-cell Immunoglobulin and Mucin-Domain Containing-3 (TIM-3), Glucocorticoid-Induced TNFR-Related Protein (GITR), Signal regulatory protein a(SIRPα) or TNF Receptor Superfamily Member 4 (0X40).

11. A method of determining effectiveness of an anti-LAG3 antibody for treating cancer, comprising:
administering the anti-LAG3 antibody to the rodent of claim 1, wherein the rodent has a tumor; and
determining inhibitory effects of the anti-LAG3 antibody to the tumor.

12. The method of claim 11, wherein the tumor comprises one or more cancer cells that are injected into the rodent.

13. A genetically-modified rodent whose genome comprises at least one chromosome comprising a sequence encoding a chimeric LAG3 protein, wherein the chimeric LAG3 protein comprises the amino acid sequence of SEQ ID NO: 9, wherein the rodent has one or more cells expressing the chimeric LAG3 protein, wherein an anti-human LAG3 antibody can bind to the expressed chimeric LAG3 protein and block the interaction of the chimeric LAG3 protein with a LAG3 ligand, thereby increasing immune response.

14. The rodent of claim 13, wherein the rodent is a mouse.

15. The rodent of claim 1, wherein the chimeric LAG3 protein comprises a chimeric LAG3 transmembrane region.

* * * * *

UNITED STATES PATENT AND TRADEMARK OFFICE
CERTIFICATE OF CORRECTION

PATENT NO. : 11,564,381 B2
APPLICATION NO. : 17/009410
DATED : January 31, 2023
INVENTOR(S) : Yuelei Shen et al.

Page 1 of 1

It is certified that error appears in the above-identified patent and that said Letters Patent is hereby corrected as shown below:

On the Title Page

Column 2 (Item (56) Other Publications), in Line 18, delete "Embiyonic" and insert -- Embryonic --;

In the Claims

In Column 104, Line 10, in Claim 10, delete "a(SIRPα)" and insert -- α (SIRPα) --;

In Column 104, Line 11, in Claim 10, delete "(0X40)" and insert -- (OX4O) --.

Signed and Sealed this
Seventh Day of March, 2023

Katherine Kelly Vidal
*Director of the United States Patent and Trademark Office*

SEQUENCE LISTING

```
<160> NUMBER OF SEQ ID NOS: 75

<210> SEQ ID NO 1
<211> LENGTH: 2020
<212> TYPE: DNA
<213> ORGANISM: Mus musculus

<400> SEQUENCE: 1
gggcagtggg gaggagaagc agaaggactg ggtctggagg agcagctcaa gttctagcta      60
gctgcagtgg gtttgcctgc actctgctct gggtcccagc ccgggcctct gatcattatc     120
catcctgctg tctccagtcc ccactcctgg ggcgtcctct tcaccctaca ttctttccct     180
ccgcctcacc tcctccttgt agaacttctc tctctctctc tctctctctc tctctctctc     240
tctctctctc tctgtgtgtg tgtgtgtgtc tgtctgtctg tctgtctctc tctcctccca     300 ggacttttt ctaacctccc ttggagggct ggggaggccc gggccataga ggagatgagg      360
gaggacctgc tccttggctt tttgcttctg ggactgcttt gggaagctcc agttgtgtct     420
tcagggcctg ggaaagagct ccccgtggtg tgggcccagg agggagctcc cgtccatctt     480
ccctgcagcc tcaaatcccc caacctggat cctaactttc tacgaagagg aggggttatc     540
tggcaacatc aaccagacag tggccaaccc actcccatcc cggcccttga ccttcaccag     600
gggatgccct cgcctagaca acccgcaccc ggtcgctaca cggtgctgag cgtggctcca     660
ggaggcctgc gcagcgggag gcagccctg catccccacg tgcagctgga ggagcgcggc      720
ctccagcgcg gggacttctc tctgtggttg cgcccagctc tgcgcaccga tgcgggcgag     780
taccacgcca ccgtgcgcct cccgaaccgc gccctctcct gcagtctccg cctgcgcgtc     840
ggccaggcct cgatgattgc tagtccctca ggagtcctca agctgtctga ttgggtcctt     900
ttgaactgct ccttcagccg tcctgaccgc ccagtctctg tgcactggtt ccagggccag     960
aaccgagtgc ctgtctacaa ctcaccgcgt cattttttag ctgaaacttt cctgttactg    1020
ccccaagtca gcccctgga ctctgggacc tggggctgtg tcctcaccta cagagatggc     1080
ttcaatgtct ccatcacgta caacctcaag gttctgggtc tggagcccgt agccctctg     1140 acagtgtacg ctgctgaagg ttctagggtg gagctgccct gtcatttgcc cccaggagtg    1200
gggacccctt ctttgctcat tgccaagtgg actcctcctg gaggaggtcc tgagctcccc    1260
gtggctggaa agagtggcaa ttttacccct caccttgagg ctgtgggtct ggcacaggct    1320
gggacctaca cctgtagcat ccatctgcag ggacagcagc tcaatgccac tgtcacgttg    1380
gcggtcatca cagtgactcc caaatccttc gggttacctg gctccgggg gaagctgttg     1440 tgtgaggtaa ccccggcatc tggaaaggaa agatttgtgt ggcgtcccct gaacaatctg    1500
tccaggagtt gcccgggccc tgtgctggag attcaggagg ccaggctcct tgctgagcga    1560
tggcagtgtc agctgtacga gggccagagg cttcttggag cgacagtgta cgccgcagag    1620
```

-continued

```
tctagctcag gcgcccacag tgctaggaga atctcaggtg accttaaagg aggccatctc     1680
gttctcgttc tcatccttgg tgccctctcc ctgttccttt tggtggccgg ggcctttggc     1740
tttcactggt ggagaaaaca gttgctactg agaagatttt ctgccttaga acatgggatt     1800
cagccatttc cggctcagag aagatagag gagctggagc gagaactgga gacggagatg      1860
ggacaggagc cggagcccga gccggagcca cagctggagc cagagcccag gcagctctga     1920
cctggagccg aggcagccag caggtctcag cagctccgcc cgcccgcccg cccgcccgaa     1980
taaactccct gtcagcagca tcaaaaaaaa aaaaaaaaa                             2020
```

<210> SEQ ID NO 2
<211> LENGTH: 521
<212> TYPE: PRT
<213> ORGANISM: Mus musculus

<400> SEQUENCE: 2

```
Met Arg Glu Asp Leu Leu Gly Phe Leu Leu Gly Leu Leu Trp
1               5                   10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Val Ile Trp Gln
        50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300
```

```
Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
            325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
            355                 360                 365

Ser Gly Lys Glu Arg Phe Val Trp Arg Pro Leu Asn Asn Leu Ser Arg
370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
            405                 410                 415

Thr Val Tyr Ala Ala Glu Ser Ser Gly Ala His Ser Ala Arg Arg
            420                 425                 430

Ile Ser Gly Asp Leu Lys Gly His Leu Val Leu Val Leu Ile Leu
435                 440                 445

Gly Ala Leu Ser Leu Phe Leu Leu Val Ala Gly Ala Phe Gly Phe His
    450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Glu Leu Glu Arg
            485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
            515                 520

<210> SEQ ID NO 3
<211> LENGTH: 1995
<212> TYPE: DNA
<213> ORGANISM: Homo sapiens

<400> SEQUENCE: 3 acagggagtga aggcccagag accagcagaa cggcatccca gccacgacgg ccactttgct    60
ctgtctgctc tccgccacgg ccctgctctg ttccctggga caccccgcc cccacctcct    120 caggctgcct gatctgccca gctttccagc tttcctctgg attccggcct ctggtcatcc    180
ctccccaccc tctctccaag gccctctcct ggtctccctt cttctagaac cccttcctcc    240
acctccctct ctgcagaact tctcctttac cccccaccc ccaccactgc ccccttctct    300
tttctgacct ccttttggag ggctcagcgc tgcccagacc ataggagaga tgtgggaggc    360
tcagttcctg ggcttgctgt ttctgcagcc gctttgggtg gctccagtga agcctctcca    420
gccaggggct gaggtcccgg tggtgtgggc caggaggggg gctcctgccc agctcccctg    480
cagccccaca atccccctcc aggatctcag ccttctgcga agagcagggg tcacttggca    540
gcatcagcca gacagtggcc cgcccgctgc cgccccggc catccctgg ccccggccc    600 tcacccggcg gcgccctcct cctgggggcc caggccccgc cgctacacgg tgctgagcgt    660
gggtcccgga ggcctgcgca gcgggaggct gcccctgcag ccccgcgtcc agctggatga    720
gcgcggccgg cagcgcgggg acttctcgct atggctgcgc ccagcccggc gcgcggacgc    780
cggcgagtac cgcgccgcgg tgcacctcag ggaccgcgcc ctctcctgcc gcctccgtct    840
```

```
gcgcctgggc caggcctcga tgactgccag ccccccagga tctctcagag cctccgactg    900
ggtcattttg aactgctcct tcagccgccc tgaccgccca gcctctgtgc attggttccg    960
gaaccggggc cagggccgag tccctgtccg ggagtccccc catcaccact tagcggaaag   1020
cttcctcttc ctgccccaag tcagcccat ggactctggg ccctggggct gcatcctcac    1080
ctacagagat ggcttcaacg tctccatcat gtataacctc actgttctgg gtctggagcc   1140
cccaactccc ttgacagtgt acgctggagc aggttccagg gtggggctgc cctgccgcct   1200
gcctgctggt gtggggaccc ggtctttcct cactgccaag tggactcctc ctgggggagg   1260
ccctgacctc ctggtgactg gagacaatgg cgactttacc cttcgactag aggatgtgag   1320
ccaggcccag gctgggacct acacctgcca tatccatctg caggaacagc agctcaatgc   1380
cactgtcaca ttggcaatca tcacagtgac tcccaaatcc tttgggtcac ctggatccct   1440
ggggaagctg ctttgtgagg tgactccagt atctggacaa gaacgctttg tgtggagctc   1500
tctggacacc ccatcccaga ggagtttctc aggaccttgg ctggaggcac aggaggccca   1560
gctcctttcc cagccttggc aatgccagct gtaccagggg gagaggcttc ttggagcagc   1620
agtgtacttc acagagctgt ctagcccagt gcccaacgc tctgggagag ccccaggtgc    1680
cctcccagca ggccacctcc tgctgtttct catccttggt gtcctttctc tgctcctttt   1740
ggtgactgga gcctttggct ttcacctttg gagaagacag tggcgaccaa gacgattttc   1800
tgccttagag caagggattc accctccgca ggctcagagc aagatagagg agctggagca   1860
agaaccggag ccggagccgg agccggaacc ggagcccgag cccgagcccg agccggagca   1920
gctctgacct ggagctgagg cagccagcag atctcagcag cccagtccaa ataaactccc   1980
tgtcagcagc aaaaa                                                    1995

<210> SEQ ID NO 4
<211> LENGTH: 525
<212> TYPE: PRT
<213> ORGANISM: Homo sapiens

<400> SEQUENCE: 4

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
```

```
                    165                 170                 175
Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
            500                 505                 510

Glu Pro Glu Pro Glu Pro Glu Pro Glu Pro Glu Gln Leu
        515                 520                 525

<210> SEQ ID NO 5
<211> LENGTH: 869
<212> TYPE: DNA
<213> ORGANISM: Mus musculus

<400> SEQUENCE: 5
gaatcagccc cctcacactt tccactgcga agcgaaaccc cgcgccttgg tctgggggggg      60 cgggcagtgg ggaggagaag cagaaggact gggtctggag gagcagctca agttctagct     120
```

```
agctgcagtg ggtttgcctg cactctgctc tgggtccag  cccgggcctc tgatcattat      180
ccatcctgct gtctccagtc cccactcctg ggcgtcctc  ttcacccta  cattctttccc    240 tccgcctcac ctcctccttg tagaacttct ctctctctct  ctctctctct ctctctctct    300
ctctctctct ctctgtgtgt gtgtgtgtgt ctgtctgtct  gtctgtctct ctcctcctcc    360 aggaccttt  tctaacctcc cttggagggc tggggaggcc  cgggccatag aggagatgag    420
ggaggacctg ctccttggct ttttgcttct gggactgctt  tgggaagctc caggtaaggt    480
ggagagtcca gcagggacct ctatggctgt ctctttagct  gtggtgatat ccaatgctt    540 ttgttgaggg gaggggtgtg tgtgtgtgtg tgtgtgtgtg  ttttgagaca gggtttctt    600 gtgttgccct ggctgtcctg ggactggctc tgatgaccag  gctggccttg aatttatagt    660
gatccacttg cctctgcctc cccagtgctg ggattagagg  cgtgcaccat cactttgtat    720
aagggcagat cccaaagctg cctcagcctc ccttcaacag  ggaggcatga tgtttctttc    780
ttaggaaagc cagggcattt ctctattctc caatctcttg  gctcaatgcc cttggcctct    840
cttttgttcc actagttgtg tcttcaggg                                       869

<210> SEQ ID NO 6
<211> LENGTH: 1203
<212> TYPE: DNA
<213> ORGANISM: Mus musculus

<400> SEQUENCE: 6
gttctgggta actcttctaa gcagccttga ccacaacctt  cctgtcacc  acctctcctg      60 actcatgcat ggaccccaa  aactttctca gctgcgtgtg  gtctcactcc acatcacttt    120
gtttcagtgt ccaaaccatt ttctctctgg gcatctttta  gctgctgtct ctcttacttt    180 tatttatta  tttgtgtgtt tatttatta  ttttcatttt  agcgtgcgtt ggtgttttgc    240
ctgcatagat gtctgtgtca gggtattgga ttccctggaa  cttgacctac agacagtcat    300
gagataccat atgggtgctg ggaattgaac ccagctcctc  tggaaggaca gccagtgttc    360
taatctgcca tctctcactg tttatcccct ggctgttcag  cctcctgagc ctttggtctc    420
ttgctgcctc agtttcccta gtttctctgc tttgctctgt  ttctttctgt gttacagcca    480
aatgcctcct tccccttct  gccttacttc cttgatgtct  ccaccctctg gcccactgct    540
tacccttggt aacggcttgg cttttccttc ttctctccag  gtctggagcc cgtagccct    600 ctgacagtgt acgctgctga aggttctagg gtggagctgc  cctgtcattt gcccccagga    660
gtggggaccc cttctttgct cattgccaag tggactcctc  ctggaggagg tcctgagctc    720
cccgtggctg gaaagagtgg caatttacc  cttcaccttg  aggctgtggg tctggcacag    780
gctgggacct acacctgtag catccatctg cagggacagc  agctcaatgc cactgtcacg    840
ttggcggtca tcacaggtca gccacaggtg ggaatggaat  agtttccatc tcagggagaa    900
agaacagggt gggagtgttg gctgtcagag aggggtgtgt  gcattcgtgc gtgtgcgtgt    960
gcctgtgcgt gtgtgcgtgt gtgtgtgcgc gcgcgcatga  ccagtatatg ttcctcagca   1020
tgtatttgag gtcactggac aactctgtgg agttagttct  ctctaccac  ctttctctgg   1080 gttctagggt ttgcacagaa agcaccttt  tcctttagc   ttaggatggc cttgaactcc   1140
tgattctgct gcttacaagg cccaagtgct gggactagag  acatgtacta ctgtgcctgt   1200
caa                                                                  1203

<210> SEQ ID NO 7
```

<211> LENGTH: 1652
<212> TYPE: DNA
<213> ORGANISM: Homo sapiens

<400> SEQUENCE: 7

```
ccagggctg aggtcccggt ggtgtgggcc caggaggggg ctcctgccca gctcccctgc      60
agccccacaa tccccctcca ggatctcagc cttctgcgaa gagcaggggt cacttggcag     120
catcagccag acaggtatgc accccaaact tgggcaacag gacctccgaa tccagcactc     180
aaccccacac ccgtgccggt cctctgtccc ctgccctgag gtgtcactcc ctctgaagcc     240
agtgacccag tctccctgcc ctcgcttgca ccgttcctgc ccttgctctg caatcagcga     300
ccctcacgcc agcatccctt ctctccagaa gtggatgcgg ccagtccaac agaggggtcg     360
ggcgtgaggg gacggttggt ggtcaagaga actcttgggg cgggcttcct catcctcaac     420
gggtggctgc ctgcatcctc ccgggcttcc taccctggaa gcttctcaac tccattctct     480
ttcccgccca gtggcccgcc cgctgccgcc cccggccatc ccctggcccc cggccctcac     540
ccggcggcgc cctcctcctg ggggcccagg ccccgccgct acacggtgct gagcgtgggt     600
cccggaggcc tgcgcagcgg gaggctgccc ctgcagcccc gcgtccagct ggatgagcgc     660
ggccggcagc gcggggactt ctcgctatgg ctgcgcccag cccggcgcgc ggacgccggc     720
gagtaccgcg ccgcggtgca cctcagggac cgcgccctct cctgccgcct ccgtctgcgc     780
ctgggccagg cctcgagtat gtggggcggg acgatgggaa aagggctggg aggtgggtcc     840
ccatcccctg cctcccggga cgcaggaagg gctgggcag aggctgcgcc ctaggccctg      900
tcggagagct cccagaagag tagaggaagg gggtgggcgg cctgctggag tggaaggtgc     960
ccccgaagca cgtgtatggg gggccctgtg gagagattgt gtcaccccg agctcccctt     1020
ctcccaccca cgcggggagtg cccagaggga ggggagggg gggagagcat ggggctaaag    1080
tgattcattt cagatatctg tagctcaggg ggtgggcttc gcggggttcc aggccaggaa    1140
aacggcaagg gtggctgatg ccaagtaaac tccaggccag ggacggggaa agtggtcctg   1200
gggagtcttg gggatccact ttatgcacct ccaggtgctg gaagctgaga tggggagagg    1260
gtgatgtggg agaggagaag acaagtctaa agccaggtgc ctgtttccag gagcttccgg   1320
cttggcagcc ctgctgtgtt gggaaattgt ttccagtggg ctgatgaagt cttctttatc    1380
cttgcacagt gactgccagc ccccaggat ctctcagagc ctccgactgg gtcattttga    1440
actgctcctt cagccgccct gaccgccag cctctgtgca ttggttccgg aaccggggcc    1500
agggccgagt ccctgtccgg gagtccccc atcaccactt agcggaaagc ttcctcttcc    1560
tgccccaagt cagccccatg gactctgggc cctggggctg catcctcacc tacagagatg    1620
gcttcaacgt ctccatcatg tataacctca ct                                  1652
```

<210> SEQ ID NO 8
<211> LENGTH: 2038
<212> TYPE: DNA
<213> ORGANISM: Artificial Sequence
<220> FEATURE:
<223> OTHER INFORMATION: Humanized LAG-3 (short)

<400> SEQUENCE: 8

```
gggcagtggg gaggagaagc agaaggactg gtctggagg agcagctcaa gttctagcta      60
gctgcagtgg gtttgcctgc actctgctct gggtcccagc ccgggcctct gatcattatc     120
catcctgctt tctccagtcc ccactcctgg ggcgtcctct tcaccctaca ttctttccct    180
ccgcctcacc tcctccttgt agaacttctc tctctctctc tctctctctc tctctctctc   240
```

```
tctctctctc tctgtgtgtg tgtgtgtgtc tgtctgtctg tctgtctctc tcctcccca        300
ggacctttt ctaacctccc ttggagggct ggggaggccc gggccataga ggagatgagg         360
gaggacctgc tccttggctt tttgcttctg ggactgcttt gggaagctcc agttgtgtct        420
tcagggccag gggctgaggt cccggtggtg tgggcccagg aggggctcc tgcccagctc         480
ccctgcagcc ccacaatccc cctccaggat ctcagccttc tgcgaagagc agggtcact         540
tggcagcatc agccagacag tggcccgccc gctgccgccc ccggccatcc cctgccccc         600
ggccctcacc cggcggcgcc ctcctcctgg gggcccaggc cccgccgcta cacggtgctg        660
agcgtgggtc ccggaggcct gcgcagcggg aggctgcccc tgcagcccg cgtccagctg         720
gatgagcgcg gccggcagcg cggggacttc tcgctatggc tgcgcccagc ccggcgcgcg        780
gacgccggca gtaccgcgc gcggtgcac ctcaggacc gcgccctctc ctgccgcctc           840
cgtctgcgcc tgggccaggc ctcgatgact gccagcccc caggatctct cagagcctcc        900
gactgggtca ttttgaactg ctccttcagc cgccctgacc gcccagcctc tgtgcattgg        960
ttccggaacc ggggccaggg ccgagtccct gtccgggagt ccccccatca ccacttagcg       1020
gaaagcttcc tcttcctgcc ccaagtcagc cccatggact ctgggccctg ggctgcatc        1080
ctcacctaca gagatggctt caacgtctcc atcatgtata acctcactgt tctgggtctg      1140
gagcccgtag cccctctgac agtgtacgct gctgaaggtt ctagggtgga gctgccctgt      1200
catttgcccc caggagtggg gacccttct ttgctcattg ccaagtggac tcctcctgga        1260
ggaggtcctg agctccccgt ggctggaaag agtggcaatt ttaccttca ccttgaggct        1320
gtgggtctgg cacaggctgg gacctacacc tgtagcatcc atctgcaggg acagcagctc      1380
aatgccactg tcacgttggc ggtcatcaca gtgactccca atccttcgg gttacctggc        1440
tcccggggga gctgttgtg tgaggtaacc ccggcatctg gaaggaaag atttgtgtgg        1500
cgtcccctga caatctgtc caggagttgc ccgggccctg tgctggagat tcaggaggcc      1560
aggctccttg ctgagcgatg gcagtgtcag ctgtacgagg ccagaggct tcttggagcg      1620
acagtgtacg ccgcagagtc tagctcaggc gcccacagtg ctaggagaat ctcaggtgac     1680
cttaaaggag gccatctcgt tctcgttctc atccttggtg ccctctccct gttccttttg    1740
gtggccgggg cctttggctt tcactggtgg agaaaacagt tgctactgag aagattttct   1800
gccttagaac atgggattca gccatttccg gctcagagga agatagagga gctggagcga   1860
gaactggaga cggagatggg acaggagccg gagcccgagc cggagccaca gctggagcca    1920
gagcccaggc agctctgacc tggagccgag gcagccagca ggtctcagca gctccgcccg   1980
cccgccgcc cgcccgaata aactccctgt cagcagcatc aaaaaaaaaa aaaaaaa        2038
```

<210> SEQ ID NO 9
<211> LENGTH: 527
<212> TYPE: PRT
<213> ORGANISM: Artificial Sequence
<220> FEATURE:
<223> OTHER INFORMATION: Humanized LAG-3 (short)

<400> SEQUENCE: 9

```
Met Arg Glu Asp Leu Leu Leu Gly Phe Leu Leu Leu Gly Leu Leu Trp
 1               5                  10                  15

Glu Ala Pro Val Val Ser Ser Gly Pro Gly Ala Glu Val Pro Val Val
            20                  25                  30

Trp Ala Gln Glu Gly Ala Pro Ala Gln Leu Pro Cys Ser Pro Thr Ile
        35                  40                  45
```

```
Pro Leu Gln Asp Leu Ser Leu Leu Arg Arg Ala Gly Val Thr Trp Gln
    50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Ala Asp Ala
            130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
                180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
            210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Val Ala Pro Leu Thr Val Tyr Ala
            260                 265                 270

Ala Glu Gly Ser Arg Val Glu Leu Pro Cys His Leu Pro Pro Gly Val
            275                 280                 285

Gly Thr Pro Ser Leu Leu Ile Ala Lys Trp Thr Pro Pro Gly Gly Gly
            290                 295                 300

Pro Glu Leu Pro Val Ala Gly Lys Ser Gly Asn Phe Thr Leu His Leu
305                 310                 315                 320

Glu Ala Val Gly Leu Ala Gln Ala Gly Thr Tyr Thr Cys Ser Ile His
                325                 330                 335

Leu Gln Gly Gln Gln Leu Asn Ala Thr Val Thr Leu Ala Val Ile Thr
            340                 345                 350

Val Thr Pro Lys Ser Phe Gly Leu Pro Gly Ser Arg Gly Lys Leu Leu
            355                 360                 365

Cys Glu Val Thr Pro Ala Ser Gly Lys Glu Arg Phe Val Trp Arg Pro
370                 375                 380

Leu Asn Asn Leu Ser Arg Ser Cys Pro Gly Pro Val Leu Glu Ile Gln
385                 390                 395                 400

Glu Ala Arg Leu Leu Ala Glu Arg Trp Gln Cys Gln Leu Tyr Glu Gly
                405                 410                 415

Gln Arg Leu Leu Gly Ala Thr Val Tyr Ala Ala Glu Ser Ser Ser Gly
            420                 425                 430

Ala His Ser Ala Arg Arg Ile Ser Gly Asp Leu Lys Gly Gly His Leu
            435                 440                 445

Val Leu Val Leu Ile Leu Gly Ala Leu Ser Leu Phe Leu Leu Val Ala
            450                 455                 460
```

```
Gly Ala Phe Gly Phe His Trp Trp Arg Lys Gln Leu Leu Arg Arg
465                 470                 475                 480

Phe Ser Ala Leu Glu His Gly Ile Gln Pro Phe Pro Ala Gln Arg Lys
                485                 490                 495

Ile Glu Glu Leu Glu Arg Glu Leu Glu Thr Glu Met Gly Gln Glu Pro
                500                 505                 510

Glu Pro Glu Pro Glu Pro Gln Leu Gly Pro Glu Pro Arg Gln Leu
            515                 520                 525

<210> SEQ ID NO 10
<211> LENGTH: 23
<212> TYPE: DNA
<213> ORGANISM: Mus musculus

<400> SEQUENCE: 10
gttccactag ttgtgtcttc agg                                            23

<210> SEQ ID NO 11
<211> LENGTH: 23
<212> TYPE: DNA
<213> ORGANISM: Mus musculus

<400> SEQUENCE: 11
ggccctgaag acacaactag tgg                                            23

<210> SEQ ID NO 12
<211> LENGTH: 23
<212> TYPE: DNA
<213> ORGANISM: Mus musculus

<400> SEQUENCE: 12
accacgggga gctctttccc agg                                            23

<210> SEQ ID NO 13
<211> LENGTH: 23
<212> TYPE: DNA
<213> ORGANISM: Mus musculus

<400> SEQUENCE: 13
ctagttgtgt cttcagggcc tgg                                            23

<210> SEQ ID NO 14
<211> LENGTH: 23
<212> TYPE: DNA
<213> ORGANISM: Mus musculus

<400> SEQUENCE: 14
gcctgggaaa gagctccccg tgg                                            23

<210> SEQ ID NO 15
<211> LENGTH: 23
<212> TYPE: DNA
<213> ORGANISM: Mus musculus

<400> SEQUENCE: 15
cctcctgggc ccacaccacg ggg                                            23

<210> SEQ ID NO 16
<211> LENGTH: 23
<212> TYPE: DNA
<213> ORGANISM: Mus musculus

<400> SEQUENCE: 16
```

```
ggaaagagct ccccgtggtg tgg                                              23

<210> SEQ ID NO 17
<211> LENGTH: 23
<212> TYPE: DNA
<213> ORGANISM: Mus musculus

<400> SEQUENCE: 17
tgacgcggtg agttgtagac agg                                              23

<210> SEQ ID NO 18
<211> LENGTH: 23
<212> TYPE: DNA
<213> ORGANISM: Mus musculus

<400> SEQUENCE: 18
tgtagacagg cactcggttc tgg                                              23

<210> SEQ ID NO 19
<211> LENGTH: 23
<212> TYPE: DNA
<213> ORGANISM: Mus musculus

<400> SEQUENCE: 19
ctccatcacg tacaacctca agg                                              23

<210> SEQ ID NO 20
<211> LENGTH: 23
<212> TYPE: DNA
<213> ORGANISM: Mus musculus

<400> SEQUENCE: 20
agtcctcaag ctgtctgatt ggg                                              23

<210> SEQ ID NO 21
<211> LENGTH: 23
<212> TYPE: DNA
<213> ORGANISM: Mus musculus

<400> SEQUENCE: 21
gtttcagcta aaaatgacg cgg                                               23

<210> SEQ ID NO 22
<211> LENGTH: 23
<212> TYPE: DNA
<213> ORGANISM: Mus musculus

<400> SEQUENCE: 22
gtctctgtgc actggttcca ggg                                              23

<210> SEQ ID NO 23
<211> LENGTH: 23
<212> TYPE: DNA
<213> ORGANISM: Mus musculus

<400> SEQUENCE: 23
caggcactcg gttctggccc tgg                                              23

<210> SEQ ID NO 24
<211> LENGTH: 20
<212> TYPE: DNA
<213> ORGANISM: Artificial Sequence
<220> FEATURE:
```

<223> OTHER INFORMATION: Synthetic primer

<400> SEQUENCE: 24
gcctgggaaa gagctccccg                                                    20

<210> SEQ ID NO 25
<211> LENGTH: 23
<212> TYPE: DNA
<213> ORGANISM: Artificial Sequence
<220> FEATURE:
<223> OTHER INFORMATION: Synthetic primer

<400> SEQUENCE: 25
taggcctggg aaagagctcc ccg                                                23

<210> SEQ ID NO 26
<211> LENGTH: 19
<212> TYPE: DNA
<213> ORGANISM: Artificial Sequence
<220> FEATURE:
<223> OTHER INFORMATION: Synthetic primer

<400> SEQUENCE: 26
cggggagctc tttcccagg                                                     19

<210> SEQ ID NO 27
<211> LENGTH: 23
<212> TYPE: DNA
<213> ORGANISM: Artificial Sequence
<220> FEATURE:
<223> OTHER INFORMATION: Synthetic primer

<400> SEQUENCE: 27
aaaccgggga gctctttccc agg                                                23

<210> SEQ ID NO 28
<211> LENGTH: 18
<212> TYPE: DNA
<213> ORGANISM: Artificial Sequence
<220> FEATURE:
<223> OTHER INFORMATION: Synthetic primer

<400> SEQUENCE: 28
acgcggtgag ttgtagac                                                      18

<210> SEQ ID NO 29
<211> LENGTH: 22
<212> TYPE: DNA
<213> ORGANISM: Artificial Sequence
<220> FEATURE:
<223> OTHER INFORMATION: Synthetic primer

<400> SEQUENCE: 29
taggacgcgg tgagttgtag ac                                                 22

<210> SEQ ID NO 30
<211> LENGTH: 18
<212> TYPE: DNA
<213> ORGANISM: Artificial Sequence
<220> FEATURE:
<223> OTHER INFORMATION: Synthetic primer

<400> SEQUENCE: 30
gtctacaact caccgcgt                                                      18

```
<210> SEQ ID NO 31
<211> LENGTH: 22
<212> TYPE: DNA
<213> ORGANISM: Artificial Sequence
<220> FEATURE:
<223> OTHER INFORMATION: Synthetic primer

<400> SEQUENCE: 31
aaacgtctac aactcaccgc gt                                              22

<210> SEQ ID NO 32
<211> LENGTH: 25
<212> TYPE: DNA
<213> ORGANISM: Artificial Sequence
<220> FEATURE:
<223> OTHER INFORMATION: Synthetic primer

<400> SEQUENCE: 32
agcattcaca cagggtgggg aattt                                           25

<210> SEQ ID NO 33
<211> LENGTH: 26
<212> TYPE: DNA
<213> ORGANISM: Artificial Sequence
<220> FEATURE:
<223> OTHER INFORMATION: Synthetic primer

<400> SEQUENCE: 33
ctggcctgga gtttacttgg catcag                                          26

<210> SEQ ID NO 34
<211> LENGTH: 25
<212> TYPE: DNA
<213> ORGANISM: Artificial Sequence
<220> FEATURE:
<223> OTHER INFORMATION: Synthetic primer

<400> SEQUENCE: 34
cccctggagc ttctcaactc cattc                                           25

<210> SEQ ID NO 35
<211> LENGTH: 30
<212> TYPE: DNA
<213> ORGANISM: Artificial Sequence
<220> FEATURE:
<223> OTHER INFORMATION: Synthetic primer

<400> SEQUENCE: 35
ctctgtttct accttcttgg acatcctggc                                      30

<210> SEQ ID NO 36
<211> LENGTH: 22
<212> TYPE: DNA
<213> ORGANISM: Artificial Sequence
<220> FEATURE:
<223> OTHER INFORMATION: Synthetic primer

<400> SEQUENCE: 36
ggccacttat catcacttgc cc                                              22

<210> SEQ ID NO 37
<211> LENGTH: 21
<212> TYPE: DNA
<213> ORGANISM: Artificial Sequence
<220> FEATURE:
<223> OTHER INFORMATION: Synthetic primer
```

```
<400> SEQUENCE: 37
ggtggtaaag gggcctagga g                                              21

<210> SEQ ID NO 38
<211> LENGTH: 25
<212> TYPE: DNA
<213> ORGANISM: Artificial Sequence
<220> FEATURE:
<223> OTHER INFORMATION: Synthetic primer

<400> SEQUENCE: 38
ctccagaagt ggatgcggcc agtcc                                          25

<210> SEQ ID NO 39
<211> LENGTH: 25
<212> TYPE: DNA
<213> ORGANISM: Artificial Sequence
<220> FEATURE:
<223> OTHER INFORMATION: Synthetic primer

<400> SEQUENCE: 39
gcggcaggag agggcgcggt ccctg                                          25

<210> SEQ ID NO 40
<211> LENGTH: 4993
<212> TYPE: DNA
<213> ORGANISM: Mus musculus

<400> SEQUENCE: 40
ggacacgtac ctctggggtg atctacttag gagaactccg gcccacttgg gatcgtgtac      60
acagagttgc atactaacgt tagataagag cggaggagaa ggtggcccct gccaaggaga     120
catgggatct gtatggggtt ggaaggctgg tgtgtccaga ggggcttacc cactgtcaga     180
atagaatagg acctgctggg cttttggagt gaaggcagac agcctggtgg gagggactct     240
gggcaggtaa ctcccacctg cccgcccgcc cggcgcaca cttgtttgtt gtgcttcctc      300
cttccttggc ggcaggaagg tggagcgcgc agggaacgcc gagactggtt agattgggga     360
tagaaaccga tgtgggaaca cgttagggtg atcgccacat ccctgtgccg ttaggccagg     420
taggaacagg aggattaggg agacacagca gggaaacaaa gaccccagaa gctgacggag     480
aagctgggag tgatgcccag gagagagagt acttaggcaa aggcccctga ggtagacaaa     540
aggcagagcg ggggcaagca gagagggtga gggggtgggg cagccaggct gccagcagat     600
gggggatttg ctttgtggag ctcaactctt aagccagggg aggttcggaa gaacttgatg     660
gggtgggagc tcagcgact  ctggccactt atcatcactt gcccacatcc ctggggccc       720 tagggggacag aagtctctag tatcagccaa ttatggccca tatctaagga ccggaggact     780
ccagttgtgt ctcaaactat ggccaccttc acttactacc tttgacctag ctgcagagtt     840
ggaagcactc gagggctgtc tgtcatcctt gctgagagaa aggtgacctt ctgtcttgca     900
ggacctgaaa gaaaagaagg acaaggtgga ggagaaggcc ggccggaaag aacggaagaa     960
agaagtagtg gaggtgtgaa ggcagcaggg ggaagatgac tgcgcttgcc caaacatcct    1020
tcctgccccc ctaccttctg ggggtgctgg ggtcctgcca ttctctcgac ctcttctcat    1080
tccttcccta ccctgagact cctaggcccc tttaccaccc agtgagtggc agcacagctg    1140
gcttgacatc catcaccct  tgtcttggtc cccataggag gaggaatg  gagctgagga     1200 agaggaagaa gaaactgcag aggatggaga ggatgatgat gaaggggatg aagaaggtag    1260
ggatgggtag ggaaggctgg gctgcaaagt tgagacacaa aagagcagag ccagggagca    1320
```

```
gttgaagact ggacactggg atagaaaggg gtgggtgtgg ggtacgcgc gcgcgtgccc    1380 agagcctccc aaccttcccc agtgacttgt ttctggctcc tcagatgagg aagaagagga    1440
ggaggatgaa ggccccgtgc ggaagagaac tgctgaagag gaggtttgag ctgggttgga    1500
gcctgagggg ctgtcaggaa tatatcaagg gctgggtggc ctttggatt ggacccaggt    1560 ccttgtgggt agcatggata ggcagggcc agagcagggc cagcaggaac ggggaagtct    1620
cctttgtaca gctacttcaa ctcttatcct ctccacagga tgaagcagac cccaagaggc    1680
agaagacaga aaacggggcg tcggcatgaa ccctgcccg tgggcttggg gatgggaggc    1740
ccctcaggtc ctggaggtgg ggcgggaaca cacaaatcca gccccttc tcctggctcc    1800 ctgctctggc cctgcccag agctgtgacc cttgtccttt gacccagcct ctcatttcca    1860
tctctccaga cactgctcct tcaccctcac tgccaccggt ccagctcctg acccgcctca    1920
tctgagctcc ccagccagcc ctcacttgcc ctagcattct tgttcttctt tcctgccttc    1980
cctcaccatc ccatatgttc cggtccctgc gaagcctctc cttgccctct acccccgag    2040 cctctcagcc tgcccttctt tctcctgcct gaccctggg tctccctcag attccctcct    2100
ctcagacagc gccaggccgg ggtggggctg gggttgggc caagcccga agctgccccc    2160 tccccttttt gtataattta ataaagaaac ggtcgcgctt ctgttttaa cccgtctcct    2220 gctttcccgc agtccggtca gtgcatgaaa gggtgtagag ggcgtggctg acctcatacc    2280
cagattataa gagacatggc cagtcctcgg agtgggagct caaggtcttc ctctggggc    2340 tgacatacgt cctgttttg ggctcctggg gaggtttctc ctcagcagtg cacactatat    2400
catgttaact cacgtaagat ctagactctg ctgagcccag tggaaagctt ccagctccat    2460
tgtgctgaac caggcagata gaaacaggaa gtcctgcccc caaggtggaa gaggctgtta    2520
ggcccatgtc tcaacctaga gtttggaaag agaactccca agcatggaca cattttgac    2580 tcgtgggaag cagagttctc atacatgggc ggcaaaagac tccagagtta gttatcaggc    2640
ctgtctcctt gtcatcgtct tcattttctc agctcagctg agctggggag caaaggttgt    2700
tgggttcctc tagcctgcct cagttcctct tgttttatag tcttactacg cagccctggc    2760
tggtctgaaa ttcacataaa gccacctgcc tctgcctagt aagtactggg attaaaggtc    2820
tttttccctt tttattttaa gttcatttt gttggcatag catctacttt gtagccaggg    2880
atgaccctga actcatgggc ccaagcaagc cagcttcaat tcaccccacc ttccaaaatc    2940
ttgacttaca catgccactg ttgctgacac cttggtctct cttgagtttt ccttgctata    3000
agattcctgc attattccat ctccatagac ccttgccttc atttttttct taaagtacag    3060
aatcttgggg aggagggagg ttttgaagac aggaaaacat cctattgtca gggctggaaa    3120
ggccgttctg cagttatgag tgcttgttgc ctttcaagaa gacctaggtt tgatgtcgag    3180
catccagatg gggcggctcc caaaacacct gtaactccag ttccaaggaa tctgacaccc    3240
tcttcaggcc tctgagcatt cacacagggt ggggaattta tgtatacaga cacataaata    3300
aaagtagaca tctaaaacaa gtttcccagc cgaatgtggt aggtggtgca tgcctttaat    3360
cccagcactc aggaggcaga ggcaggcgca tttctgagtt caaggccagc ctggtctaca    3420
aagtgagttt caagacagcc ggaatacaca gagaaaccct gtctcgaact cccccccccc    3480
cccacacaca cacataaaac caagtttctc agtgtcatct tcctagaaga tgaaaggcca    3540
tcccataatg caagtagggt taaggactag acagcttttg ccttcatgct tcctaatgtt    3600
ggcaagttat ttaatgcctg tgagcctcaa gtcccgaaat ctgtacaaaa aggggcgcgc    3660
```

| | |
|---|---|
| atcaagtttc acaagttgct ttacggaaaa tgtataatac agttatatgt agcatagaat | 3720 |
| gaaggttaac accgtgtggc tactatactt ttccactgag cccttaccca gatctggtaa | 3780 |
| cttgtggtat ggtgacactt cttgagtacc tgtccaagag atgctgaaag gctaggcagg | 3840 |
| cagactgtag gacagtggct ttttttttt ttttttcag tgttaatggg aaagagcaag | 3900 |
| tcaagaagaa actgtgggga cagtagagga agcttaaaga tacagctgta gttctaggca | 3960 |
| gaaatgcttg gcagagagag agagagagag agagagagag agagagagag agagagagag | 4020 |
| aggagacaga gggggaagag gtgaagaggg ggcggtaggg agacccgagt ctgaggaagt | 4080 |
| aaacaagggg agtgccacca ccgagaggag ggctcggctg ctgggaatca gcccctcac | 4140 |
| actttccact gcgaagcgaa accccgcgcc ttggtctggg gggcgggca gtggggagga | 4200 |
| gaagcagaag gactgggtct ggaggagcag ctcaagttct agctagctgc agtgggtttg | 4260 |
| cctgcactct gctctgggtc ccagcccggg cctctgatca ttatccatcc tgctgtctcc | 4320 |
| agtccccact cctggggcgt cctcttcacc ctacattctt tccctccgcc tcacctcctc | 4380 |
| cttgtagaac ttctctctct ctctctctct ctctctctct ctctctctct ctctctctgt | 4440 |
| gtgtgtgtgt gtgtctgtct gtctgtctgt ctctctctcc tcccaggacc ttttttctaac | 4500 |
| ctcccttgga gggctgggga ggcccggcc atagaggaga tgaggagga cctgctcctt | 4560 |
| ggcttttttgc ttctgggact gctttgggaa gctccaggta aggtggagag tccagcaggg | 4620 |
| acctctatgg ctgtctcttt agctgtgtgtg atattccaat gcttttgttg agggagggg | 4680 |
| tgtgtgtgtg tgtgtgtgtg tgtgttttga cacagggttt cttttgtgttg ccctggctgt | 4740 |
| cctgggactg gctctgatga ccaggctggc cttgaattta tagtgatcca cttgcctctg | 4800 |
| cctccccagt gctgggatta gaggcgtgca ccatcacttt gtataagggc agatcccaaa | 4860 |
| gctgcctcag cctcccttca acagggaggc atgatgtttc tttcttagga aagccagggc | 4920 |
| atttctctat tctccaatct cttggctcaa tgcccttggc ctctcttttg ttccactagt | 4980 |
| tgtgtcttca ggg | 4993 |

<210> SEQ ID NO 41
<211> LENGTH: 3933
<212> TYPE: DNA
<213> ORGANISM: Mus musculus

<400> SEQUENCE: 41

| | |
|---|---|
| acttgtgctc agacccctgg ctacagagaa ggaaagcact ggcaggcgat cgcgcgcgtg | 60 |
| cacgcgcgcg cgcacacaca cacacacaca caccacacgc tcgcgggctc acaccaccca | 120 |
| tgtgaaatcc agaagatggg agcctcctaa tctttctgga taaccagctg acgttgttac | 180 |
| ctctgcccca tccccatgt ttgtcatccg tgggtgactt ttctggcccc aggcatgaca | 240 |
| acacactgcc acctagtggt caccgctcgc cacgccccca gaggaggtca ctggaccaac | 300 |
| tgccacagcc aggatgccta acactgcagt aggctaggtg gagcaaggat gcaggtgctt | 360 |
| catttacata tgcattctgg gtgtgcagcc tcgaatgtgc tcccagcatc tgtcacgtgt | 420 |
| ctgatgtacc ccgcaggaga gggactaaat aatacaagct tcaggaaata cagccctggt | 480 |
| actggcaagg ttataatccc agtaagacaa aggagagggc tgtaaacaaa gaccataggc | 540 |
| agggaggaaa acaagccacc aggacttctg tgtattgcct gtgagagtcc taagtcctgg | 600 |
| attctctttc tattaccgtt gatgaggatg ttacaaatct cttttaaacat ttgttttcta | 660 |
| atctattaag tgggacaatg gccaggagcg ggaggcagga ggatgcccct gggtccagga | 720 |
| gtactggaca aacatgggta acatagtgag acccccatct tttaaaagta aaaactgaat | 780 |

```
atggaggtgc ctgcttgtaa ttccagcaca tggaaaagtc accaacttag taagtttgag      840
gccagcttag gcgacatcag atcctgactt ggaaataaat tatacggtgg ggcatgccat      900
aggggctccc aacactcggg aggtagaggc aggaagatct ctgtgagttt gaggccagcc      960
tgatcaacct agtgagttct acgacagcca aggctacaca gagagaccct atctcaaaaa     1020
caaacattat tttaattact aggccagtgg gatggagcag agggtaaaga ggcatgccac     1080
gtaagcttgg tgacctgatt caccgacacc tgggatacag gtaaaggcga aagaaagcaa     1140
ccaccagttc aacaacgttg ttctctgaac atgcatgcca tgggacccac tcacatataa     1200
caccatgcac acacaccatc atcaccatca ccatcaccat catcaccatc accatcacca     1260
tcatcaccat caccatcatc ataatgatga ggagatggct cagcacatgc ttcgcaagcc     1320
ggaggacctg agttcagctc cccggcaccc gtataaaagt taggtgactt ccaaagaccc     1380
tttaggatat tgctttacag tgcgcctgtc tctgatccct cttccagggc cactgggttt     1440
ccacctgtga aacccaaga gtcccagccc tgaaccccaa acctcagaac atcagattgc     1500
cttaaatggc tgggtattca ggctttgggg actcccagca caaaataatg gtgtcacttt     1560
tcattctctg tccccaagtc tctgtcccct ctgtctccat agagatggag atcttcaacc     1620
tcctgtttat gctcaggtac cagtgtaggg tgtttgtcac agctgtgtgt atgccaccgt     1680
gagactcctt caggctccct tcctcttggg gtcactaatt tgctcccctg tgcagagcta     1740
cagctccctg acaaacagca agggtccagg ctccaccttc atcacagtgc aaggtctcag     1800
gtcctacccc tttgactgag gcacagtgtg ttctgcagag acctctgctg aggccctgcc     1860
tcaggccttc tttccatggc ctcaggggag gccaccatgt tttcacaagg caaggatttc     1920
ctggaaagtt ttgtgggtgg catttttttcc tttgcactag ataataaccc atgccctttg     1980
ggtttgtgag agaagtcaca ggctcaccaa ggctcctgca gggacttccc cacactcttt     2040
catgaaggga acagaggcag agtagaagac caccttggtc ttctgtctct catagaagat     2100
gtgtgaggcc agtggcacag aacacaagac agaggggttg gcagcttgtg ttgaacagtg     2160
catagttcat acagagcccc accctcttgc cagcaggata acttctagcc cttccttgca     2220
gtgtgtgtcc ttgttagatc tctgcgagtt gggttaattc gctagttgtg ttcccaagtg     2280
gctgtttgtt tgggtgtttt gttttttgtt tttgtttttg tttttttgtt tttttaatg     2340 gctttggagt ttgaacctag gatctcgggt ttgtagcaaa tgttctacca atgggctcct     2400
cagcctgttg accagttagt ttatctgtaa accagtgctc tggactggga gcctgaaggt     2460
gaagggagcc tgagaggagg caagttgatc ggggagcttt aggggttggg caggggagt     2520 catcccagaa gcaaagaatg tatattatag ctatctatca ctgcacttaa aaaaaaaaa     2580 atcaccccag aactgggtaa tcccctccca ggcagaaatc aggctagcag atcatgctgg     2640
tacagggttt gtcacgaggc tgctctaatg tgtggccaaa gctgtggtca aggggaagcg     2700
aggcccgggt tgaggaatct gtctctgaac aggctcgctc acttggtcga gggccagagg     2760
cctcagttct tcctctttag tgccatggca actggcctct ctgtggacag gatggatgag     2820
acaaaagcac tcaggcgtca tcacctgatc ttgaaagtga taggtcatca tttctgcccc     2880
tgtctgtaga tcacacaggc cacttgtgac acggtatagg aaatgcaaga taaggatgtc     2940
aaccaaggaa ggggattgct gggacctctt agagcctggc tgtcacaagc tagcagtact     3000
tgaatgacag acagcccaag aaagaggagg gggcatctct gattatccga catctgtgcc     3060
cttctcacgg aattggcagg ctcctccact gtcaactttg cagaagttct ggaggctaat     3120
```

| | |
|---|---|
| caaggccaat cctgcaggta gaaggctacc cggtggacct ccagacccett ggctactgct | 3180 |
| ccttccacat atgaacttgt ttacagggct tcatggctca gaacctaccc agagaattt | 3240 |
| ctgttctaca tccccaacca agccaaggtg ttggggttca aatttgagcc ccagctgtta | 3300 |
| gccctctgca agaaaaaaa aaaaaaaaaa agaacaaagg gcctagattt cccttctgag | 3360 |
| ccccacccta agatgaagcc tcttcttca agggagtggg gttggggtgg aggcggatcc | 3420 |
| tgtcagcttt gctctctctg tggctggcag tttctccaaa gggtaacagg tgtcagctgg | 3480 |
| ctgagcctag gctgaaccct gagacatgct acctctgtct tctcatggct ggaggcagcc | 3540 |
| tttgtaagtc acagaaagta gctgaggggc tctggaaaaa agacagccag ggtgaggta | 3600 |
| gattggtcct tctagttgca gcttccaagg tgccgccagg gtctgggcgt ttcaccccac | 3660 |
| accaaggaga agcctttgta acccagccca gctaccgacc caagcccacc ccacagctat | 3720 |
| tttgcgggag tttcagtgct atagcagatg gtttctgtaa cgaggtcacc acagggctgc | 3780 |
| acctggtgct ccacttccat cgtcctcatc tctaatacac tggcctcctc tagtgctctt | 3840 |
| ttggcagcct ctcacagtgt ccgggcccct gcttccttc tcccatttgg tcaccttccc | 3900 |
| ctcttctagc tagaagcaca gaatatggac agc | 3933 |

<210> SEQ ID NO 42
<211> LENGTH: 4683
<212> TYPE: DNA
<213> ORGANISM: Homo sapiens

<400> SEQUENCE: 42

| | |
|---|---|
| ccaggggctg aggtcccggt ggtgtgggcc caggagggggg ctcctgccca gctccctgc | 60 |
| agccccacaa tcccctcca ggatctcagc cttctgcgaa gagcaggggt cacttggcag | 120 |
| catcagccag acaggtatgc accccaaact tgggcaacag gacctccgaa tccagcactc | 180 |
| aaccccacac ccgtgccggt cctctgtccc ctgccctgag gtgtcactcc ctctgaagcc | 240 |
| agtgacccag tctccctgcc ctcgcttgca ccgttcctgc ccttgctctg caatcagcga | 300 |
| ccctcacgcc agcatcccett ctctccagaa gtggatgcgg ccagtccaac agaggggtcg | 360 |
| ggcgtgaggg gacggttggt ggtcaagaga actcttgggg cgggcttct catcctcaac | 420 |
| gggtggctgc ctgcatcctc ccgggcttcc tacccctgga gcttctcaac tccattctct | 480 |
| ttcccgccca gtggcccgcc cgctgccgcc ccggccatc ccctggcccc cggccctcac | 540 |
| ccggcggcgc cctcctcctg ggggcccagg ccccgccgct acacggtgct gagcgtgggt | 600 |
| cccgaggcc tgcgcagcgg gaggctgccc ctgcagcccc gcgtccagct ggatgagcgc | 660 |
| ggccggcagc gcggggactt ctcgctatgg ctgcgcccag cccggcgcgc ggacgccggc | 720 |
| gagtaccgcg ccgcggtgca cctcaggac gcgcccctct cctgccgcct ccgtctgcgc | 780 |
| ctgggccagg cctcgagtat gtgggcgggg acgatgggag aagggctggg aggtgggtcc | 840 |
| ccatcccctg cctcccggga cgcaggaagg gctggggcag aggctgcgcc ctaggccctg | 900 |
| tcggagagct cccagaagag tagaggaagg gggtgggcgg cctgctggag tggaaggtgc | 960 |
| ccccgaagca cgtgtatggg gggccctgtg gagagattgt gtcaccccg agctcccctt | 1020 |
| ctcccacccca cgcggagtg cccagaggga ggggagggg gggagagcat ggggctaaag | 1080 |
| tgattcattt cagatatctg tagctcaggg ggtgggcttc gcggggttcc aggccaggaa | 1140 |
| aacggcaagg gtggctgatg ccaagtaaac tccaggccag ggacggggaa agtggtcctg | 1200 |
| gggagtcttg gggatccact ttatgcacct ccaggtgctg gaagctgaga tggggagagg | 1260 |
| gtgatgtggg agaggagaag acaagtctaa agccaggtgc ctgtttccag gagcttccgg | 1320 |

```
cttggcagcc ctgctgtgtt gggaaattgt ttccagtggg ctgatgaagt cttctttatc   1380
cttgcacagt gactgccagc cccccaggat ctctcagagc ctccgactgg gtcattttga   1440
actgctcctt cagccgccct gaccgcccag cctctgtgca ttggttccgg aaccggggcc   1500
agggccgagt ccctgtccgg gagtcccccc atcaccactt agcggaaagc ttcctcttcc   1560
tgccccaagt cagccccatg gactctgggc cctggggctg catcctcacc tacagagatg   1620
gcttcaacgt ctccatcatg tataacctca ctgttctggg taactccccc actctgcttc   1680
acatttgacc acaactcctt cctgccccca ttgtcacctc ccctaactat gggtccccaa   1740
accaggttct cggcagcgag tggcctacgt cattgctgtg ggtctcactg ttcgacccct   1800
ttatattgct ggcagcctca cagctgccat cacccttct tgcttctccc gtggccttcc    1860
agcgtcattg ccggccttcc ctctccttcc ggctaagccc acttgctggg tttctgagcc   1920
tcctcagctc atcaccttat tctgctcctt agcactctta tgagccagac catctcctga   1980
attcttctgc ctcccttcct tgcagcccca gcactccctc cccactgcag cacccagctt   2040
taactttggg ttttctttc tcttcaggtc tggagcccccc aactcccttg acagtgtacg    2100
ctggagcagg ttccagggtg gggctgccct gccgcctgcc tgctggtgtg gggacccggt   2160 cttcctcac tgccaagtgg actcctcctg ggggaggccc tgacctcctg gtgactggag    2220
acaatggcga ctttacccctt cgactagagg atgtgagcca ggcccaggct gggacctaca   2280
cctgccatat ccatctgcag gaacagcagc tcaatgccac tgtcacattg gcaatcatca   2340
caggtcagcc tcaggtggga aaggagtagc tgccctccca gggtagaaag acagggagg    2400 aagggctggc agggcaaaga ctaggcaaac ccaccctgtg atgccaggcc actgggcaca   2460
agttccagag cctgcccatc tcggccccca ctttctcac cccataata aagaaacgaa     2520 actgaaaatc tcctcttgag tcacaagata aagttccac cgttctctat gggactcccc    2580
tgctctcaat tggcgggagg gtctgggaag ttagaaggaa aggtgacaaa aattctgaat   2640
ggttcgaaag aggtagaata tatttctaga atccttgtct actttgcagc cagggcttgg   2700
gttagagttg caggaagtgg cctggatttg ggaggagtga ataaatccgt cccttggtca   2760
gcaaatattt actgagcaag ggttttccaa gacagtataa aacaaacaca gaaaaaagaa   2820
tactcagaga gtatgtgttg actggttgat aactatcggc catgacagat tagccatgtc   2880
tgcagcacgc acctgcggcc actcagtagt agcaccccac ggcaggtgct taataatgta   2940
tagagattga atgaatacgt gaacatgcta atggataata catctcctga aggccaatcc   3000
tgagttttca cttgctttct ggatacctct aactagatgt tataccacct ctcagccgcc   3060
ttaccctgaa ccccagcttt ttctcccacc aatcccttg ctgactcagc ctgtcagtaa    3120
tccactggta tccatccacc tcgaaacctg gcctcctcct ctctacatcc catcagtcat   3180
caaagtccac cagttctttc tgtccaatgc cctcttgaag gtcaactgtt ttatgtagac   3240
ggctcaatga gagagatact gttacccccga agactttctc aaaacagctg ggaagtgcca   3300
gactctgggt ctaaactcag gtgtctgcat caccaaatca ctctccagga cactactcag   3360
atgcccttca ccctttgtct cctcccaccc acccatctct cactttacaa cttggagaat   3420
gctctgtctc tagatgaatg ggtcagttcc ctgttctcta taccttcaga aaggggggatg   3480 atgttcattc aggggggcacc acaaggcagg ggacactgat gtgagccgca tcatggaagt   3540
tccaaaattg tgaagtagat gggggtcagc tcatctgact gatttgagg gttctgagca    3600 tttgagtaga aagtaatgta aaagaatctg taatagtatt tattctgtgg tctgccaggg   3660
```

| | |
|---|---|
| ccagtttgag tgtgaaggca gtagggagcc tggaaatgtt tgagcaggg gagggagctg | 3720 |
| actagagcat tgtctgaata agataaatgt ggccggcagg gcatgatggc tcacacctgt | 3780 |
| aatcccagca ctttgaaagg ctgagacgag aggagcactt gagtccagga attccagact | 3840 |
| agcctgggca acatggtgaa aacgcatctg tatacaattt aataaaaaaa taaatagaaa | 3900 |
| gaaaaagatg aacgtggcca tgacccatga tgtccttccc caacctcccc tggccagaac | 3960 |
| ccaagtgagt gcagggtgat tgagacttgg ggttcaacct gtgatatcac gtaaggggg | 4020 |
| cagaatccca aaagatctct tccttctact cttttcagtg actcccaaat cctttgggtc | 4080 |
| acctggatcc ctggggaagc tgctttgtga ggtgactcca gtatctggac aagaacgctt | 4140 |
| tgtgtggagc tctctggaca ccccatccca gaggagtttc tcaggacctt ggctggaggc | 4200 |
| acaggaggcc cagctccttt cccagccttg gcaatgccag ctgtaccagg ggagaggct | 4260 |
| tcttggagca gcagtgtact tcacagagct gtctagccca ggtccgaggc cccagaatgc | 4320 |
| caggacccaa acgccacagc aataatcttt atcctccttc cagaacagcc cctgccaccc | 4380 |
| ccatcccagc gcttttcttt ccagtcaggg acctgatctc tggcttttgc ctagggttga | 4440 |
| cccgtttccg ccactgatca gctgaatgac cctgggacaa gtcccttaaa ctctctggat | 4500 |
| ctcattgcat ctgtaaagtc tgagagaatg acaaagtgtc ctttctagtc ctgaccctat | 4560 |
| gcctcatcct gtactttctc cataggtgcc caacgctctg ggagagcccc aggtgccctc | 4620 |
| ccagcaggcc acctcctgct gtttctcatc cttggtgtcc tttctctgct ccttttggtg | 4680 |
| act | 4683 |

<210> SEQ ID NO 43
<211> LENGTH: 2044
<212> TYPE: DNA
<213> ORGANISM: Artificial Sequence
<220> FEATURE:
<223> OTHER INFORMATION: Humanized LAG-3 (long)

<400> SEQUENCE: 43

| | |
|---|---|
| gggcagtggg gaggagaagc agaaggactg ggtctggagg agcagctcaa gttctagcta | 60 |
| gctgcagtgg gtttgcctgc actctgctct gggtcccagc ccgggcctct gatcattatc | 120 |
| catcctgctg tctccagtcc ccactcctgg ggcgtcctct tcaccctaca ttctttccct | 180 |
| ccgcctcacc tcctccttgt agaacttctc tctctctctc tctctctctc tctctctctc | 240 |
| tctctctctc tctgtgtgtg tgtgtgtgtc tgtctgtctg tctgtctctc tctcctccca | 300 |
| ggaccttttt ctaacctccc ttggagggct ggggaggccc gggccataga ggagatgagg | 360 |
| gaggacctgc tccttggctt tttgcttctg ggactgcttt gggaagctcc agttgtgtct | 420 |
| tcagggccag gggctgaggt cccggtggtg tgggcccagg aggggctcc tgcccagctc | 480 |
| ccctgcagcc ccacaatccc cctccaggat ctcagccttc tgcgaagagc aggggtcact | 540 |
| tggcagcatc agccagacag tggccgcc gctgccgccc ccggccatcc cctggccccc | 600 |
| ggccctcacc cggcggcgcc ctcctcctgg gggcccaggc ccgccgcta cacgtgctg | 660 |
| agcgtgggtc ccggaggcct gcgcagcggg aggctgcccc tgcagccccg cgtccagctg | 720 |
| gatgagcgcg gccggcagcg cggggacttc tcgctatggc tgcgcccagc ccggcgcgcg | 780 |
| gacgccggcg agtaccgcgc gcggtgcac ctcagggacc gcgccctctc ctgccgcctc | 840 |
| cgtctgcgc tgggccaggc ctcgatgact gccagccccc caggatctct cagagcctcc | 900 |
| gactgggtca ttttgaactg ctccttcagc cgccctgacc gccagcctc tgtgcattgg | 960 |
| ttccggaacc ggggccaggg ccgagtccct gtccgggagt ccccccatca ccacttagcg | 1020 |

-continued

```
gaaagcttcc tcttcctgcc ccaagtcagc cccatggact ctgggccctg gggctgcatc      1080
ctcacctaca gagatggctt caacgtctcc atcatgtata acctcactgt tctgggtctg      1140
gagcccccaa ctcccttgac agtgtacgct ggagcaggtt ccagggtggg gctgccctgc      1200
cgcctgcctg ctggtgtggg gacccggtct ttcctcactg ccaagtggac tcctcctggg      1260
ggaggccctg acctcctggt gactggagac aatggcgact ttacccttcg actagaggat      1320
gtgagccagg cccaggctgg gacctacacc tgccatatcc atctgcagga acagcagctc      1380
aatgccactg tcacattggc aatcatcaca gtgactccca aatcctttgg gtcacctgga      1440
tccctgggga agctgctttg tgaggtgact ccagtatctg acaagaacg ctttgtgtgg      1500 agctctctgg acaccccatc ccagaggagt ttctcaggac cttggctgga ggcacaggag      1560
gcccagctcc tttcccagcc ttggcaatgc agctgtacc aggggagag gcttcttgga      1620 gcagcagtgt acttcacaga gctgtctagc ccaggtgccc aacgctctgg gagagcccca      1680
ggtgccctcc cagcaggcca cctcctgctg tttctcatcc ttggtgtcct ttctctgctc      1740
cttttggtga ctggggcctt tggctttcac tggtggagaa acagttgct actgagaaga      1800 ttttctgcct tagaacatgg gattcagcca tttccggctc agaggaagat agaggagctg      1860
gagcgagaac tggagacgga gatgggacag gagccggagc ccgagccgga ccacagctg      1920 gagccagagc ccaggcagct ctgacctgga gccgaggcag ccagcaggtc tcagcagctc      1980
cgccccgccg cccgcccgcc cgaataaact ccctgtcagc agcatcaaaa aaaaaaaaaa      2040
aaaa                                                                   2044
```

<210> SEQ ID NO 44
<211> LENGTH: 529
<212> TYPE: PRT
<213> ORGANISM: Artificial Sequence
<220> FEATURE:
<223> OTHER INFORMATION: Humanized LAG-3 (long)

<400> SEQUENCE: 44

```
Met Arg Glu Asp Leu Leu Leu Gly Phe Leu Leu Leu Gly Leu Leu Trp
1               5                   10                  15

Glu Ala Pro Val Val Ser Ser Gly Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175
```

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Leu Leu Phe Leu Ile Leu Gly Val Leu Ser Leu Leu Leu Leu
    450                 455                 460

Val Thr Gly Ala Phe Gly Phe His Trp Trp Arg Lys Gln Leu Leu Leu
465                 470                 475                 480

Arg Arg Phe Ser Ala Leu Glu His Gly Ile Gln Pro Phe Pro Ala Gln
                485                 490                 495

Arg Lys Ile Glu Glu Leu Glu Arg Glu Leu Glu Thr Glu Met Gly Gln
            500                 505                 510

Glu Pro Glu Pro Glu Pro Glu Pro Gln Leu Glu Pro Glu Pro Arg Gln
        515                 520                 525

Leu

<210> SEQ ID NO 45
<211> LENGTH: 104
<212> TYPE: DNA
<213> ORGANISM: Artificial Sequence
<220> FEATURE:
<223> OTHER INFORMATION: Junction sequence

<400> SEQUENCE: 45

```
ggcccacacc tagctcagct gcacttcagt ctcgaggtcg acggtatcga taagcttgat      60
atcgaattcc gaagttccta ttctctagaa agtataggaa cttc                     104
```

<210> SEQ ID NO 46
<211> LENGTH: 102
<212> TYPE: DNA
<213> ORGANISM: Artificial Sequence
<220> FEATURE:
<223> OTHER INFORMATION: Junction sequence

<400> SEQUENCE: 46

```
gttcctattc tctagaaagt ataggaactt catcagtcag gtacataatg gtggatccac      60
tagtcacttg tgctcagacc cctggctaca gagaaggaaa gc                       102
```

<210> SEQ ID NO 47
<211> LENGTH: 25
<212> TYPE: DNA
<213> ORGANISM: Artificial Sequence
<220> FEATURE:
<223> OTHER INFORMATION: Synthetic primer

<400> SEQUENCE: 47

```
gtaatacaag tgcccaaacc cacca                                           25
```

<210> SEQ ID NO 48
<211> LENGTH: 20
<212> TYPE: DNA
<213> ORGANISM: Artificial Sequence
<220> FEATURE:
<223> OTHER INFORMATION: Synthetic primer

<400> SEQUENCE: 48

```
cgggtgtggg gttgagtgct                                                 20
```

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49

```
atgtgtgagt tggtgttagc ctggg                                           25
```

<210> SEQ ID NO 50
<211> LENGTH: 25
<212> TYPE: DNA
<213> ORGANISM: Artificial Sequence
<220> FEATURE:
<223> OTHER INFORMATION: Synthetic primer

<400> SEQUENCE: 50

```
gacactccac tcccttctcc cttca                                           25
```

<210> SEQ ID NO 51
<211> LENGTH: 25
<212> TYPE: DNA
<213> ORGANISM: Artificial Sequence
<220> FEATURE:
<223> OTHER INFORMATION: Synthetic primer

<400> SEQUENCE: 51

```
actcctataa tgaggtgaga ggcag                                           25
```

```
<210> SEQ ID NO 52
<211> LENGTH: 26
<212> TYPE: DNA
<213> ORGANISM: Artificial Sequence
<220> FEATURE:
<223> OTHER INFORMATION: Synthetic primer

<400> SEQUENCE: 52
gccccgctgg gatttaggac agcaac                                          26

<210> SEQ ID NO 53
<211> LENGTH: 23
<212> TYPE: DNA
<213> ORGANISM: Artificial Sequence
<220> FEATURE:
<223> OTHER INFORMATION: Synthetic primer

<400> SEQUENCE: 53
ggatcggcca ttgaacaaga tgg                                             23

<210> SEQ ID NO 54
<211> LENGTH: 23
<212> TYPE: DNA
<213> ORGANISM: Artificial Sequence
<220> FEATURE:
<223> OTHER INFORMATION: Synthetic primer

<400> SEQUENCE: 54
cagaagaact cgtcaagaag gcg                                             23

<210> SEQ ID NO 55
<211> LENGTH: 27
<212> TYPE: DNA
<213> ORGANISM: Artificial Sequence
<220> FEATURE:
<223> OTHER INFORMATION: Synthetic primer

<400> SEQUENCE: 55
gccagggcat ttctctattc tccaatc                                         27

<210> SEQ ID NO 56
<211> LENGTH: 22
<212> TYPE: DNA
<213> ORGANISM: Artificial Sequence
<220> FEATURE:
<223> OTHER INFORMATION: Synthetic primer

<400> SEQUENCE: 56
gaggtggggc actacaggat gc                                              22

<210> SEQ ID NO 57
<211> LENGTH: 20
<212> TYPE: DNA
<213> ORGANISM: Artificial Sequence
<220> FEATURE:
<223> OTHER INFORMATION: Synthetic primer

<400> SEQUENCE: 57
cgggtgtggg gttgagtgct                                                 20

<210> SEQ ID NO 58
<211> LENGTH: 23
<212> TYPE: DNA
<213> ORGANISM: Artificial Sequence
<220> FEATURE:
<223> OTHER INFORMATION: Synthetic primer
```

<400> SEQUENCE: 58
gacctccgta atcctttccc cat    23

<210> SEQ ID NO 59
<211> LENGTH: 24
<212> TYPE: DNA
<213> ORGANISM: Artificial Sequence
<220> FEATURE:
<223> OTHER INFORMATION: Synthetic primer

<400> SEQUENCE: 59
ttctggattt cacatgggtg gtgt    24

<210> SEQ ID NO 60
<211> LENGTH: 25
<212> TYPE: DNA
<213> ORGANISM: Artificial Sequence
<220> FEATURE:
<223> OTHER INFORMATION: Synthetic primer

<400> SEQUENCE: 60
gacaagcgtt agtaggcaca tatac    25

<210> SEQ ID NO 61
<211> LENGTH: 24
<212> TYPE: DNA
<213> ORGANISM: Artificial Sequence
<220> FEATURE:
<223> OTHER INFORMATION: Synthetic primer

<400> SEQUENCE: 61
gctccaattt cccacaacat tagt    24

<210> SEQ ID NO 62
<211> LENGTH: 132
<212> TYPE: DNA
<213> ORGANISM: Artificial Sequence
<220> FEATURE:
<223> OTHER INFORMATION: T7 promoter and sgRNA scaffold

<400> SEQUENCE: 62
gaattctaat acgactcact ataggggtc ttcgagaaga cctgttttag agctagaaat    60
agcaagttaa aataaggcta gtccgttatc aacttgaaaa agtggcaccg agtcggtgct    120
tttaaaggat cc    132

<210> SEQ ID NO 63
<211> LENGTH: 22
<212> TYPE: DNA
<213> ORGANISM: Artificial Sequence
<220> FEATURE:
<223> OTHER INFORMATION: Synthetic primer

<400> SEQUENCE: 63
gctttgggaa gctccaggta ag    22

<210> SEQ ID NO 64
<211> LENGTH: 24
<212> TYPE: DNA
<213> ORGANISM: Artificial Sequence
<220> FEATURE:
<223> OTHER INFORMATION: Synthetic primer

<400> SEQUENCE: 64
agacagcagc taaaagatgc ccag    24

<210> SEQ ID NO 65
<211> LENGTH: 24
<212> TYPE: DNA
<213> ORGANISM: Artificial Sequence
<220> FEATURE:
<223> OTHER INFORMATION: Synthetic primer

<400> SEQUENCE: 65
ctcccttcaa cagggaggca tgat                                           24

<210> SEQ ID NO 66
<211> LENGTH: 25
<212> TYPE: DNA
<213> ORGANISM: Artificial Sequence
<220> FEATURE:
<223> OTHER INFORMATION: Synthetic primer

<400> SEQUENCE: 66
ataactaccc ctgtccccac ttccg                                          25

<210> SEQ ID NO 67
<211> LENGTH: 83
<212> TYPE: DNA
<213> ORGANISM: Artificial Sequence
<220> FEATURE:
<223> OTHER INFORMATION: Junction sequence

<400> SEQUENCE: 67
gtttctcatc cttggtgtcc tttctctgct ccttttggtg actggggcct ttggctttca    60
ctggtggaga aaacaggtga gac                                            83

<210> SEQ ID NO 68
<211> LENGTH: 137
<212> TYPE: DNA
<213> ORGANISM: Artificial Sequence
<220> FEATURE:
<223> OTHER INFORMATION: Junction sequence

<400> SEQUENCE: 68
gagggactcc cctactctga attgccagga tgtccaagaa ggtagaaaca gagatgataa    60
aaatttgaaa gaaaaatttg aatggtttga tcaaagcttg aattccgaag ttcctattct   120
ctagaaagta taggaac                                                  137

<210> SEQ ID NO 69
<211> LENGTH: 116
<212> TYPE: DNA
<213> ORGANISM: Artificial Sequence
<220> FEATURE:
<223> OTHER INFORMATION: Junction sequence

<400> SEQUENCE: 69
agttcctatt ctctagaaag tataggaact tcatcagtca ggtacataat ggtgaaaaga    60
atgaggcata tattttgaa cccttgtctg cttttggcct agggctctgt taaaat        116

<210> SEQ ID NO 70
<211> LENGTH: 131
<212> TYPE: DNA
<213> ORGANISM: Artificial Sequence
<220> FEATURE:
<223> OTHER INFORMATION: Junction sequence

<400> SEQUENCE: 70

```
cttggctcaa tgcccttggc ctctcttttg ttccactagt tgtgtcttca gggccagggg      60
ctgaggtccc ggtggtgtgg gcccaggagg gggctcctgc ccagctcccc tgcagcccca     120
caatccccct c                                                          131

<210> SEQ ID NO 71
<211> LENGTH: 169
<212> TYPE: DNA
<213> ORGANISM: Artificial Sequence
<220> FEATURE:
<223> OTHER INFORMATION: Junction sequence

<400> SEQUENCE: 71
tcctcaccta cagagatggc ttcaacgtct ccatcatgta taacctcact gttctgggta      60
actcttctaa gcagccttga ccacaacctt cctgctcacc acctctcctg actcatgcat     120 ggaccccaa  aactttctca gctgcgtgtg gtctcactcc acatcactt                169

<210> SEQ ID NO 72
<211> LENGTH: 25
<212> TYPE: DNA
<213> ORGANISM: Artificial Sequence
<220> FEATURE:
<223> OTHER INFORMATION: Synthetic primer

<400> SEQUENCE: 72
ctcccttcaa cagggaggca tgatg                                            25

<210> SEQ ID NO 73
<211> LENGTH: 25
<212> TYPE: DNA
<213> ORGANISM: Artificial Sequence
<220> FEATURE:
<223> OTHER INFORMATION: Synthetic primer

<400> SEQUENCE: 73
cttcagaggg agtgacacct caggg                                            25

<210> SEQ ID NO 74
<211> LENGTH: 25
<212> TYPE: DNA
<213> ORGANISM: Artificial Sequence
<220> FEATURE:
<223> OTHER INFORMATION: Synthetic primer

<400> SEQUENCE: 74
caggatctct cagagcctcc gactg                                            25

<210> SEQ ID NO 75
<211> LENGTH: 26
<212> TYPE: DNA
<213> ORGANISM: Artificial Sequence
<220> FEATURE:
<223> OTHER INFORMATION: Synthetic primer

<400> SEQUENCE: 75
agacagcagc taaaagatgc ccagag                                           26
```